US010487363B2

(12) United States Patent
Manna et al.

(10) Patent No.: US 10,487,363 B2
(45) Date of Patent: Nov. 26, 2019

(54) COMPOSITIONS AND METHODS FOR DETECTING NEOPLASIA

(71) Applicant: The United States of America, as represented by the Secretary, Department of Health & Human Services, Rockville, MD (US)

(72) Inventors: Soumen K. Manna, Rockville, MD (US); Kristopher W. Krausz, Columbia, MD (US); Frank J. Gonzalez, Bethesda, MD (US)

(73) Assignee: The United States of America, as represented by the Secretary, Department of Health & Human Services, Rockville, MD (US)

( * ) Notice: Subject to any disclaimer, the term of this patent is extended or adjusted under 35 U.S.C. 154(b) by 363 days.

(21) Appl. No.: 14/762,426

(22) PCT Filed: Jan. 23, 2014

(86) PCT No.: PCT/US2014/012758
§ 371 (c)(1),
(2) Date: Jul. 21, 2015

(87) PCT Pub. No.: WO2014/116833
PCT Pub. Date: Jul. 31, 2014

(65) Prior Publication Data
US 2015/0344969 A1 Dec. 3, 2015

Related U.S. Application Data

(60) Provisional application No. 61/755,891, filed on Jan. 23, 2013.

(51) Int. Cl.
*C12Q 1/6886* (2018.01)
*G01N 33/68* (2006.01)
*G01N 33/574* (2006.01)

(52) U.S. Cl.
CPC ..... *C12Q 1/6886* (2013.01); *G01N 33/57419* (2013.01); *G01N 33/6806* (2013.01); *C12Q 2600/154* (2013.01); *C12Q 2600/158* (2013.01); *G01N 2800/50* (2013.01); *G01N 2800/52* (2013.01); *G01N 2800/56* (2013.01)

(58) Field of Classification Search
None
See application file for complete search history.

(56) References Cited

U.S. PATENT DOCUMENTS

2011/0177063 A1* 7/2011 Pannequin ........... C07K 5/1016
424/133.1

FOREIGN PATENT DOCUMENTS

WO WO-2012/024612 A1 2/2012
WO WO201227984 A1 * 9/2012

OTHER PUBLICATIONS

Bener et al. Biomedical Research 17(2): 149-154, 2006, 11 pages.*
Malaguarnera et al. World J. Gastroenterol. 12(28):4541-454, Jul. 28, 2006.*
Wang et al. World J. Gastroenterol. 10(9): 1297-1300, 2004.*
Denkert Carsten et al: "Metabolite profiling of human colon carcinoma a deregulation of TCA cycle and amino acid turnover", Molecular Cancer, Biomed Central, London, GB, vol. 7, No. 1, Sep. 18, 2008 (Sep. 18, 2008), p. 72.
Yunping Qiu et al: "Urinary Metabonomic Study on Colorectal Cancer", Journal of Proteome Research, vol. 9, No. 3, Mar. 5, 2010(Mar. 5, 2010), pp. 1627-1634.
Yunping Qiu et al: "Serum Metabolite Profiling of Human Colorectal Cancer Using GC-TOFMS and UPLC-QTOFMS", Journal of Proteome Research, vol. 8, No. 10, Oct. 2, 2009 (Oct. 2, 2009), pp. 4844-4850.
Stephanos Pavlides et al: "The autophagic tumor stroma model of cancer: Role of oxidative stress and ketone production in fueling tumor cell metabolism", Cell Cycle, vol. 9, No. 17, Sep. 1, 2010 (Sep. 1, 2010), pp. 3485-3505.
Masanori Yoshimatsu et al: "Dysregulation of PRMT1 and PRMT6, Type I arginine methyltransferases, is involved in various types of human cancers", International Journal of Cancer, vol. 128, No. 3, Nov. 27, 2010 (Nov. 27, 2010), pp. 562-573.
Soumen K. Manna et al: "Biomarkers of Coordinate Metabolic Reprogramming in Colorectal Tumors in Mice and Humans", Gastroenterology, Jan. 1, 2014 (Jan. 1, 2014).

* cited by examiner

*Primary Examiner* — Alana Harris Dent
(74) *Attorney, Agent, or Firm* — Locke Lord LLP; Nicholas J. DiCeglie, Jr.; Andrew W. Smith

(57) ABSTRACT

Compositions and methods for the diagnosis, treatment, and prevention of neoplasia (e.g., colorectal cancer).

19 Claims, 33 Drawing Sheets

Specification includes a Sequence Listing.

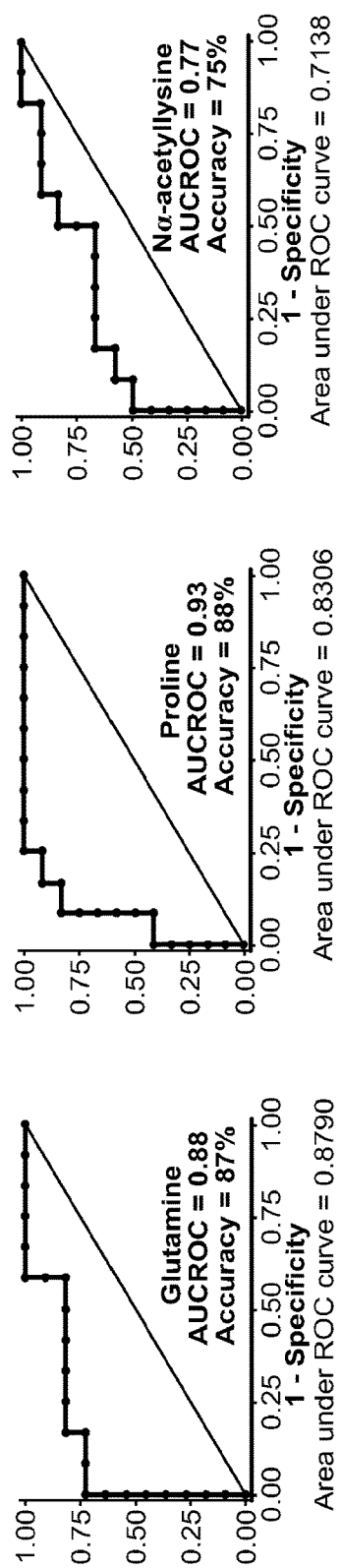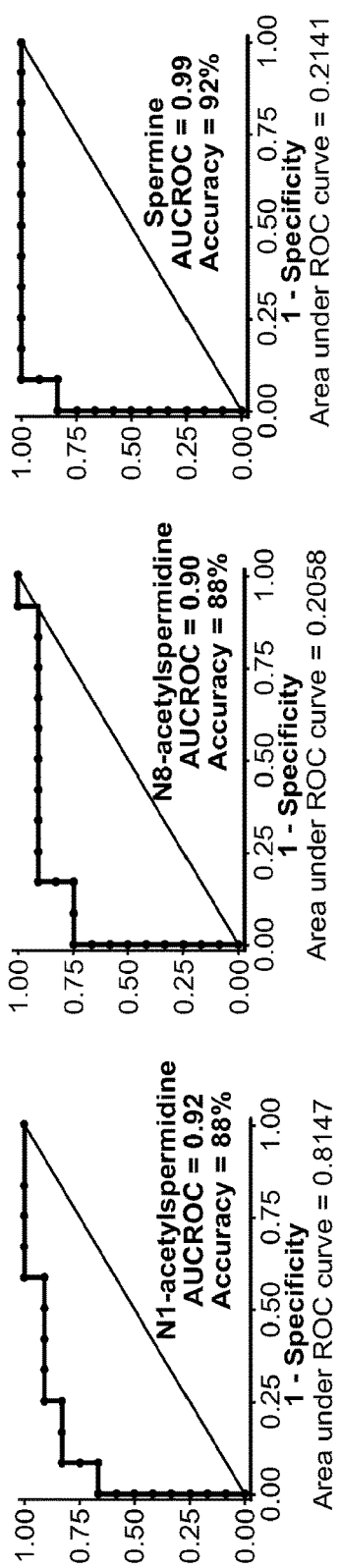
FIG. 9A
FIG. 9B

Xanthosine
AUCROC = 0.92
Accuracy = 92%
Area under ROC curve = 0.5234

Inosine
AUCROC = 0.96
Accuracy = 96%
Area under ROC curve = 0.3523

Deoxyuridine
AUCROC = 0.77
Accuracy = 79%
Area under ROC curve = 0.3600

Thymidine
AUCROC = 0.84
Accuracy = 83%
Area under ROC curve = 0.3600

Asymmetric dimethylarginine
AUCROC = 0.98
Accuracy = 92%
Area under ROC curve = 0.5199

Symmetric dimethylarginine
AUCROC = 0.95
Accuracy = 88%
Area under ROC curve = 0.2514

Carnitine
AUCROC = 0.99
Accuracy = 96%
Area under ROC curve = 0.2235

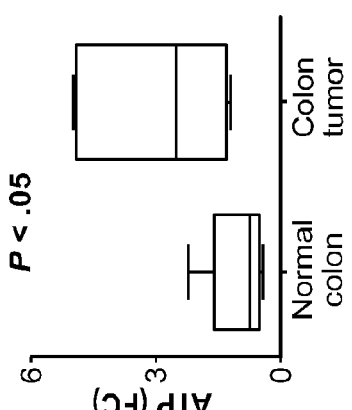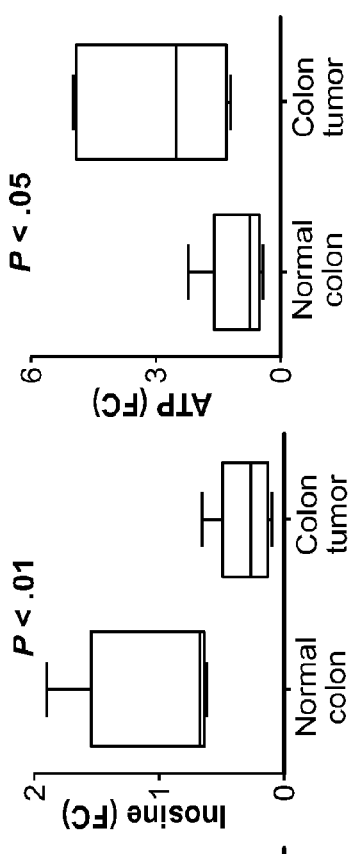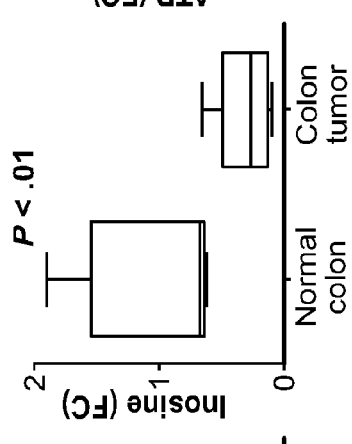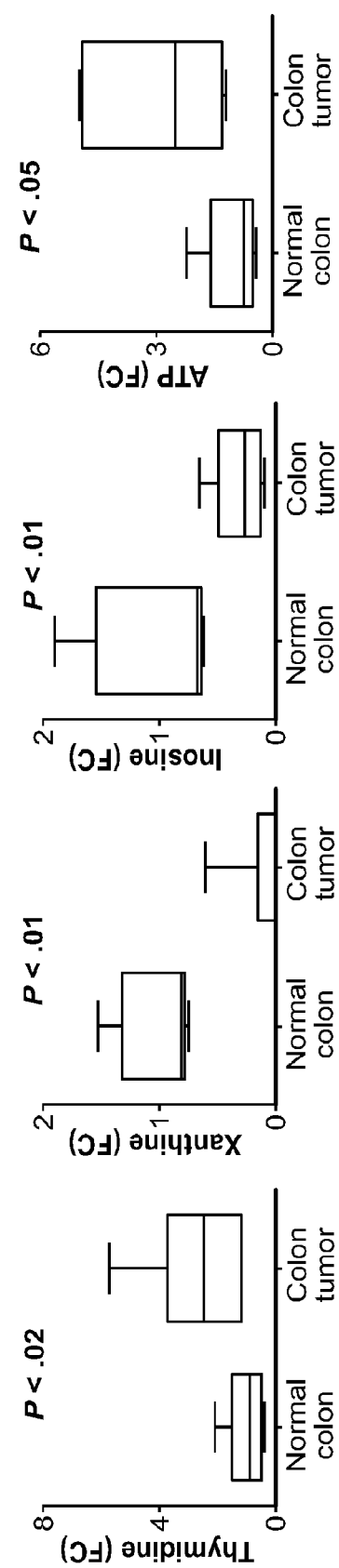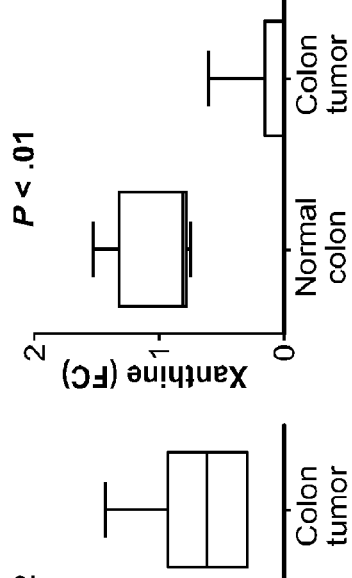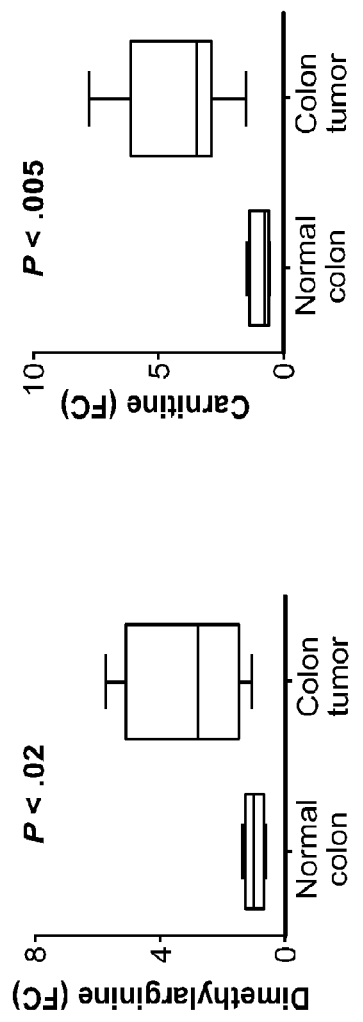
FIG. 15C
FIG. 15D

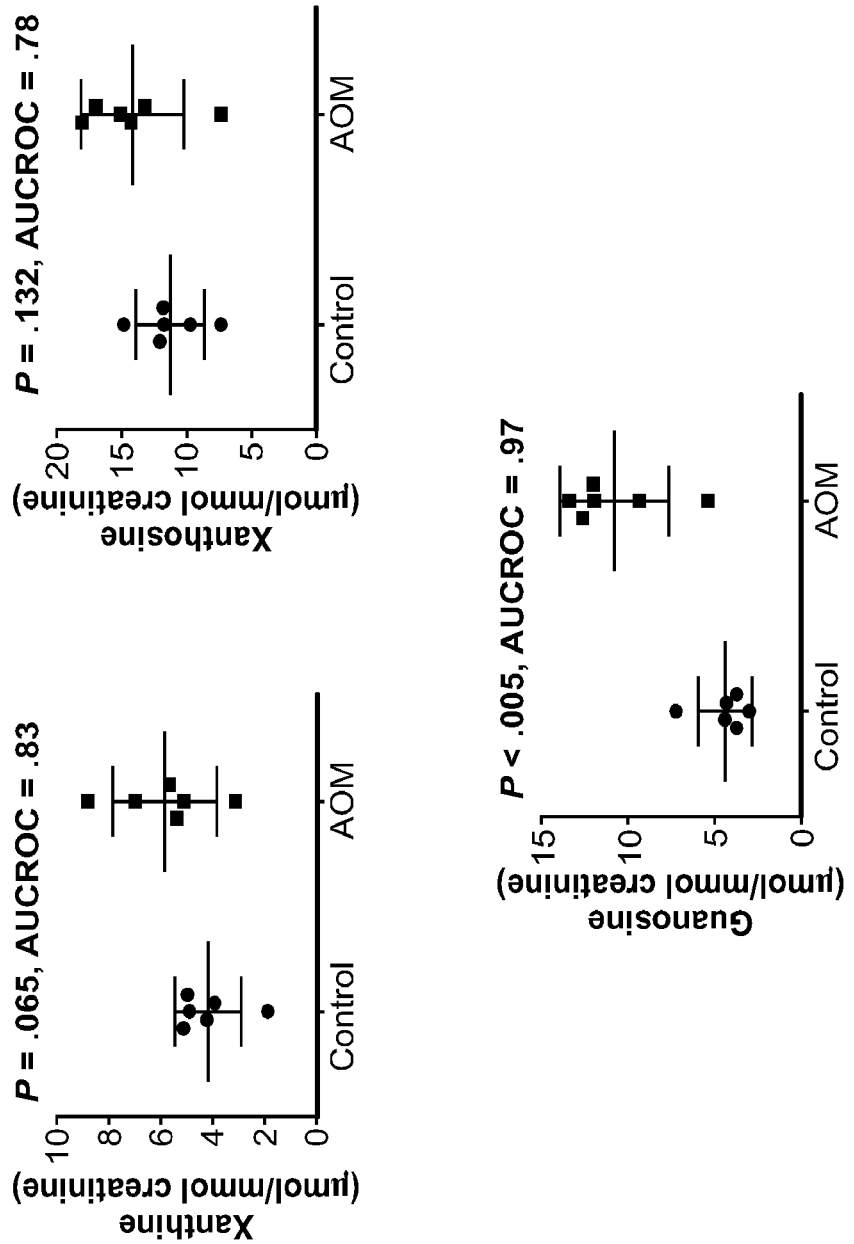

β-D-Ribofuranosylcreatine

A

M264:
$M+H^+$ = 264.119+
*Neutral mass*: 263.112
Calculated formulae: $C_9H_{17}N_3O_6$
Common Name: β-D-Ribofuranosylcreatine
IUPAC Name: 2-{2-{[(2R,3R,4S,5R)-3,4-dihydroxy-5-(hydroxymethyl)-oxolan-2-yl]-1-methylcarbamimidamido}acetic acid

B

P < 0.0001

M264 (μmol/mmol creatinine) — Control, CRC

C

AUCROC = 0.98

Sensitivity vs 1 - Specificity

COMPOSITIONS AND METHODS FOR DETECTING NEOPLASIA

RELATED APPLICATIONS

This application is a national stage application filed under 35 U.S.C. § 371 of International Application PCT/US2014/012758 (published Jul. 31, 2014 as WO 2014/116833) having an International filing date of Jan. 23, 2014 and which claims priority to U.S. Provisional Application No. 61/755,891, filed Jan. 23, 2013, the entire contents each of which are incorporated by reference in its their entireties herein.

STATEMENT OF RIGHTS TO INVENTIONS MADE UNDER FEDERALLY SPONSORED RESEARCH

This work was supported by the National Cancer Institute Intramural Research Program, National Institutes of Health. The Government has certain rights in this invention.

SEQUENCE LISTING

The instant application contains a Sequence Listing which has been submitted electronically in ascii format and is hereby incorporated by reference in its entirety. Said ascii copy is named 91921WO(47992)_sl.txt and is 843,776 bytes in size.

BACKGROUND OF THE INVENTION

Colorectal cancer is the second leading cause of cancer mortality in United States and fourth worldwide. Although colorectal cancer has good therapeutic response at early stages, advanced stages are frequently associated with metastasis and poor prognosis. Therefore, regular screening and early diagnosis of the disease is pivotal to therapeutic success. Currently used diagnostic procedures such as endoscopy and biopsy are invasive and time-consuming. The sensitivity and specificity of serum-based carcinoembryonic antigen test has also been found to be poor for early diagnosis. Lack of high-throughput noninvasive markers continues to contribute to avoidable healthcare burden and mortality.

Metabolomics has the potential to be a useful tool for identification of changes in biochemical signature associated with pathogenesis. However, tissue metabolomics, which requires biopsy samples, is also invasive. Moreover, there has been a general lack of studies investigating the mechanistic link between these biomarkers and changes in cancer tissue. Accordingly, high-throughput noninvasive methods for detecting neoplasia are urgently required.

SUMMARY OF THE INVENTION

As described below, the present invention features compositions and methods for the diagnosis, treatment, and prevention of neoplasia (e.g., colorectal cancer, small intestine cancer, duodenal cancer, gastric cancer, pancreatic cancer, liver cancer, esophageal cancer, ovarian cancer, prostate cancer, uterine cancer, breast cancer, thyroid cancer, and melanoma).

In one aspect, the invention generally features a method for identifying a subject as having or having a propensity to develop neoplasia, the method involving identifying an increased level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; and biomarkers related to amino acid metabolism, where an increase in the levels of two or more biomarkers identifies a subject as having or having a propensity to develop neoplasia.

In another aspect, the invention generally features a method for identifying a subject as having or having a propensity to develop neoplasia, the method involving identifying an increased level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine), where an increase in the levels of two or more biomarkers identifies a subject as having or having a propensity to develop neoplasia.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In another aspect, the invention features a method for determining the prognosis of neoplasia in a subject, the method involving identifying an increased level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; and biomarkers related to amino acid metabolism, thereby determining the prognosis of neoplasia in the subject.

In another aspect, the invention features a method for determining the prognosis of neoplasia in a subject, the method involving identifying an increased level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine), thereby determining the prognosis of neoplasia in the subject.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one embodiment, an increase in the level of asymmetric-dimethylarginine, symmetric-dimethylarginine, carnitine, methionine, dimethylglycine or betaine relative to the reference identifies the subject as having a reduced chance of survival. In a further embodiment, an increase in the level of asymmetric-dimethylarginine and symmetric-dimethylarginine relative to the reference identities the subject as having a reduced chance of survival.

In another embodiment, a decrease in the level of asymmetric-dimethylarginine, symmetric-dimethylarginine, carnitine, methionine, dimethylglycine or betaine relative to the reference identifies the subject as having an increased chance of survival. In a further embodiment, a decrease in the level of asymmetric-dimethylarginine and symmetric-dimethylarginine relative to the reference identifies the subject as having an increased chance of survival.

In another aspect, the invention features a method for monitoring response to neoplasia therapy in a subject, the method involving identifying an increased level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; biomarkers related to amino acid metabolism; thereby monitoring neoplasia therapy in the subject.

In another aspect, the invention features a method for monitoring response to neoplasia therapy in a subject, the method involving identifying an increased level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine), thereby monitoring neoplasia therapy in the subject.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one embodiment, a therapy that reduces the level of asymmetric-dimethylarginine, symmetric-dimethylarginine, carnitine, methionine, dimethylglycine, or betaine is identified as effective. In another particular embodiment, a therapy that reduces the level of asymmetric-dimethylarginine and symmetric-dimethylarginine is identified as effective.

In another embodiment, the reference is a sample obtained from the subject prior to therapy or at an earlier time point during therapy.

In one aspect, the invention features a method for characterizing the aggressiveness of a neoplasia in a subject, the method involving identifying an increased level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; and biomarkers related to amino acid metabolism, where an increased level of a biomarker related to methylation identifies the neoplasia as aggressive, and a decreased level of a biomarker related to methylation identifies the neoplasia as less aggressive.

In another aspect, the invention features a method for characterizing the aggressiveness of a neoplasia in a subject, the method involving identifying an increased level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine omithine, and citrulline; d biomarkers related to amino acid metabolism including proline, glutamine, glutamic acid, threonine, and Nα-acetyllysine; and M264 (β-D-Ribofuranosylcreatine), where an increased level of asymmetric-dimethylarginine and symmetric-dimethylarginine identifies the neoplasia as aggressive, and a decreased level of asymmetric-dimethylarginine and symmetric-dimethylarginine identifies the neoplasia as less aggressive.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one aspect, the invention features a method for identifying a subject as having or having a propensity to develop colorectal cancer, the method involving identifying an increased level of a combination of two or more biomarkers in a biological sample derived from the subject relative to the level present in a reference, where at least one biomarker is selected from the group of biomarkers related to methylation; and at least one additional marker is selected from a group from among the following: biomarkers related to nucleic acid metabolism; biomarkers related to urea cycle and polyamine metabolism; and biomarkers related to amino acid metabolism, where an increase in the levels of two or more biomarkers identifies a subject as having or having a propensity to develop neoplasia.

In another aspect, the invention features a method for identifying a subject as having or having a propensity to develop colorectal cancer, the method involving identifying an increased level of a combination of two or more biomarkers in a biological sample derived from the subject relative to the level present in a reference, where at least one biomarker is selected from the group of biomarkers related to methylation including asymmetric-dimethylarginine, symmetric-dimethylarginine, carnitine, methionine, dimethylglycine and betaine; and at least one additional marker is selected from a group from among the following:

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine, and M264 (β-D-Ribofuranosylcreatine), where an increase in the levels of two or more biomarkers identifies a subject as having or having a propensity to develop neoplasia.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one aspect, the invention features a method for identifying a subject as having or having a propensity to develop neoplasia, the method involving measuring the level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; and biomarkers related to amino acid metabolism, and correlating the measurements of the level of the measured biomarkers with the subject having neoplasia or the subject having a propensity to develop neoplasia.

In one embodiment, the subject is identified as having or having a propensity to develop neoplasia when the level of a biomarker related to methylation is increased relative to a reference.

In yet another aspect, the invention features a method for identifying a subject as having or having a propensity to develop neoplasia, the method involving measuring the level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine), and correlating the measurements of the level of the measured biomarkers with the subject having neoplasia or the subject having a propensity to develop neoplasia.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one embodiment, the subject is identified as having or having a propensity to develop neoplasia when the level of asymmetric-dimethylarginine, symmetric-dimethylarginine, carnitine, methionine, dimethylglycine, or betaine is increased relative to a reference.

In another embodiment, the subject is identified as having or having a propensity to develop neoplasia when the level of asymmetric-dimethylarginine and symmetric-dimethylarginine is increased relative to a reference.

In one aspect, the invention features a method for determining the prognosis of neoplasia in a subject, the method involving measuring the level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; and biomarkers related to amino acid metabolism, and correlating the measurements of the level of the measured biomarkers with the prognosis of neoplasia in the subject.

In one embodiment, the subject is identified as having a reduced chance of survival when the level of a biomarker related to methylation is increased relative to a reference. In another embodiment, the subject is identified as having an increased chance of survival when the level of a biomarker related to methylation is decreased relative to a reference.

In another aspect, the invention features a method for determining the prognosis of neoplasia in a subject, the method involving measuring the level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine, and M264 (β-D-Ribofuranosylcreatine), and correlating the measurements of the level of the measured biomarkers with the prognosis of neoplasia in the subject.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one embodiment, the subject is identified as having a reduced chance of survival when the level of asymmetric-dimethylarginine, symmetric-dimethylarginine, carnitine, methionine, dimethylglycine, or betaine is increased relative to a reference. In another embodiment, the subject is identified as having an increased chance of survival when the level of asymmetric-dimethylarginine, symmetric-dimethylarginine, carnitine, methionine, dimethylglycine, or betaine is decreased relative to a reference.

In one embodiment, the subject is identified as having a reduced chance of survival when the level of asymmetric-dimethylarginine and symmetric-dimethylarginine is increased relative to a reference. In another embodiment, the subject is identified as having an increased chance of survival when the level of asymmetric-dimethylarginine and symmetric-dimethylarginine is decreased relative to a reference.

In one aspect, the invention features a method for monitoring neoplasia therapy in a subject, the method involving measuring the level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; and biomarkers related to amino acid metabolism, and correlating the measurements of the level of the measured biomarkers to thereby monitor neoplasia therapy in the subject.

In another aspect, the invention features a method for monitoring neoplasia therapy in a subject, the method involving measuring the level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine), and correlating the measurements of the level of the measured biomarkers to thereby monitor neoplasia therapy in the subject.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one embodiment, a therapy that reduces the level of asymmetric-dimethylarginine, symmetric-dimethylarginine, carnitine, methionine, dimethylglycine, or betaine is identified as effective.

In another embodiment, a therapy that reduces the level of asymmetric-dimethylarginine and symmetric-dimethylarginine relative to a reference is identified as effective.

In one aspect, the invention features a method for characterizing the aggressiveness of a neoplasia in a subject, the method involving measuring the level of a combination of two or more biomarkers in a biological sample derived from the subject relative to the level present in a reference, where a first biomarker is selected from a first group and at least one additional marker is selected from a different group, where the groups are selected from among the following: biomarkers related to methylation; biomarkers related to nucleic acid metabolism; biomarkers related to urea cycle and polyamine metabolism; and biomarkers related to amino acid metabolism, and correlating the measurements of the level of the measured biomarkers to thereby characterize the aggressiveness of the neoplasia in the subject, where an increased level of a biomarker related to methylation relative to a reference, identifies the neoplasia as aggressive, and a decreased level of a biomarker related to methylation relative to a reference identifies the neoplasia as less aggressive.

In another aspect, the invention features a method for characterizing the aggressiveness of a neoplasia in a subject, the method involving measuring the level of a combination of two or more biomarkers in a biological sample derived from the subject relative to the level present in a reference, where a first biomarker is selected from a first group and at least one additional marker is selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine), and correlating the measurements of the level of the measured biomarkers to thereby characterize the aggressiveness of the neoplasia in the subject, where an increased level of asymmetric-dimethylarginine and symmetric-dimethylarginine relative to a reference, identifies the neoplasia as aggressive, and a decreased level of asymmetric-dimethylarginine and symmetric-dimethylarginine relative to a reference identifies the neoplasia as less aggressive.

In one embodiment, an increased level of asymmetric-dimethylarginine, symmetric-dimethylarginine, carnitine, methionine, dimethylglycine, and betaine relative to a reference, identifies the neoplasia as aggressive, and a decreased level of asymmetric-dimethylarginine, symmetric-dimethylarginine, carnitine, methionine, dimethylglycine, and betaine relative to a reference identifies the neoplasia as less aggressive.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one aspect, the invention features a method for identifying a subject as having or having a propensity to develop colorectal cancer, the method involving measuring the level of a combination of two or more biomarkers in a biological sample derived from the subject relative to the level present in a reference, where at least one biomarker is selected from the group of biomarkers related to methylation and at least one additional marker is selected from a group from among the following: biomarkers related to nucleic acid metabolism; biomarkers related to urea cycle and polyamine metabolism; and biomarkers related to amino acid metabolism, and correlating the measurements of the level of the measured biomarkers with the subject having neoplasia or the subject having a propensity to develop neoplasia, where the subject is identified as having or having a propensity to develop neoplasia when the level of a biomarker related to methylation is increased relative to a reference.

In another aspect, the invention features a method for identifying a subject as having or having a propensity to develop colorectal cancer, the method involving measuring the level of a combination of two or more biomarkers in a biological sample derived from the subject relative to the level present in a reference, where at least one biomarker is selected from the group of biomarkers related to methylation including asymmetric-dimethylarginine, symmetric-dimethylarginine, carnitine, methionine, dimethylglycine, and betaine and at least one additional marker is selected from a group from among the following:

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine), and correlating the measurements of the level of the measured biomarkers with the subject having neoplasia or the subject having a propensity to develop neoplasia, where the subject is identified as having or having a propensity to develop neoplasia when the level of asymmetric-dimethylarginine and symmetric-dimethylarginine is increased relative to a reference.

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one embodiment of any one of the above aspects, the methods feature measuring the level of M264 (β-D-ribofuranosylcreatine). In another embodiment of any one of the above aspects, the methods feature measuring the level of M264 (f-D-ribofuranosylcreatine) in addition to any one or more of the claimed biomarkers.

In one aspect, the invention features a kit for aiding the diagnosis of neoplasia or colorectal cancer, the kit including at least one reagent capable of detecting, binding, or capturing a first biomarker selected from a first group and at least one reagent capable of detecting, binding, or capturing at least one additional marker selected from a different group, where the groups are selected from among the following: biomarkers related to methylation; biomarkers related to nucleic acid metabolism; biomarkers related to urea cycle and polyamine metabolism; and biomarkers related to amino acid metabolism.

In another aspect, the invention features a kit for aiding the diagnosis of neoplasia or colorectal cancer, the kit including at least one reagent capable of detecting, binding, or capturing a first biomarker selected from a first group and at least one reagent capable of detecting, binding, or capturing at least one additional marker selected from a different group or M264, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine).

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In one aspect, the invention features a kit for aiding the diagnosis of neoplasia or colorectal cancer, the kit including at least one reagent capable of detecting, binding, or capturing at least one biomarker selected from the group of biomarkers related to methylation and at least one reagent capable of detecting, binding, or capturing at least one additional marker selected from a group from among the following: biomarkers related to nucleic acid metabolism; biomarkers related to urea cycle and polyamine metabolism; biomarkers related to amino acid metabolism.

In another aspect, the invention features a kit for aiding the diagnosis of neoplasia or colorectal cancer, the kit including at least one reagent capable of detecting, binding, or capturing at least one biomarker selected from the group of biomarkers related to methylation including asymmetric-dimethylarginine, symmetric-dimethylarginine, carnitine, methionine, dimethylglycine, and betaine and at least one reagent capable of detecting, binding, or capturing at least one additional marker selected from a group from among the following:

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine omithine, and citrulline;

biomarkers related to amino acid metabolism including proline, glutamine, glutamic acid, threonine, and Nα-acetyllysine; and M264 (β-D-Ribofuranosylcreatine).

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In another aspect, the invention features a kit for aiding the diagnosis of neoplasia or colorectal cancer, the kit containing at least one reagent capable of detecting, binding, or capturing asymmetric-dimethylarginine and at least one reagent capable of detecting, binding, or capturing symmetric-dimethylarginine.

In another embodiment, the kit further contains at least one reagent capable of detecting, binding or capturing carnitine, methionine, dimethylglycine, and betaine.

In another embodiment, the kit further contains at least one reagent capable of detecting the M264 biomarker.

In one embodiment, the kit further contains at least one reagent capable of detecting, binding, or capturing proline, glutamine, glutamic acid, threonine, Nα-acetyllysine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline, and M264 (β-D-Ribofuranosylcreatine), or a combination of reagents thereof.

In another embodiment, the kit further contains directions for using the reagent to analyze the level of asymmetric-dimethylarginine, symmetric-dimethylarginine, carnitine, methionine, dimethylglycine, betaine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline, proline, glutamine, glutamic acid, threonine, and Nα-acetyllysine, M264 (β-D-Ribofuranosylcreatine), or a combination thereof.

In another embodiment, the kit further contains directions for contacting a test sample with the reagent and detecting asymmetric-dimethylarginine, symmetric-dimethylarginine, carnitine, methionine, dimethylglycine, betaine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline, proline, glutamine, glutamic acid, threonine, and Nα-acetyllysine, M264 (β-D-Ribofuranosylcreatine), or a combination thereof retained by the reagent.

In another aspect, the invention features a panel for aiding the diagnosis of neoplasia or colorectal cancer, the panel including at least one reagent capable of detecting, binding, or capturing at least one biomarker selected from the group of biomarkers related to methylation; biomarkers related to nucleic acid metabolism; biomarkers related to urea cycle and polyamine metabolism; and biomarkers related to amino acid metabolism.

In yet another aspect, the invention provides a panel for aiding the diagnosis of neoplasia or colorectal cancer, the panel containing at least one reagent capable of detecting, binding, or capturing a first biomarker selected from a first group and at least one reagent capable of detecting, binding, or capturing at least one additional marker selected from a different group, where the groups are selected from among the following:

biomarkers related to methylation including asymmetric-dimethylarginine, symmetric-dimethylarginine, carnitine, methionine, dimethylglycine, and betaine;

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine).

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In another aspect, the invention features a panel for aiding the diagnosis of neoplasia or colorectal cancer, the panel including at least one reagent capable of detecting, binding, or capturing at least one biomarker selected from the group of biomarkers related to methylation including asymmetric-dimethylarginine, symmetric-dimethylarginine, carnitine, methionine, dimethylglycine, and betaine and at least one reagent capable of detecting, binding, or capturing at least one additional marker selected from a group from among the following:

biomarkers related to nucleic acid metabolism including xanthosine, inosine, deoxyuridine, thymidine, deoxycytidine, cytosine, hypoxanthine, xanthine, uracil, guanosine, and adenosine;

biomarkers related to urea cycle and polyamine metabolism including N1-acetylspermidine, N8-acetylspermidine, spermine, arginine ornithine, and citrulline;

biomarkers related to amino acid metabolism including proline, glutamine, glutamic acid, threonine, and Nα-acetyllysine; and M264 (β-D-Ribofuranosylcreatine).

In one embodiment, the groups are selected from the following:

biomarkers related to methylation comprising asymmetric-dimethylarginine and symmetric-dimethylarginine;

biomarkers related to nucleic acid metabolism comprising xanthosine, inosine, deoxyuridine, and thymidine;

biomarkers related to polyamine metabolism comprising N1-acetylspermidine, N8-acetylspermidine, and spermine; and biomarkers related to amino acid metabolism comprising proline, glutamine, and Nα-acetyllysine.

In another aspect, the invention features a panel for aiding the diagnosis of neoplasia or colorectal cancer, the panel including at least one reagent capable of detecting, binding, or capturing asymmetric-dimethylarginine and at least one reagent capable of detecting or capturing symmetric-dimethylarginine. In one embodiment, the reagent is one or more of an organic molecule, peptide, peptide mimetic, polypeptide, nucleic acid ligand, aptamer, or antibody.

In another embodiment, the panel further contains at least one reagent capable of detecting, capturing, or binding carnitine, methionine, dimethylglycine, betaine, xanthosine, inosine, deoxyuridine, thymidine, deoxycytidine, cytosine, hypoxanthine, xanthine, uracil, guanosine, and adenosine, N1-acetylspermidine, N8-acetylspermidine, spermine, arginine ornithine, and citrulline, proline, glutamine, glutamic acid, threonine, Nα-acetyllysine and M264 (β-D-Ribofuranosylcreatine), or a combination of reagents thereof.

In various embodiments of any of the above aspects or any other aspect of the invention delineated herein, the invention further provides measuring the level of biomarkers in one or more groups including one or more of biomarkers related to methylation; biomarkers related to polyamine metabolism; and biomarkers related to amino acid metabolism. In various embodiments of the above aspects, an increase in the level of biomarkers in one or more of the groups identifies a subject as having or having a propensity to develop neoplasia; identifies a subject as having a reduced chance of survival; or identifies a neoplasia as aggressive. In other embodiments, a decrease in the level of biomarkers in one or more of the groups identifies a subject as having an increased chance of survival; identifies a therapy as effective; or identifies a neoplasia as less aggressive. In other embodiments, the biological sample is a biological fluid (e.g., urine, blood, blood serum, plasma, bile, fecal aspirate, intestinal aspirate, cerebrospinal fluid and saliva) or tissue sample. In various embodiments of the above aspects, the method further involves measuring the level of carnitine in the biological sample. In other embodiments a decrease in the level of carnitine in a biological sample that is a biological fluid identifies a subject as having or having a propensity to develop neoplasia; identifies a subject as having a reduced chance of survival; or identifies a neoplasia as aggressive. In still other embodiments, an increase in the level of carnitine in a biological sample that is a biological fluid identifies a subject as having an increased chance of survival; identifies a therapy as effective; or identifies a neoplasia as less aggressive.

In other embodiments, an increase in the level of carnitine in a biological sample that is a tissue sample identifies a subject as having or having a propensity to develop neoplasia; identifies a subject as having a reduced chance of survival; or identifies a neoplasia as aggressive. In still other embodiments, a decrease in the level of carnitine in a biological sample that is a tissue sample identifies a subject as having an increased chance of survival; identifies a therapy as effective; or identifies a neoplasia as less aggressive.

In various embodiments of the above aspects, the neoplasia is colorectal cancer, small intestine cancer, duodenal cancer, gastric cancer, pancreatic cancer, liver cancer, esophageal cancer, ovarian cancer, prostate cancer, uterine cancer, breast cancer, thyroid cancer or melanoma. In other embodiments, the neoplasia contains a mutation in APC or a Wnt signaling pathway protein. In still other embodiments of the above aspects, the method further involves detecting a mutation in APC or a Wnt signaling pathway protein. In other embodiments, the level of the biomarker is increased 1.5, 2, 2.5, 3, 3.5, 4, 5, 6, 7, 8, 9, 10, 11, 12, 13, 14, 15-fold or more relative to the reference. In still other embodiments, the reference is a control or a corresponding biological sample derived from a healthy subject. In still other embodiments, the level of the biomarker is normalized to the level of creatinine in the sample, absolute concentration, 24-hr excretion, or with respect to specific gravity. In still other embodiments, the subject is human. In still other embodiments, the level is detected by chromatography, mass spectrometry, spectroscopy, immunoassay, ultra performance liquid chromatography (UPLC). In other embodiments, the mass spectrometry is electrospray ionization quadruple time-of-flight mass spectrometry (ESI-QTF-MS). In other embodiments, spectroscopy is NMR spectroscopy. In other embodiments, the immunoassay is ELISA. In still other embodiments, the method further involves measuring the level of biomarkers in one or more groups from among biomarkers related to methylation; biomarkers related to polyamine metabolism; and biomarkers related to amino acid metabolism. In other embodiments, an increase in the level of biomarkers in one or more of the groups identifies a subject as having or having a propensity to develop neoplasia; identifies a subject as having a reduced chance of survival; or identifies a neoplasia as aggressive. In still other embodiments, an increase in the level of biomarkers in one or more of the groups identifies a subject as having an increased chance of survival; identifies a therapy as effective; or identifies a neoplasia as less aggressive.

The invention provides compositions and methods for diagnosing, treating or preventing neoplasia (e.g., colorectal cancer). Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "biomarker" generally refers to a molecule that is differentially present in a sample (e.g., biopsy, biological or physiological fluid) taken from a subject of one phenotypic status (e.g., having a disease) as compared with another phenotypic status (e.g., not having the disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and of drug toxicity.

As used herein, the term "biomarker related to methylation" refers to metabolic intermediates and products related to increased methylation (e.g., protein methylation, DNA methylation) in a subject or a tissue or a cell of the subject (e.g., a neoplastic tissue or cell). In various embodiments, the biomarker related to methylation is a small molecule compound. In various embodiments, the biomarker related to methylation is present in a sample derived from the subject (e.g., a biological or physiological fluid). In particular embodiments, an alteration in the levels of one or more biomarkers related to methylation, relative to a reference, indicates a tissue or cell is neoplastic. In specific embodiments, an alteration in the levels of one or more biomarkers related to methylation, relative to a reference, indicates a subject has or is at risk of having neoplasia. Exemplary biomarkers related to methylation include without limitation: asymmetric-dimethylarginine; symmetric-dimethylarginine; carnitine; N-monomethylarginine (CAS: 17035-90-4); N(6)-methyllysine (CAS: 1188-07-4); N6,N6 dimethyllysine (CAS: 2259-86-1, CID: 4478779, InChIKey: XXEWFEBMSGLYBY-UHFFFAOYSA-N); N6,N6,N6 trimethyllysine (CAS: 19253-88-4); Sarcosine (CAS: 107-97-1); Betaine (CAS: 107-43-7); Dimethylglycine (CAS: 1118-68-9); 1-methylhistidine (CAS: 332-80-9); 3-methylhistidine (CAS: 368-16-1); Trigonelline (CAS: 535-83-1); N-methylnicotinamide (CAS: 114-33-0); 1-methylnicotinamide (CAS: 3106-60-3); 6-methylnicotinamide (CAS: 6960-22-1); Methionine (CAS: 63-68-3); homocysteine (CAS: 454-29-5); S-adenosylhomocysteine (CAS: 979-92-0); S-adenosylmethionine (CAS: 29908-03-0); Trimethyl-ammonioacetate (InChIKey: KWIUHFFTVRNATP-UHFFFAOYSA-O); Trimethylamine (CAS: 75-50-3); Trimethylamine N-oxide (CAS: 1184-78-7); Dimethylamine (CAS: 124-40-3); N-Formyl-L-methionine (CAS: 4289-98-9); Folic acid (CAS: 59-30-3); Tetrahydrofolic acid (CAS: 135-16-0); choline (CAS: 62-49-7); phosphorylcholine (CAS: 3616-04-4); glycerophosphocholine (CAS: 28319-77-9); acetylcarnitine (CAS: 3040-38-8); propionylcarnitine (CAS: 17298-37-2); butyrylcarnitine (CAS: 25576-40-3); and isobutyrylcarnitine (CAS: 25518-49-4); including pharmaceutically acceptable salts, solvates, hydrates, geometrical isomers, tautomers, optical isomers, isotopic derivatives, polymorphs, prodrugs, and N-oxides thereof. In certain exemplary embodiments, biomarkers related to methylation include asymmetric-dimethylarginine, symmetric-dimethylarginine, carnitine, methionine, dimethylglycine, and betaine.

As used herein, the term "biomarker related to nucleic acid metabolism" refers to metabolic intermediates and products related to increased nucleic acid metabolism in a subject or a tissue or a cell of the subject (e.g., a neoplastic tissue or cell). In various embodiments, the biomarker related to nucleic acid metabolism is a small molecule compound. In various embodiments, the biomarker related to nucleic acid metabolism is present in a sample derived from the subject (e.g., a biological or physiological fluid). In particular embodiments, an alteration in the levels of one or more biomarkers related to nucleic acid metabolism, relative to a reference, indicates a tissue or cell is neoplastic. In specific embodiments, an alteration in the levels of one or more biomarkers related to nucleic acid metabolism, relative to a reference, indicates a subject has or is at risk of having neoplasia. Exemplary biomarkers related to nucleic acid metabolism include without limitation: xanthosine (CAS: 146-80-5); inosine (CAS: 58-63-9); deoxyuridine (CAS: 951-78-0); thymidine (CAS: 50-89-5); Uric acid (CAS: 69-93-2); S-allantoin (CAS: 97-59-6); Xanthine (CAS: 69-89-6); Hypoxanthine (CAS: 68-94-0); Guanine (CAS: 73-40-5); Guanosine (CAS: 118-00-3); Deoxyguanosine (CAS: 961-07-9); Adenine (CAS: 73-24-5); Adenosine (CAS: 58-61-7); Deoxyadenosine (CAS: 958-09-8); FAPy-adenine (CAS: 5122-36-1); 1-Methyladenine (CAS: 5142-

22-3); Deoxyonosine (CAS: 890-38-0); uracil (CAS: 66-22-8); uridine (CAS: 58-96-8); dihydrouracil (CAS: 504-07-4); dihydrouridine (CAS: 5627-05-4); Orotic acid (CAS: 65-86-1); Thymine (CAS: 65-71-4); dihydrothymine (CAS: 696-04-8); Ureidopropionic acid (CAS: 462-88-4); beta-Alanine (CAS: 107-95-9); Ureidoisobutyric acid (CAS: 2905-86-4); 4,5-Dihydroorotic acid (CAS: 155-54-4); 5-Methylcytidine (CAS: 2140-61-6); 5-Methyldeoxycytidine (CAS: 838-07-3); Carbamoylphosphate (CAS: 590-55-6); and 5-Hydroxymethyluracil (CAS: 4433-40-3); including pharmaceutically acceptable salts, solvates, hydrates, geometrical isomers, tautomers, optical isomers, isotopic derivatives, polymorphs, prodrugs, and N-oxides thereof. In certain exemplary embodiments, biomarkers related to nucleic acid metabolism include xanthosine, inosine, deoxyuridine, thymidine, deoxycytidine, cytosine, hypoxanthine, xanthine, uracil, guanosine, and adenosine.

As used herein, the term "biomarker related to urea cycle and polyamine metabolism" refers to metabolic intermediates and products related to increased polyamine metabolism in a subject or a tissue or a cell of the subject (e.g., a neoplastic tissue or cell). In various embodiments, the biomarker related to polyamine metabolism is a small molecule compound. In various embodiments, the biomarker related to polyamine metabolism is present in a sample derived from the subject (e.g., a biological or physiological fluid). In particular embodiments, an alteration in the levels of one or more biomarkers related to polyamine metabolism, relative to a reference, indicates a tissue or cell is neoplastic. In specific embodiments, an alteration in the levels of one or more biomarkers related to polyamine metabolism, relative to a reference, indicates a subject has or is at risk of having neoplasia. Exemplary biomarkers related to urea cycle and polyamine metabolism include without limitation: N1-acetylspermidine (CAS: 14278-49-0); N8-acetylspermidine (CAS: 34450-15-2); spermine (CAS: 71-44-3); Putrescine (CAS: 110-60-1); spermidine (CAS: 124-20-9); ornithine (CAS: 70-26-8); Citrulline (CAS: 372-75-8); L-arginine (CAS: 74-79-3); N-acetylputrescine (CAS: 124-20-9); N1-acetylspermine (CAS: 25593-72-0); and L-argininosuccinic acid (CAS: 2387-71-5) including pharmaceutically acceptable salts, solvates, hydrates, geometrical isomers, tautomers, optical isomers, isotopic derivatives, polymorphs, prodrugs, and N-oxides thereof. In certain exemplary embodiments, biomarkers related to polyamine metabolism include biomarkers related to urea cycle and polyamine metabolism including N1-acetylspermidine, N8-acetylspermidine, spermine, arginine ornithine, and citrulline.

As used herein, the term "biomarker related to amino acid metabolism" refers to metabolic intermediates and products related to increased amino acid metabolism in a subject or a tissue or a cell of the subject (e.g., a neoplastic tissue or cell). In various embodiments, the biomarker related to amino acid metabolism is a small molecule compound. In various embodiments, the biomarker related to amino acid metabolism is present in a sample derived from the subject (e.g., a biological or physiological fluid). In particular embodiments, an alteration in the levels of one or more biomarkers related to amino acid metabolism, relative to a reference, indicates a tissue or cell is neoplastic. In specific embodiments, an alteration in the levels of one or more biomarkers related to amino acid metabolism, relative to a reference, indicates a subject has or is at risk of having neoplasia. Exemplary biomarkers related to amino acid metabolism include without limitation: proline (CAS: 609-36-9 or 147-85-3); glutamine (CAS: 56-85-9); Nα-acetyllysine (CAS: 1946-82-3); Serine (CAS: 56-45-1); Threonine (CAS: 72-19-5); glycine (CAS: 56-40-6); asparagine (CAS: 70-47-3); aspartic acid (CAS: 56-84-8); glutamic acid (CAS: 56-86-0); 4-hydroxyproline (CAS: 30724-02-8); 2-ketoglutaric acid (CAS: 18465-19-5); 2-hydroxyglutaric acid (CAS: 2889-31-8); Oxaloacetic acid (CAS: 328-42-7); Fumaric acid (CAS: 110-17-8); Lysine (CAS: 923-27-3); Creatine (CAS: 57-00-1); Creatinine (CAS: 60-27-5); Phoshocreatine (CAS: 67-07-2); Guanidinoacetic acid (CAS: 352-97-6); and N(6)-Methyllysine (CAS: 1188-07-4); including pharmaceutically acceptable salts, solvates, hydrates, geometrical isomers, tautomers, optical isomers, isotopic derivatives, polymorphs, prodrugs, and N-oxides thereof. In certain exemplary embodiments, biomarkers related to amino acid metabolism include proline, glutamine, glutamic acid, threonine, and Nα-acetyllysine.

As used herein, the term "asymmetric-dimethylarginine (ADMA)" refers to a compound having the CAS number 102783-24-4, including a pharmaceutically acceptable salt, solvate, hydrate, geometrical isomer, tautomer, optical isomer, isotopic derivative, polymorph, prodrug, or N-oxide thereof. An increase in asymmetric-dimethylarginine in a biological sample is related to an increase in methylation (e.g. protein methylation, DNA methylation) in a subject or a tissue or a cell of the subject (e.g., a neoplastic tissue or cell).

As used herein, the term "symmetric-dimethylarginine (SDMA)" refers to a compound having the CAS number 30344-00-4, including a pharmaceutically acceptable salt, solvate, hydrate, geometrical isomer, tautomer, optical isomer, isotopic derivative, polymorph, prodrug, or N-oxide thereof. An increase in symmetric-dimethylarginine in a biological sample is related to an increase in methylation (e.g. protein methylation, DNA methylation) in a subject or a tissue or a cell of the subject (e.g., a neoplastic tissue or cell).

As used herein, the term "carnitine" refers to a compound having the CAS number 541-15-1, including a pharmaceutically acceptable salt, solvate, hydrate, geometrical isomer, tautomer, optical isomer, isotopic derivative, polymorph, prodrug, or N-oxide thereof. A decrease in carnitine in a biological fluid sample is related to an increase in methylation (e.g. protein methylation, DNA methylation) in a subject or a tissue or a cell of the subject (e.g., a neoplastic tissue or cell). A decrease in carnitine in a biological tissue sample is related to an increase in methylation in a subject or a tissue or a cell of the subject (e.g., a neoplastic tissue or cell).

As used herein, the term "methionine" refers to a compound having the CAS number 63-68-3, including a pharmaceutically acceptable salt, solvate, hydrate, geometrical isomer, tautomer, optical isomer, isotopic derivative, polymorph, prodrug, or N-oxide thereof. An increase in methionine in a biological sample is related to an increase in nucleic acid metabolism in a subject or a tissue or a cell of the subject (e.g., a neoplastic tissue or cell).

As used herein, the term "dimethylglycine" refers to a compound having the CAS number 1118-68-9, including a pharmaceutically acceptable salt, solvate, hydrate, geometrical isomer, tautomer, optical isomer, isotopic derivative, polymorph, prodrug, or N-oxide thereof. An increase in dimethylglycine in a biological sample is related to an increase in nucleic acid metabolism in a subject or a tissue or a cell of the subject (e.g., a neoplastic tissue or cell).

As used herein, the term "betaine' refers to a compound having the CAS number 107-43-7, including a pharmaceutically acceptable salt, solvate, hydrate, geometrical isomer, tautomer, optical isomer, isotopic derivative, polymorph, prodrug, or N-oxide thereof. An increase in betaine in a biological sample is related to an increase in nucleic acid metabolism in a subject or a tissue or a cell of the subject (e.g., a neoplastic tissue or cell).

As used herein, the term "xanthosine" refers to a compound having the CAS number 146-80-5, including a pharmaceutically acceptable salt, solvate, hydrate, geometrical isomer, tautomer, optical isomer, isotopic derivative, polymorph, prodrug, or N-oxide thereof. An increase in xanthosine in a biological sample is related to an increase in nucleic acid metabolism in a subject or a tissue or a cell of the subject (e.g., a neoplastic tissue or cell).

As used herein, the term "inosine" refers to a compound having the CAS number 58-63-9, including a pharmaceutically acceptable salt, solvate, hydrate, geometrical isomer, tautomer, optical isomer, isotopic derivative, polymorph, prodrug, or N-oxide thereof. An increase in inosine in a biological sample is related to an increase in nucleic acid metabolism in a subject or a tissue or a cell of the subject (e.g., a neoplastic tissue or cell).

As used herein, the term "deoxyuridine" refers to a compound having the CAS number 951-78-0, including a pharmaceutically acceptable salt, solvate, hydrate, geometrical isomer, tautomer, optical isomer, isotopic derivative, polymorph, prodrug, or N-oxide thereof. An increase in deoxyuridine in a biological sample is related to an increase in nucleic acid metabolism in a subject or a tissue or a cell of the subject (e.g., a neoplastic tissue or cell).

As used herein, the term "thymidine" refers to a compound having the CAS number 50-89-5, including a pharmaceutically acceptable salt, solvate, hydrate, geometrical isomer, tautomer, optical isomer, isotopic derivative, polymorph, prodrug, or N-oxide thereof. An increase in thymidine in a biological sample is related to an increase in nucleic acid metabolism in a subject or a tissue or a cell of the subject (e.g., a neoplastic tissue or cell).

As used herein, the term "deoxycytidine" refers to a compound having the CAS number 951-77-9, including a pharmaceutically acceptable salt, solvate, hydrate, geometrical isomer, tautomer, optical isomer, isotopic derivative, polymorph, prodrug, or N-oxide thereof. An increase in deoxycytidine in a biological sample is related to an increase in nucleic acid metabolism in a subject or a tissue or a cell of the subject (e.g., a neoplastic tissue or cell).

As used herein, the term "cytosine" refers to a compound having the CAS number 71-30-7, including a pharmaceutically acceptable salt, solvate, hydrate, geometrical isomer, tautomer, optical isomer, isotopic derivative, polymorph, prodrug, or N-oxide thereof. An increase in cytosine in a biological sample is related to an increase in nucleic acid metabolism in a subject or a tissue or a cell of the subject (e.g., a neoplastic tissue or cell).

As used herein, the term "hypoxanthine" refers to a compound having the CAS number CAS: 68-94-0, including a pharmaceutically acceptable salt, solvate, hydrate, geometrical isomer, tautomer, optical isomer, isotopic derivative, polymorph, prodrug, or N-oxide thereof. An increase in hypoxanthine in a biological sample is related to an increase in nucleic acid metabolism in a subject or a tissue or a cell of the subject (e.g., a neoplastic tissue or cell).

As used herein, the term "xanthine" refers to a compound having the CAS number CAS: 69-89-6, including a pharmaceutically acceptable salt, solvate, hydrate, geometrical isomer, tautomer, optical isomer, isotopic derivative, polymorph, prodrug, or N-oxide thereof. An increase in xanthine in a biological sample is related to an increase in nucleic acid metabolism in a subject or a tissue or a cell of the subject (e.g., a neoplastic tissue or cell).

As used herein, the term "uracil" refers to a compound having the CAS number CAS: 66-22-8, including a pharmaceutically acceptable salt, solvate, hydrate, geometrical isomer, tautomer, optical isomer, isotopic derivative, polymorph, prodrug, or N-oxide thereof. An increase in uracil in a biological sample is related to an increase in nucleic acid metabolism in a subject or a tissue or a cell of the subject (e.g., a neoplastic tissue or cell).

As used herein, the term "guanosine" refers to a compound having the CAS number CAS: 118-00-3, including a pharmaceutically acceptable salt, solvate, hydrate, geometrical isomer, tautomer, optical isomer, isotopic derivative, polymorph, prodrug, or N-oxide thereof. An increase in guanosine in a biological sample is related to an increase in nucleic acid metabolism in a subject or a tissue or a cell of the subject (e.g., a neoplastic tissue or cell).

As used herein, the term "adenosine" refers to a compound having the CAS number CAS: 58-61-7, including a pharmaceutically acceptable salt, solvate, hydrate, geometrical isomer, tautomer, optical isomer, isotopic derivative, polymorph, prodrug, or N-oxide thereof. An increase in adenosine in a biological sample is related to an increase in nucleic acid metabolism in a subject or a tissue or a cell of the subject (e.g., a neoplastic tissue or cell).

As used herein, the term "N1-acetylspermidine" refers to a compound having the CAS number 14278-49-0, including a pharmaceutically acceptable salt, solvate, hydrate, geometrical isomer, tautomer, optical isomer, isotopic derivative, polymorph, prodrug, or N-oxide thereof. An increase in N1-acetylspermidine in a biological sample is related to an increase in polyamine metabolism in a subject or a tissue or a cell of the subject (e.g., a neoplastic tissue or cell).

As used herein, the term "N8-acetylspermidine" refers to a compound having the CAS number 34450-15-2, including a pharmaceutically acceptable salt, solvate, hydrate, geometrical isomer, tautomer, optical isomer, isotopic derivative, polymorph, prodrug, or N-oxide thereof. An increase in N8-acetylspermidine in a biological sample is related to an increase in polyamine metabolism in a subject or a tissue or a cell of the subject (e.g., a neoplastic tissue or cell).

As used herein, the term "spermine" refers to a compound having the CAS number 71-44-3, including a pharmaceutically acceptable salt, solvate, hydrate, geometrical isomer, tautomer, optical isomer, isotopic derivative, polymorph, prodrug, or N-oxide thereof. An increase in spermine in a biological sample is related to an increase in polyamine metabolism in a subject or a tissue or a cell of the subject (e.g., a neoplastic tissue or cell).

As used herein, the term "arginine" refers to a compound having the CAS number CAS: 74-79-3, including a pharmaceutically acceptable salt, solvate, hydrate, geometrical isomer, tautomer, optical isomer, isotopic derivative, polymorph, prodrug, or N-oxide thereof. An increase in arginine in a biological sample is related to an increase in polyamine metabolism in a subject or a tissue or a cell of the subject (e.g., a neoplastic tissue or cell).

As used herein, the term "ornithine" refers to a compound having the CAS number CAS: 70-26-8, including a pharmaceutically acceptable salt, solvate, hydrate, geometrical isomer, tautomer, optical isomer, isotopic derivative, polymorph, prodrug, or N-oxide thereof. An increase in ornithine in a biological sample is related to an increase in polyamine metabolism in a subject or a tissue or a cell of the subject (e.g., a neoplastic tissue or cell).

As used herein, the term "citrulline" refers to a compound having the CAS number CAS: 372-75-8, including a pharmaceutically acceptable salt, solvate, hydrate, geometrical isomer, tautomer, optical isomer, isotopic derivative, polymorph, prodrug, or N-oxide thereof. An increase in citrulline in a biological sample is related to an increase in polyamine metabolism in a subject or a tissue or a cell of the subject (e.g., a neoplastic tissue or cell).

As used herein, the term "proline" refers to a compound having the CAS number 609-36-9 or 147-85-3 (L-proline), including pharmaceutically acceptable salts, solvates, hydrates, geometrical isomers, tautomers, optical isomers, isotopic derivatives, polymorphs, prodrugs, or N-oxides thereof. An increase in proline in a biological sample is related to an increase in amino acid metabolism in a subject or a tissue or a cell of the subject (e.g., a neoplastic tissue or cell).

As used herein, the term "glutamine" refers to a compound having the CAS number 56-85-9, including pharmaceutically acceptable salts, solvates, hydrates, geometrical isomers, tautomers, optical isomers, isotopic derivatives, polymorphs, prodrugs, or N-oxides thereof. An increase in glutamine in a biological sample is related to an increase in amino acid metabolism in a subject or a tissue or a cell of the subject (e.g., a neoplastic tissue or cell).

As used herein, the term "Nα-acetyllysine" refers to a compound having the CAS number 1946-82-3, including pharmaceutically acceptable salts, solvates, hydrates, geometrical isomers, tautomers, optical isomers, isotopic derivatives, polymorphs, prodrugs, or N-oxides thereof. An increase in Nα-acetyllysine in a biological sample is related to an increase in amino acid metabolism in a subject or a tissue or a cell of the subject (e.g., a neoplastic tissue or cell).

As used herein, the term "glutamic acid" refers to a compound having the CAS number CAS: 56-86-0, including pharmaceutically acceptable salts, solvates, hydrates, geometrical isomers, tautomers, optical isomers, isotopic derivatives, polymorphs, prodrugs, or N-oxides thereof. An increase in glutamic acid in a biological sample is related to an increase in amino acid metabolism in a subject or a tissue or a cell of the subject (e.g., a neoplastic tissue or cell).

As used herein, the term "threonine" refers to a compound having the CAS number CAS: 72-19-5, including pharmaceutically acceptable salts, solvates, hydrates, geometrical isomers, tautomers, optical isomers, isotopic derivatives, polymorphs, prodrugs, or N-oxides thereof. An increase in threonine in a biological sample is related to an increase in amino acid metabolism in a subject or a tissue or a cell of the subject (e.g., a neoplastic tissue or cell).

As used herein, the term "M264" refers to a novel metabolite that was identified as a biomarker for colorectal cancer in human urine samples. The metabolite has a molecular formulae $C_9H_{17}N_3O_6$ and gives rise to a protonated ion with m/z=264.12 in the ESI positive mode. The ion gives rise to fragments 132 and 90, characteristic fragments of creatine, in the ESI-MS/MS mode. The structure contains a creatine moiety with a ribofuranosyl ring attached to one of the guanidine nitrogens through C1 of the sugar. The IUPAC name of the compound is 2-{2-[(2R,3R,4S,5R)-3,4-dihydroxy-5-(hydroxymethyl)-oxolan-2-yl]-1-methylcarbamimidamido}acetic acid and the common name β-D-Ribofuranosylcreatine. The biosynthesis of the compound is expected to involve arginine metabolism, methylation and pentose phosphate pathway, which is also involved in nucleic acid biosynthesis.

By "agent" is meant any small molecule chemical compound, antibody, nucleic acid molecule, or polypeptide, or fragments thereof.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and may have less non-specific tissue binding of an intact antibody (Wahl et al., J. Nucl. Med. 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

By "biologic sample" is meant any tissue, cell, fluid, or other material derived from an organism.

By "clinical aggressiveness" is meant the severity of the neoplasia. Aggressive neoplasias are more likely to metastasize than less aggressive neoplasias. While conservative methods of treatment are appropriate for less aggressive neoplasias, more aggressive neoplasias require more aggressive therapeutic regimens.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "microarray" or "array" is meant to include a collection or panel of capture reagents arranged on a solid support (for example, a chip, plate, or bead).

By "neoplasia" is meant any disease that is caused by or results in inappropriately high levels of cell division, inappropriately low levels of apoptosis, or both. For example, cancer is an example of a neoplasia. Examples of cancers include, without limitation, prostate cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "reference" is meant a standard of comparison. For example, the level of one or more of asymmetric-dimethylarginine, symmetric-dimethylarginine, proline, glutamine, Nα-acetyllysine, xanthosine, inosine, deoxyuridine, thymidine, N1-acetylspermidine, N8-acetylspermidine, spermine, or carnitine present in a patient sample may be compared to the level of the compound(s) in a corresponding healthy cell or tissue or in a diseased cell or tissue (e.g., a cell or tissue derived from a subject having neoplasia). In quantitating the level of a compound of interest in a sample, the levels of the compound may be normalized to those of another compound whose levels are not related to a disease and/or are not expected to change (e.g., creatinine).

By "periodic" is meant at regular intervals. Periodic patient monitoring includes, for example, a schedule of tests that are administered daily, bi-weekly, bi-monthly, monthly, bi-annually, or annually.

By "severity of neoplasia" is meant the degree of pathology. The severity of a neoplasia increases, for example, as the stage or grade of the neoplasia increases.

By "Marker profile" is meant a characterization of the level of two or more compounds, analytes, or metabolites. For example, Marker profiles of the following groups of biomarkers are useful in characterizing neoplasia in the methods of the invention: asymmetric-dimethylarginine and symmetric-dimethylarginine, and optionally carnitine (methylation); proline, glutamine, Nα-acetyllysine (amino acid metabolism); xanthosine, inosine, deoxyuridine, thymidine (nucleic acid metabolism); and (polyamine metabolism); or a combination thereof.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "specifically binds" is meant an affinity agent (e.g., an antibody) that recognizes and binds a compound or agent of interest (e.g., a biomarker), but which does not substantially recognize and bind other molecules in a sample, for example, a biological sample.

As used herein, the terms "prevent," "preventing," "prevention," "prophylactic treatment," and the like, refer to reducing the probability of developing a disease or condition in a subject, who does not have, but is at risk of or susceptible to developing a disease or condition, e.g., neoplasia.

As used herein, the terms "treat," treating," "treatment," and the like refer to reducing or ameliorating a disease or condition, e.g., neoplasia, and/or symptoms associated therewith. It will be appreciated that, although not precluded, treating a disease or condition does not require that the disease, condition, or symptoms associated therewith be completely eliminated.

As used herein, the terms "comprises," "comprising," "containing," "having" and the like can have the meaning ascribed to them in U.S. patent law and can mean "includes," "including," and the like. The term "including" is used herein to mean, and is used interchangeably with, the phrase "including but not limited to." The terms "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. Unless specifically stated or obvious from context, as used herein, the term "or" is understood to be inclusive. Any compounds, compositions, or methods provided herein can be combined with one or more of any of the other compositions and methods provided herein.

DESCRIPTION OF THE DRAWINGS

FIG. 1A shows a representative picture of longitudinally opened intestine of APC$^{Min/+}$ and wild-type mice. Red arrows indicate tumor and polyps in the mutant. FIG. 1B is a graph of absolute body weight profile of wild-type (dotted line) and APC$^{Min/+}$ (solid line) mice during the study. There was no significant difference in body weight of wild-type and APC$^{Min/+}$ mice. All values presented as mean±SEM. FIG. 1C is a graph of box plots for alanine aminotransferase (ALT) and aspartate aminotransferase (AST) levels in wild-type and APC$^{Min/+}$ serum.

FIG. 2A is a scores scatter plot for principal components analysis (PCA) of total ion count (TIC)-normalized data obtained from UPLC-HILIC-ESI-MS analysis urine samples at five months in negative ionization mode. FIG. 2B is a scores scatter plot for principal components analysis (PCA) of creatinine-normalized data obtained from UPLC-HILIC-ESI-MS analysis urine samples at five months in negative ionization mode. FIG. 2C is a graph showing the longitudinal variation in the creatinine-normalized urinary excretion of glutamine in wild-type and APC$^{Min/+}$ mice is shown by dotted and solid lines, respectively. FIG. 2D is a graph showing the longitudinal variation in the creatinine-normalized urinary excretion of proline in wild-type and APC$^{Min/+}$ mice is shown by dotted and solid lines, respectively. FIG. 2E is a graph showing the longitudinal variation in the creatinine-normalized urinary excretion of Nα-acetyllysine in wild-type and APC$^{Min/+}$ mice is shown by dotted and solid lines, respectively. FIG. 2F is a graph showing the longitudinal variation in the creatinine-normalized urinary excretion of carnitine in wild-type and APC$^{Min/+}$ mice is shown by dotted and solid lines, respectively. The statistical significance of the difference in metabolite concentrations were calculated by two-tailed Mann-Whitney test with 95% confidence interval. P values <0.05, <0.01 and <0.005 are indicated by '*', '' and '*', respectively. All values are presented as mean±SEM.

FIG. 3A is a scores scatter plot for unsupervised principal components analysis (PCA) of creatinine-normalized UPLC-RP-ESIMS positive ionization mode data (0.1-1.3 mins) obtained from urine samples collected at six months. FIG. 3B is a scores scatter plot for orthogonal projections to latent structures (OPLS) analysis of creatinine-normalized data obtained from UPLC-HILIC-ESIMS analysis of urine samples collected at five months in negative ionization mode. FIG. 3C is a scores scatter plot for orthogonal projections to latent structures (OPLS) analysis of creatinine-normalized obtained from UPLC-RP-ESIMS analysis of urine samples collected at six months in positive ionization mode. FIG. 3D is a loadings S-plot of the ions from OPLS analysis of creatinine-normalized data obtained from UPLC-HILIC-ESIMS analysis of urine samples collected at five months in negative ionization mode. Distance from the origin along the Y-axis is commensurate with the contribution of the ion to separation of wild-type and mutant animals and that along the X-axis is commensurate with the abundance of the ion in the chromatogram. Ions in the upper right quadrant (shown in red box) represent ions elevated in APC$^{Min/+}$ urine and those in the bottom left quadrant (shown in green box) represent ions reduced in APC$^{Min/+}$ compared to their wild-type.

FIG. 4A is a graph showing the longitudinal variation in the creatinine-normalized urinary excretion of symmetric-dimethylarginine in wild-type and APC$^{Min/+}$ mice is shown by dotted and solid lines, respectively. FIG. 4B is a graph showing the longitudinal variation in the creatinine-normalized urinary excretion of asymmetric-dimethylarginine in wild-type and APC$^{Min/+}$ mice is shown by dotted and solid lines, respectively. FIG. 4C is a graph showing the longitudinal variation in the creatinine-normalized urinary excretion of citrulline in wild-type and APC$^{Min/+}$ mice is shown by dotted and solid lines, respectively. FIG. 4D is a graph showing the longitudinal variation in the creatinine-normalized urinary excretion of spermine in wild-type and APC$^{Min/+}$ mice is shown by dotted and solid lines, respectively. FIG. 4E is a graph showing the longitudinal variation in the creatinine-normalized urinary excretion of N1-acetylspermidine in wild-type and APC$^{Min/+}$ mice is shown by dotted and solid lines, respectively. FIG. 4F is a graph showing the longitudinal variation in the creatinine-normalized urinary excretion of N8-acetylspermidine in wild-type and APC$^{Min/+}$ mice is shown by dotted and solid lines, respectively. The statistical significance of the difference in metabolite concentrations were calculated by two-tailed Mann-Whitney test with 95% confidence interval. P values <0.05, <0.01 and <0.005 are indicated by '*', '' and '*', respectively. All values are presented as mean±SEM.

FIG. 5A is a graph showing longitudinal variation in the creatinine-normalized excretion of ornithine in the wild-type and APC$^{Min/+}$ mice in discovery set is shown by dotted and solid lines, respectively. All values shown as mean±SEM and '**' indicate P value <0.01. FIG. 5B is a graph of box plots for urinary excretion of N-acetyllysine, citrulline, thymidine, deoxyuridine, cytidine and xanthine in validation cohort. All statistical significances were calculated by two-tailed Mann-Whitney test with 95% confidence interval.

FIG. 6A is a is a graph showing longitudinal variation in the creatinine-normalized urinary excretion of xanthosine in wild-type and APC$^{Min/+}$ mice is shown by dotted and solid lines, respectively. FIG. 6B is a is a graph showing longitudinal variation in the creatinine-normalized urinary excretion of inosine in wild-type and APC$^{Min/+}$ mice is shown by dotted and solid lines, respectively. FIG. 6C is a is a graph showing longitudinal variation in the creatinine-normalized urinary excretion of xanthine in wild-type and APC$^{Min/+}$ mice is shown by dotted and solid lines, respectively. FIG. 6D is a is a graph showing longitudinal variation in the creatinine-normalized urinary excretion of cytidine in wild-type and APC$^{Min/+}$ mice is shown by dotted and solid lines, respectively. FIG. 6E is a is a graph showing longitudinal variation in the creatinine-normalized urinary excretion of deoxyuridine in wild-type and APC$^{Min/+}$ mice is shown by dotted and solid lines, respectively. FIG. 6F is a is a graph showing longitudinal variation in the creatinine-normalized urinary excretion of thymidine in wild-type and APC$^{Min/+}$ mice is shown by dotted and solid lines, respectively. The statistical significance of the difference in metabolite concentrations were calculated by two-tailed Mann-Whitney test with 95% confidence interval. P values <0.05, <0.01 and <0.005 are indicated by '*', '' and '*', respectively. All values are presented as mean±SEM.

FIG. 7A is a graph of box plots for creatinine-normalized concentrations of carnitine, glutamine, N1-acetylspermidine, N8-acetylspermidine, proline, asymmetric-dimethylarginine, symmetric-dimethylarginine, spermine, xanthosine and inosine in age-matched (six month old) non-littermate healthy control (wild-type) and tumor-bearing (APC$^{Min/+}$) animals. FIG. 7B is a graph of the receiver operating characteristic (ROC)

curve for tumor diagnosis using biomarkers related to amino acid metabolism (proline, glutamine and Nα-acetyllysine). FIG. 7C is a graph of the receiver operating characteristic (ROC) curve for tumor diagnosis using biomarkers related to polyamine metabolism (N1-acetylspermidine, N8-acetylspermidine and spermine). FIG. 7D is a graph of the receiver operating characteristic (ROC) curve for tumor diagnosis using biomarkers related to nucleic acid metabolism (xanthosine, inosine, deoxyuridine and thymidine). FIG. 7E is a graph of the receiver operating characteristic (ROC) curve for tumor diagnosis using biomarkers related to methylation (symmetric-dimethylarginine, asymmetric-dimethylarginine and carnitine). Area under the ROC curve (AUCROC) and accuracy is shown for each plot.

FIG. 8A depicts graphs of metabolites related to amino acid metabolism. FIG. 8B depicts graphs of metabolites related to polyamine metabolism. FIG. 8C depicts graphs of metabolites related to nucleic acid metabolism. FIG. 8D depicts graphs of metabolites related to methylation.

FIGS. 9A-9D depict analysis of individual metabolic urinary biomarkers. FIG. 9A depicts ROC curves for individual metabolites related to amino acid metabolism. FIG. 9B depicts ROC curves for individual metabolites related to polyamine metabolism. FIG. 9C depicts ROC curves for individual metabolites related to nucleic acid metabolism. FIG. 9D depicts ROC curves for individual metabolites related to methylation. The area under the curve (AUCROC) and accuracy for each metabolite is mentioned. See Table 1 for details on their diagnostic capability.

FIG. 10A is a heat-map showing distinct metabolomic trait associated with $APC^{Min/+}$ mice compared to wild-type. FIG. 10B shows that hierarchical clustering using the metabolite panel shows correct classification of all except one wild-type and one mutant mouse.

FIG. 11A depicts ROC curves for individual biomarker panels for detection of subjects prone to tumorigenesis (mutants) at five months in the longitudinal discovery cohort. FIG. 11B depicts ROC curves for a combination of biomarker panels for detection of subjects prone to tumorigenesis (mutants) at five months in the longitudinal discovery cohort. The area under the curve (AUCROC) and accuracy for each metabolic panel is mentioned. Carnitine had to be removed from the methylation panel as it perfectly identified mutants with a cut off value of 42.56 μmol/mmol creatinine.

FIG. 12A depicts ROC curves for individual biomarker panels for detection of subjects prone to tumorigenesis (mutants) at four months in the longitudinal discovery cohort. FIG. 12B depicts ROC curves for a combination of biomarker panels for detection of subjects prone to tumorigenesis (mutants) at four months in the longitudinal discovery cohort. The area under the curve (AUCROC) and accuracy for each metabolic panel is mentioned.

FIG. 13A depicts ROC curves for individual biomarker panels for detection of subjects prone to tumorigenesis (mutants) at three months in the longitudinal discovery cohort. FIG. 13B depicts ROC curves for a combination of biomarker panels for detection of subjects prone to tumorigenesis (mutants) at three months in the longitudinal discovery cohort. The area under the curve (AUCROC) and accuracy for each metabolic panel is mentioned.

FIG. 14A depicts ROC curves for individual biomarker panels for detection of subjects prone to tumorigenesis (mutants) at two months in the longitudinal discovery cohort. FIG. 14B depicts ROC curves for a combination of biomarker panels for detection of subjects prone to tumorigenesis (mutants) at two months in the longitudinal discovery cohort. The area under the curve (AUCROC) and accuracy for each metabolic panel is mentioned.

FIGS. 15A-15D depict the effect of colorectal tumorigenesis on tissue metabolome. FIG. 15A depicts graphs of box plots showing relative abundance of metabolites related to amino acid metabolism in normal colon mucosa (wild type) and colon tumor ($APC^{Min/+}$) tissue. FIG. 15B depicts graphs of box plots showing relative abundance of metabolites related to polyamine metabolism in normal colon mucosa (wild type) and colon tumor ($APC^{Min/+}$) tissue. FIG. 15C depicts graphs of box plots showing relative abundance of metabolites related to nucleic acid metabolism in normal colon mucosa (wild type) and colon tumor ($APC^{Min/+}$) tissue. FIG. 15D depicts graphs of box plots showing relative abundance of metabolites related to methylation in normal colon mucosa (wild type) and colon tumor ($APC^{Min/+}$) tissue. The abundance of proline, glutamine, glutamic acid, threonine, arginine, citrulline, ornithine, N1-acetylspermidine, thymidine, ATP, dimethylarginine and carnitine were elevated while those of xanthine and inosine were reduced. All values presented as fold-change with respect to the abundance of the metabolite in the normal colon epithelium. Statistical significance was calculated by two-tailed Mann-Whitney test with 95% confidence interval.

FIG. 16A is a graph of the expression of genes involved in amino acid biosynthesis are shown as fold change with respect gene expression in normal colon mucosa. FIG. 16B is a graph of the expression of genes involved in purine metabolism are shown as fold change with respect gene expression in normal colon mucosa. FIG. 16C is a graph of the expression of genes involved in pyrimidine metabolism are shown as fold change with respect gene expression in normal colon mucosa. FIG. 16D is a graph of the expression of genes involved in polyamine metabolism are shown as fold change with respect gene expression in normal colon mucosa. FIG. 16E is a graph of the expression of genes involved in methylation are shown as fold change with respect gene expression in normal colon mucosa. Statistical significance was calculated by two-tailed Mann-Whitney test with 95% confidence interval with '#', '$' and '*' indicating P values <0.05, <0.01 and <0.005, respectively.

FIG. 20A shows the molecular formula, IUPAC name and structure of the compound that would be commonly referred to as β-D-Ribofuranosylcreatine. FIG. 20B shows the creatinine-normalized relative abundance of the metabolite in control (N=10) and patient (N=10) urine samples. Statistical significance was calculated by two-tailed Mann-Whitney test with 95% confidence interval. FIG. 20C shows the ROC curve for detection of colorectal cancer using the metabolite.

FIG. 21A shows metabolic pathways captured by metabolomic and transcriptomic analysis in this study with metabolite names in red, black or blue indicating increase, no change or decrease, respectively, in abundance in $APC^{Min/+}$ tumor tissue. '*' indicates that the metabolite was significantly elevated in human tumor tissues. Solid red, black or blue boxes indicate that creatinine-normalized excretion of the metabolite was elevated, unchanged or depleted, respectively, in urine of the $Apc^{Min/+}$ mice. Dotted box indicates that the metabolite was either not detected or monitored in $Apc^{Min/+}$ urine. FA, Ac-CoA, Nα-Ac Lysine, OAA, α-KG, PRRP, SAH, SAM, MTA, SAMA, ADMA, SDMA, NMMA, N1-AcS and N8-AcS represent, fatty acid, acetyl coenzyme A, Nα acetyllysine, oxaloacetic acid, α-ketoglutaric acid, 5-phosphoribosyl 1-pyrophosphate, S-adenosylhomocysteine, S-adenosylmethionine, S-methyl-5-thioadenosine, S-adenosylmethioninamine, asymmetric-dimethylarginine, symmetric-dimethylarginine, N-monomethylarginine, N1-acetylspermidine and N8-acetylspermidine, respectively. Arrows indicate pathways of conversion of metabolites with solid and dotted lines indicating the involvement of single and multiple reactions, respectively. Red, black or blue colors indicate upregulation, no change or downregulation of expression of genes encoding enzymes involved in these pathways in $Apc^{Min/+}$ tumor tissue compared to normal colon mucosa, respectively. Dash-dotted arrows indicate pathways for biosynthesis of essential amino acids (such as threonine and lysine) that are unannotated in human and mouse. FIG. 21B shows the origin and utility of biomarkers of metabolic reprogramming in early noninvasive diagnosis.

DETAILED DESCRIPTION OF THE INVENTION

Figure 1:
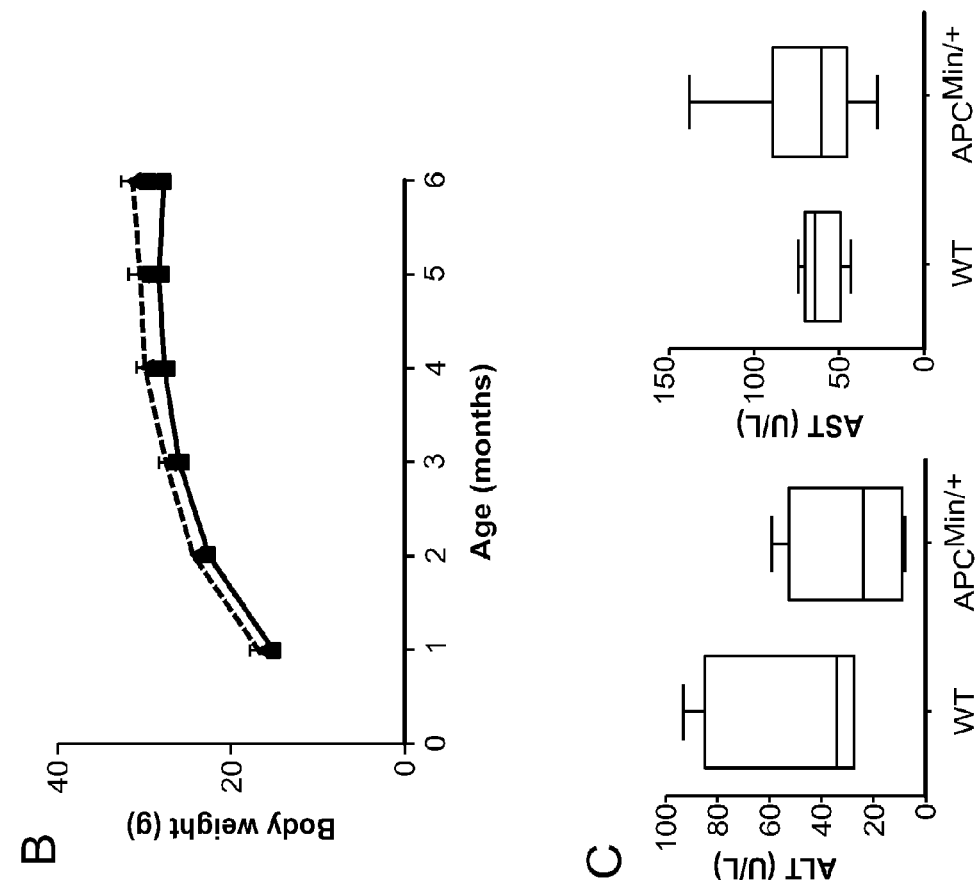
FIGS. 1A-1C depict the characterization of APC$^{Min/+}$ and wild-type mice.
Figure 1:
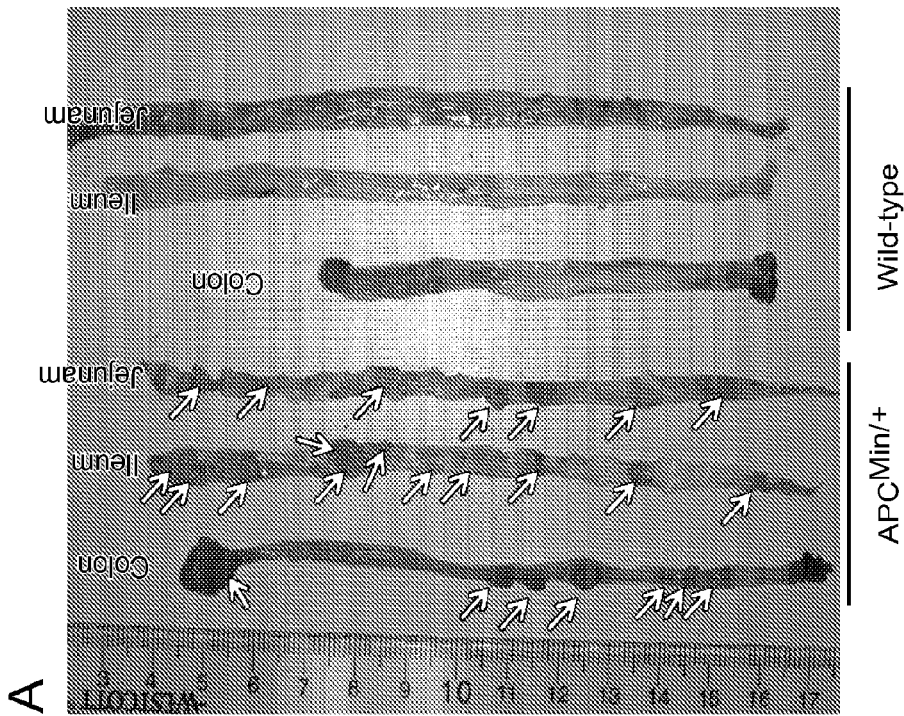

The invention features compositions and methods that are useful for the diagnosis, treatment and prevention of neoplasia, including colorectal cancer, as well as to determine subject prognosis and aid in treatment selection.

As detailed herein, metabolomic and transcriptomic analysis revealed changes in amino acid, nucleic acid, polyamine metabolism and methylation (e.g. protein methylation, DNA methylation) in tumor tissue. This invention is based, at least in part, on the discovery that the following groups or panels of biomarkers are useful and effective for identifying a subject as having or having a propensity to develop neoplasia (e.g., colorectal cancer, small intestine cancer, duodenal cancer, gastric cancer, pancreatic cancer, liver cancer, esophageal cancer, ovarian cancer, prostate cancer, uterine cancer, breast cancer, thyroid cancer and melanoma): biomarkers related to methylation; biomarkers related to nucleic acid metabolism; biomarkers related to urea cycle and polyamine metabolism; and biomarkers related to amino acid metabolism.

In particular, the biomarkers related to methylation include asymmetric-dimethylarginine, symmetric-dimethylarginine, carnitine, methionine, dimethylglycine, and betaine; the biomarkers related to nucleic acid metabolism include xanthosine, inosine, deoxyuridine, thymidine, deoxycytidine, cytosine, hypoxanthine, xanthine, uracil, guanosine, and adenosine; the biomarkers related to urea cycle and polyamine metabolism include N1-acetylspermidine, N8-acetylspermidine, spermine, arginine ornithine, and citrulline; and the biomarkers related to amino acid metabolism include proline, glutamine, glutamic acid, threonine, and Nα-acetyllysine.

Also contemplated by the present invention is the biomarker M264 as useful and effective for identifying a subject as having or having a propensity to develop neoplasia.

Changes in the urinary metabolome were found to be in concert with these metabolomic and transcriptomic changes in tumor tissue and, consequently, helped to correctly distinguish healthy and tumor-bearing animals. The consistency of longitudinal trait of simultaneous deregulation of these pathways during tumorigenesis resulted in highly accurate and early prediction of subjects at risk of developing colorectal cancer in this mouse model.

The results described herein revealed a concerted deregulation of epigenetic, transcriptional, post-translational and metabolic events associated with tumorigenesis in $APC^{Min/+}$ mice. Coordinate reprogramming of cellular metabolism during tumorigeneis is reflected in the urine metabolome. In particular, progressive elevation of symmetric- and asymmetric-dimethylarginine in urine of animals as a reflection of hyperactive methylation machinery is a novel observation in the context of colorectal cancer. The ability of urinary metabolites to prospectively identify animals that would eventually develop tumor, indicate a combined panel of urinary biomarkers representing synchronized deregulation of amino acid, nucleic acid, polyamine metabolism and methylation may provide a powerful high-throughput noninvasive method for screening as well as early diagnosis of colorectal cancer.

Accordingly, the invention provides for methods and kits that are useful in the diagnosis, treatment, and prevention of neoplasia, as well as for characterizing neoplasia to determine subject prognosis and aid in treatment selection. The invention further provides methods and kits for monitoring a patient identified as having neoplasia.

Diagnostics and Diagnostic Assays

The present invention features diagnostic assays for the detection of neoplasia, including colorectal cancer. In embodiments, the level of a biomarker(s) is measured in a subject sample and used to characterize neoplasia or the propensity to develop neoplasia. In particular embodiments, the levels of a group of methylation biomarkers are measured including at least asymmetric-dimethylarginine and symmetric-dimethylarginine, and optionally carnitine. In additional or alternative embodiments, the levels of biomarkers are measured from one or more of the following groups: biomarkers related to methylation; biomarkers related to nucleic acid metabolism; biomarkers related to urea cycle and polyamine metabolism; and biomarkers related to amino acid metabolism.

In particular, the biomarkers related to methylation include asymmetric-dimethylarginine, symmetric-dimethylarginine, carnitine, methionine, dimethylglycine, and betaine; the biomarkers related to nucleic acid metabolism include xanthosine, inosine, deoxyuridine, thymidine, deoxycytidine, cytosine, hypoxanthine, xanthine, uracil, guanosine, and adenosine; the biomarkers related to urea cycle and polyamine metabolism include N1-acetylspermidine, N8-acetylspermidine, spermine, arginine ornithine, and citrulline; and the biomarkers related to amino acid metabolism include proline, glutamine, glutamic acid, threonine, and Nα-acetyllysine. M264 (β-D-Ribofuranosylcreatine) biomarker is also contremplated in the diagnostic assays described herein.

Biological samples include tissue samples (e.g., cell samples, biopsy samples, and the like) and bodily fluids, including, but not limited to, urine, blood, blood serum, plasma, bile, fecal aspirate, intestinal aspirate, cerebrospinal fluid and saliva. Samples can optionally be treated to enrich for the biomarker(s) using enrichment and separation methods well known in the art.

Elevated levels of the biomarker(s) are considered a positive indicator of neoplasia. In general, an increase in the levels of one or more biomarkers related to methylation; biomarkers related to nucleic acid metabolism; biomarkers related to urea cycle and polyamine metabolism; biomarkers related to amino acid metabolism and M264 is indicative of neoplasia or the propensity to develop neoplasia.

In particular, an increase in the levels of one or more biomarkers related to methylation including asymmetric-dimethylarginine, symmetric-dimethylarginine, carnitine, methionine, dimethylglycine, and betaine; the biomarkers related to nucleic acid metabolism including xanthosine, inosine, deoxyuridine, thymidine, deoxycytidine, cytosine, hypoxanthine, xanthine, uracil, guanosine, and adenosine; the biomarkers related to urea cycle and polyamine metabolism including N1-acetylspermidine, N8-acetylspermidine, spermine, arginine ornithine, and citrulline; and the biomarkers related to amino acid metabolism including proline, glutamine, glutamic acid, threonine, Nα-acetyllysine and M264 is indicative of neoplasia or the propensity to develop neoplasia.

Elevated levels of the biomarker carnitine in tissue samples and reduced levels of the biomarker carnitine in biological fluid (e.g. urine) is indicative of neoplasia or the propensity to develop neoplasia. The increase or decrease in biomarker levels may be by at least about 10%, 25%, 50%, 75%, 90% or more. The increase or decrease in biomarker levels may be by at least about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 55, 60, 65, 70, 75, 80, 85, 90, 95-fold or more.

In embodiments, multiple biomarkers are measured (e.g., asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism). Additionally, one or more additional neoplasia biomarkers that are known in the art, (e.g., an APC variant associated with colon cancer).

In a particular embodiment, levels of the M264 biomarker are measured.

The use of multiple biomarkers increases the predictive value of the test and provides greater utility in diagnosis, toxicology, patient stratification and patient monitoring. The process called "Pattern recognition" detects the patterns formed by multiple biomarkers greatly improves the sensitivity and specificity of the diagnostic assay for predictive medicine. Subtle variations in data from clinical samples indicate that certain patterns of biomarkers can predict phenotypes such as the presence or absence of a certain disease, a particular stage of disease-progression, or a positive or adverse response to drug treatments.

Detection of an alteration relative to a reference sample (e.g., normal sample) can be used as a diagnostic indicator of neoplasia or colorectal cancer. In embodiments, the invention provides methods for identifying a subject as having or having a propensity to develop neoplasia or colorectal cancer. In related embodiments, the methods involve detecting the levels of one or more groups or panels of biomarkers as follows: asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or a combination thereof as specified herein, in a sample obtained from the subject. In embodiments, the methods involve comparing the level of the biomarker to a reference. In embodiments, the methods involve identifying the subject as having or having a propensity to develop neoplasia or colorectal cancer when the level of the biomarker is increased relative to the reference.

In embodiments, the invention provides methods for identifying neoplasia or colorectal cancer in a subject. In related embodiments, the methods involve detecting the levels of one or more groups or panels of biomarkers as follows: asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or a combination thereof as specified herein, in a sample obtained from the subject. In embodiments, the methods involve comparing the level of the biomarker to a reference. In embodiments, the methods involve identifying neoplasia or colorectal cancer in the subject when the level of the biomarker is increased relative to the reference.

In embodiments, the invention provides methods for characterizing the stage of neoplasia in a subject. In related embodiments, the methods involve detecting the levels of one or more groups or panels of biomarkers as follows: asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or a combination thereof as specified herein, in a sample obtained from the subject. In embodiments, the methods involve comparing the level of the biomarker to a reference. In embodiments, the methods involve identifying the subject as having a later stage of neoplasia when there is an increase in the level of the biomarker relative to the reference.

In embodiments, the invention provides methods for determining the prognosis of neoplasia in a subject. In related embodiments, the methods involve detecting the levels of one or more groups or panels of biomarkers as follows: a symmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or a combination thereof as specified herein in a sample obtained from the subject. In embodiments, the methods involve comparing the level of the biomarker to a reference. In embodiments, the methods involve identifying the subject as having a poor prognosis when there is an increase in the level of the biomarker relative to the reference.

In embodiments, the invention provides methods for characterizing the degree of lipid accumulation during the early stage of neoplasia in a subject. In related embodiments, the methods involve detecting the level s of one or more groups or panels of biomarkers as follows: asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or a combination thereof as specified herein in a sample obtained from the subject. In embodiments, the methods involve comparing the level of the biomarker to a reference. In embodiments, the methods involve identifying the subject as having a higher level of lipid accumulation during the early stage of neoplasia when there is an increase in the level of the biomarker relative to the reference.

In embodiments, the invention provides methods for monitoring neoplasia therapy in a subject. In related embodiments, the methods involve detecting the levels of one or more groups or panels of biomarkers as follows: asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or a combination thereof as specified herein in a sample obtained from the subject. In embodiments, the methods involve comparing the level of the biomarker to a reference. In embodiments, the methods involve identifying the therapy as effective when there is a decrease in the level of the biomarker relative to the reference.

In embodiments, the invention provides methods for detecting an agent's therapeutic efficacy in a subject having neoplasia. In related embodiments, the methods involve detecting an alteration in the levels of one or more groups or panels of biomarkers as follows: asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or a combination thereof as specified herein, in a sample obtained from the subject. In embodiments, the methods involve comparing the level of the biomarker to a reference (e.g., a patient sample taken at an earlier time point or prior to treatment). In embodiments, the methods involve identifying the agent as having therapeutic efficacy in the subject when there is a decrease in the level. In embodiments, the methods involve identifying the agent as lacking therapeutic efficacy in the subject when there maintenance or increase in the level.

In embodiments, the level of the biomarker(s) is measured on at least two different occasions and an alteration in the levels as compared to normal reference levels over time is used as an indicator of neoplasia, including colorectal cancer. The level of the biomarker(s) in a sample from a subject (e.g., bodily fluids such as blood, blood serum, plasma, bile, fecal aspirate, intestinal aspirate, cerebrospinal fluid, saliva, and urine) of a subject having neoplasia or the propensity to develop such a condition may be altered by as little as 10%, 20%, 30%, or 40%, or by as much as 50%, 60%, 70%, 80%, or 90% or more relative to the level of such biomarker(s) in a normal control. In embodiments, a subject sample is collected prior to the onset of symptoms of neoplasia. In embodiments, a subject sample is collected after the onset of symptoms of neoplasia. In embodiments, a subject sample is collected while the subject is undergoing treatment for neoplasia The diagnostic methods described herein can be used individually or in combination with any other diagnostic method described herein or well known in the art for a more accurate diagnosis of the presence or severity of neoplasia. The diagnostic methods described herein can also be used to monitor and manage neoplasia, including colorectal cancer.

As indicated above, the invention provides methods for aiding an neoplasia diagnosis using one or more groups or panels of biomarkers as follows: asymmetric-dimethylarginine, symmetric-dimethylarginine, carnitine, methionine, dimethylglycine, and betaine (methylation); proline, glutamine, glutamic acid, threonine, and Nα-acetyllysine (amino acid metabolism); xanthosine, inosine, deoxyuridine, thymidine, deoxycytidine, cytosine, hypoxanthine, xanthine, uracil, guanosine, and adenosine (nucleic acid metabolism); N1-acetylspermidine, N8-acetylspermidine, spermine, arginine ornithine, and citrulline (urea cycle and polyamine metabolism); or any combination of the recited biomarkers. These biomarker(s) can be used alone, in combination with other biomarkers in any set, or with entirely different markers in aiding neoplasia diagnosis. The markers are differentially present in samples of a neoplasia patient and a normal subject in whom neoplasia is undetectable. Therefore, detection of one or more of these biomarkers in a person would provide useful information regarding the probability that the person may have neoplasia or regarding the stage of neoplasia progression.

The detection of the biomarker(s) is then correlated with a probable diagnosis of neoplasia. In embodiments, the detection of the mere presence of a biomarker, without quantifying the amount thereof, is useful and can be correlated with a probable diagnosis of neoplasia. The measurement of biomarkers may also involve quantifying the markers to correlate the detection of markers with a probable diagnosis of neoplasia. Thus, if the amount of the biomarkers detected in a subject being tested is different compared to a control amount (e.g., higher than the control), then the subject being tested has a higher probability of having neoplasia.

The correlation may take into account the amount of the biomarker(s) in the sample compared to a control amount of biomarker(s) (e.g., in normal subjects or in non-neoplasia subjects such as where neoplasia is undetectable). A control can be, e.g., the average or median amount of the biomarker(s) present in comparable samples of normal subjects in normal subjects or in non-neoplasia subjects such as where neoplasia is undetectable. The control amount is measured under the same or substantially similar experimental conditions as in measuring the test amount. As a result, the control can be employed as a reference standard, where the normal (non-neoplasia) phenotype is known, and each result can be compared to that standard (e.g., a standardized curve for use), rather than re-running a control.

In some embodiments, the control is derived from the patient and provides a reference level of the patient prior to, during, or after treatment for neoplasia.

Accordingly, a biomarker profile may be obtained from a subject sample and compared to a reference biomarker profile obtained from a reference population, so that it is possible to classify the subject as belonging to or not belonging to the reference population. The correlation may take into account the presence or absence of the biomarkers in a test sample and the frequency of detection of the same biomarkers in a control. The correlation may take into account both of such factors to facilitate determination of neoplasia status.

In certain embodiments of the methods of qualifying neoplasia status, the methods further comprise managing subject treatment based on the status. The invention also provides for such methods where the biomarker(s) are measured again after subject management. In these cases, the methods are used to monitor the status of neoplasia, e.g., response to neoplasia treatment, including improvement, maintenance, or progression of the disease.

A biomarker, individually, can be useful in aiding in the determination of neoplasia status. First, the selected biomarker is detected in a subject sample using well known methods, including, but not limited to, the methods described herein. Then, the result is compared with a control that distinguishes neoplasia status from non-neoplasia status. As is well understood in the art, the techniques can be adjusted to increase sensitivity or specificity of the diagnostic assay depending on the preference of the diagnostician.

While an individual biomarker is a useful diagnostic marker, in some instances, a combination of biomarkers provides greater predictive value than single markers alone. The detection of a plurality of biomarkers (or absence thereof, as the case may be) in a sample can increase the percentage of true positive and true negative diagnoses and decrease the percentage of false positive or false negative diagnoses. Thus, in embodiments, methods of the present invention comprise the measurement of more than one biomarker.

Colorectal Cancer

Colorectal cancer is the second leading cause of cancer mortality in United States and fourth worldwide. Although colorectal cancer has good therapeutic response at early stages, advanced stages are frequently associated with metastasis and poor prognosis. Regular screening and early diagnosis of the disease is pivotal to therapeutic success.

More than 80% of colorectal cancers arise from adenomatous polyps making this cancer amenable to screening. Diagnosis of cases of colorectal cancer through screening tends to occur 2-3 years before diagnosis of cases with symptoms. Screening has the potential to reduce colorectal cancer deaths by 60%.

Colorectal Cancer Staging

The most commonly used staging system for colorectal cancer is that of the American Joint Committee on Cancer (AJCC), or the TNM system. Older staging systems for colorectal cancer, such as the Dukes and Astler-Coller systems, are mentioned for comparison. The TNM system describes 3 key pieces of information: "T" describes how far the main (primary) tumor has grown into the wall of the intestine and whether it has grown into nearby areas; "N" describes the extent of spread to nearby (regional) lymph nodes. Lymph nodes are small bean-shaped collections of immune system cells that are important in fighting infections. "M" indicates whether the cancer has spread (metastasized) to other organs of the body. (Colorectal cancer can spread almost anywhere in the body, but the most common sites of spread are the liver and lungs). Numbers appearing after T, N, and M (0-4) indicate increasing severity.

T categories of colorectal cancer describe the extent of spread through the layers that form the wall of the colon and rectum. Tx: No description of the tumor's extent is possible because of incomplete information. Tis: The cancer is in the earliest stage (in situ); involves only the mucosa; and/or has not grown beyond the muscularis mucosa (inner muscle layer). T1: The cancer has grown through the muscularis mucosa and extends into the submucosa. T2: The cancer has grown through the submucosa and extends into the muscularis propria (thick outer muscle layer). T3: The cancer has grown through the muscularis propria and into the outermost layers of the colon or rectum but not through them. It has not reached any nearby organs or tissues. T4a: The cancer has grown through the serosa (also known as the visceral peritoneum), the outermost lining of the intestines. T4b: The cancer has grown through the wall of the colon or rectum and is attached to or invades into nearby tissues or organs.

N categories indicate whether or not the cancer has spread to nearby lymph nodes and, if so, how many lymph nodes are involved. Nx: No description of lymph node involvement is possible because of incomplete information. N0: No cancer in nearby lymph nodes. N1: Cancer cells are found in or near 1 to 3 nearby lymph nodes; small deposits of cancer cells are found in areas of fat near lymph nodes, but not in the lymph nodes themselves. N2: Cancer cells are found in 4 or more nearby lymph nodes M categories indicate whether or not the cancer has spread (metastasized) to distant organs, such as the liver, lungs, or distant lymph nodes. M0: No distant spread is seen. M1a: The cancer has spread to 1 distant organ or set of distant lymph nodes. M1b: The cancer has spread to more than 1 distant organ or set of distant lymph nodes, or it has spread to distant parts of the peritoneum (the lining of the abdominal cavity).

Information from T, N, and M categories is combined in a process called stage grouping. The stage is expressed in Roman numerals from stage I (the least advanced) to stage IV (the most advanced). Stage 0—Tis, N0, M0: The cancer is in the earliest stage; the cancer has not grown beyond the inner layer (mucosa) of the colon or rectum (carcinoma in situ or intramucosal carcinoma). Stage I—T1-T2, N0, M0: The cancer has grown through the muscularis mucosa into the submucosa (T1) or it may also have grown into the muscularis propria (T2); the cancer has not spread to nearby lymph nodes or distant sites. Stage IIA—T3, N0, M0: The cancer has grown into the outermost layers of the colon or rectum but has not gone through them (T3). The cancer has not reached nearby organs. The cancer has not yet spread to the nearby lymph nodes or distant sites. Stage IIB—T4a, N0, M0: The cancer has grown through the wall of the colon or rectum but has not grown into other nearby tissues or organs (T4a). The cancer has not yet spread to the nearby lymph nodes or distant sites. Stage IIC—T4b, N0, M0: The cancer has grown through the wall of the colon or rectum and is attached to or has grown into other nearby tissues or organs (T4b). The cancer has not yet spread to the nearby lymph nodes or distant sites. Stage IIIA—One of the following applies. T1-T2, N1, M0: The cancer has grown through the mucosa into the submucosa (T1) and it may also have grown into the muscularis propria (T2). The cancer has spread to 1 to 3 nearby lymph nodes (N1a/N1b) or into areas of fat near the lymph nodes but not the nodes themselves (N1c). It has not spread to distant sites. T1, N2a, M0: The cancer has grown through the mucosa into the submucosa (T1). It has spread to 4 to 6 nearby lymph nodes (N2a). The cancer has not spread to distant sites. Stage IIIB—One of the following applies. T3-T4a, N1, M0: The cancer has grown into the outermost layers of the colon or rectum (T3) or through the visceral peritoneum (T4a) but has not reached nearby organs. The cancer has spread to 1 to 3 nearby lymph nodes (N1a/N1b) or into areas of fat near the lymph nodes but not the nodes themselves (N1c). It has not spread to distant sites. T2-T3, N2a, M0: The cancer has grown into the muscularis propria (T2) or into the outermost layers of the colon or rectum (T3). The cancer has spread to 4 to 6 nearby lymph nodes (N2a). It has not spread to distant sites. T1-T2, N2b, M0: The cancer has grown through the mucosa into the submucosa (T1) or it may also have grown into the muscularis propria (T2). The cancer has spread to 7 or more nearby lymph nodes (N2b). The cancer has not spread to distant sites. Stage IIIC—One of the following applies. T4a, N2a, M0: The cancer has grown through the wall of the colon or rectum (including the visceral peritoneum) but has not reached nearby organs (T4a). The cancer has spread to 4 to 6 nearby lymph nodes (N2a). The cancer has not spread to distant sites. T3-T4a, N2b, M0: The cancer has grown into the outermost layers of the colon or rectum (T3) or through the visceral peritoneum (T4a) but has not reached nearby organs. The cancer has spread to 7 or more nearby lymph nodes (N2b). The cancer has not spread to distant sites. T4b, N1-N2, M0: The cancer has grown through the wall of the colon or rectum and is attached to or has grown into other nearby tissues or organs (T4b). The cancer has spread to at least one nearby lymph node or into areas of fat near the lymph nodes (N1 or N2). The cancer has not spread to distant sites. Stage IVA—Any T, Any N, M1a: The cancer may or may not have grown through the wall of the colon or rectum, and it may or may not have spread to nearby lymph nodes. The cancer has spread to 1 distant organ (such as the liver or lung) or set of lymph nodes (M1a). Stage IVB—Any T, Any N, M1b: The cancer may or may not have grown through the wall of the colon or rectum, and it may or may not have spread to nearby lymph nodes. The cancer has spread to more than 1 distant organ (such as the liver or lung) or set of lymph nodes, or it has spread to distant parts of the peritoneum (the lining of the abdominal cavity) (M1b).

Colorectal Cancer Grading

The grade of the cancer is another factor that can affect the outlook for survival. Grade is a description of how closely the cancer looks like normal colorectal tissue when seen under a microscope. The scale used for grading colorectal cancers goes from G1 (where the cancer looks much like normal colorectal tissue) to G4 (where the cancer looks very abnormal). The grades G2 and G3 fall somewhere in between. The grade is often simplified as either "low grade" (G1 or G2) or "high grade" (G3 or G4). Low-grade cancers tend to grow and spread more slowly than high-grade cancers. Most of the time, the outlook is better for low-grade cancers than it is for high-grade cancers of the same stage. Doctors sometimes use this distinction to help decide treatment selection (e.g., additional (adjuvant) treatment with chemotherapy after surgery).

Diagnosis of colorectal cancer is via tumor biopsy typically done during sigmoidoscopy or colonoscopy. The extent of the disease is then usually determined by a CT scan of the chest, abdomen and pelvis. There are other potential imaging test such as PET and MRI which may be used in certain cases. The three main screening tests are fecal occult blood testing, flexible sigmoidoscopy and colonoscopy. Of the three, only sigmoidoscopy can not screen the right side of the colon where 42% of malignancies are found. Virtual colonoscopy via a CT scan can detect cancers and large adenomas but is expensive, associated with radiation exposure, and can not remove any detected abnormal growths like standard colonoscopy can.

Fecal occult blood testing of the stool is typically recommended every two years and can be either guaiac based orimmunochemical. Medical societies recommend screening between the age of 50 and 75 years with sigmoidoscopy every 5 years and colonoscopy every 10 years. For those at high risk, screenings usually begin at around 40. For people with average risk who have had a high-quality colonoscopy with normal results, the American Gastroenterological Association does not recommend any type of screening in the 10 years following the colonoscopy. For people over 75 or those with a life expectancy of less than 10 years, screening is not recommended.

Metabolomics has the potential to be a useful tool for identification of changes in biochemical signature associated with pathogenesis. However, tissue metabolomics requires biopsy samples and is invasive. Urine metabolomics has been shown to be a powerful approach to identify noninvasive biomarkers for diagnosis. A number of metabolomic studies have actually shown that metabolite composition of the tissue as well as biofluids from colorectal cancer patients are different from that of healthy controls thus raising the hope for an alternative noninvasive method for screening, diagnosis and therapeutic monitoring. On the other hand, sensitivity of the metabolome to factors such as genetic composition, food and environment, warrants exploration of the mechanistic link between biofluid biomarkers and molecular signatures of tumor tissue to identify robust biomarkers of pathogenesis and high-fidelity target pathways. Moreover, there has been a general lack of studies investigating the mechanistic link between these biomarkers and changes in cancer tissue.

Longitudinal changes in population at risk (due to genetic or environmental predisposition) vis-à-vis healthy controls to find out consistent and progressive changes during tumorigenesis, which may also yield early biomarkers. Animal models have long provided a reasonably sound fundamental and translational bypass on human biology. In fact, a large volume of the molecular events associated with colorectal carcinogenesis has been derived from research on animal models such as APC$^{Min/+}$ mice. These animals harbor a mutation in an allele of the Adenomalous Polyposis Coli (APC) gene that causes familial adenomatous polyposis-associated colorectal cancer in humans. Mutations in the APC gene, which is involved in the Wnt-signaling pathway, are also frequently associated with sporadic colorectal cancer. The results herein describe, for the first time, a longitudinal trace of evolution in urinary metabolomic signature during colorectal carcinogenesis and detail a potential mechanistic link with transcriptomic and metabolomic changes in tumor tissue to identify potential high-throughput noninvasive biomarkers using APC$^{Min/+}$ mouse model.

Adenomatous Polyposis Coli (APC)

The most commonly mutated gene in all colorectal cancer is the APC gene, which produces the APC protein. The APC protein, which is a tumor suppressor gene, inhibits the accumulation of β-catenin protein. Without APC, β-catenin accumulates to high levels and translocates (moves) into the nucleus, binds to DNA, and activates the transcription of genes that are normally important for stem cell renewal and differentiation but when inappropriately expressed at high levels can cause cancer. While APC is mutated in most colon cancers, some cancers have mutations in other Wnt signaling pathway proteins. For example, such situations where Wnt signaling pathway proteins are mutated other than APC include mutations in β-catenin (CTNNB1) that block its degradation, resulting in increased β-catenin levels, or mutation(s) in other genes with function analogous to APC such as AXIN1, AXIN2, TCF7L2, or NKD1. Like colorectal cancer, APC and Wnt signaling pathway proteins may be mutated in other cancers including small intestine cancer, duodenal cancer, gastric cancer, pancreatic cancer, liver cancer, esophageal cancer, ovarian cancer, prostate cancer, uterine cancer, breast cancer, thyroid cancer or melanoma (Giles et al., Biochim. Biophys. Acta. 2003; 1653: 1-24).

The amino acid sequence of an exemplary human APC sequence (isoform B) is provided at GenBank Accession No. NP_000029, which is reproduced below:

```
   1 maassydqll kqvealkmen snlrqeledn snhltklete asnmkevlkq lqgsiedeam
  61 assgqidlle rlkelnldss nfpqvklrsk mslrsygsre gsvssrsgec spvpmgsfpr
 121 rgfvngsres tgyleeleke rsllladldk eekekdwyya qlqnltkrid slpltenfsl
 181 qtdmtrrqle yearqirvam esqlgtcqdm ekraqrriar iqqiekdilr irgllqsqat
 241 eaerssqnkh etgshdaerq negqgvgein matsgngqgs ttrmdhetas vlssssthsa
 301 prrltshlgt kvemvyslls mlgthdkddm srtllamsss qdscismrqs gclplliqll
 361 hgndkdsvll gnsrgskear arasaalhni ihsqpddkrg rreirvlhll eqiraycetc
 421 wewqeahepg mdqdknpmpa pvehqicpav cvlmklsfde ehrhamnelg glqaisellq
 481 vdcemygltn dhysitlrry agmaltnltf gdvankatlc smkgcmralv aqlksesedl
 541 qqviasvlrn lswradvnsk ktlrevgsvk almecalevk kestlksvls alwnlsahct
 601 enkadicavd galaflvgtl tyrsqtntla iiesgggilr nvssliatne dhrqilrenn
 661 clqtllqhlk shsltivsna cgtlwnlsar npkdqealwd mgavsmlknl ihskhkmiam
 721 gsaaalrnim anrpakykda nimspgsslp slhvrkqkal eaeldaqhls etfdnidnls
 781 pkashrskqr hkqslygdyv fdtnrhddnr sdnfhtgnmt vlspylnttv lpsssssrgs
 841 ldssrsekdr slerergigl gnyhpatenp gtsskrglqi sttaaqiakv meevsaihts
 901 qedrssgstt elhcvtdern alrrssaaht hsntynftks ensnrtcsmp yakleykrss
 961 ndslnsvsss dgygkrgqmk psiesysedd eskfcsygqy padlahkihs anhmddndge
1021 ldtpinyslk ysdeqlnsgr gspsqnerwa rpkhiiedei kqseqrqsrn qsttypvyte
1081 stddkhlkfq phfgqqecvs pyrargangs etnrvgshhg inqnvsqslc qeddyeddkp
1141 tnyserysee eqheeeerpt nysikyneek rhvdqpidys lkyatdipss qkqsfsfsks
1201 ssgqaskteh mssssentst pssnakrqng lhpssaqsrs gqpqkaatck vssinqetiq
1261 tycvedtpic fsrcsslssl ssaedeigcn qttqeadsan tlqiaeikek igtrsaedpv
1321 sevpavsqhp rtkssrlqgs slssesarnk avefssgaks psksgaqtpk sppehyvqet
```

-continued

```
1381 plmfsrctsv ssldsfesrs iassvqsepc sgmvsgiisp sdlpdspgqt mppsrsktpp
1441 pppqtaqtkr evpknkapta ekresgpkqa avnaavqrvq vlpdadtllh fatestpdgf
1501 scsssslsals ldepfiqkdv elrimppvqe ndngnetese qpkesnenqe keaektidse
1561 kdllddsddd dielleecii samptkssrk akkpaqtask lpppvarkps qlpvykllps
1621 qnrlqpqkhv sftpgddmpr vycvegtpin fstatslsdl tiesppnela agegvrggaq
1681 sgefekrdti ptegrstdea qggktssvti pelddnkaee gdilaecins ampkgkshkp
1741 frvkkimdqv gqasasssap nknqldgkkk kptspvkpip qnteyrtrvr knadsknnln
1801 aervfsdnkd skkqnlknns kvfndklpnn edrvrgsfaf dsphhytpie gtpycfsrnd
1861 slssldfddd dvdlsrekae lrkakenkes eakvtshtel tsnqqsankt qaiakqpinr
1921 gqpkpliqkq stfpqsskdi pdrgaatdek lqnfaientp vcfshnssls slsdidqenn
1981 nkenepiket eppdsqgeps kpqasgyapk sfhvedtpvc fsrnsslssl sidseddllq
2041 ecissampkk kkpsrlkgdn ekhsprnmgg ilgedltldl kdiqrpdseh glspdsenfd
2101 wkaiqegans ivsslhqaaa aaclsrqass dsdsilslks gislgspfhl tpdqeekpft
2161 snkgprilkp gekstletkk ieseskgikg gkkvykslit gkvrsnseis gqmkqplqan
2221 mpsisrgrtm ihipgvrnss sstspvskkg pplktpasks psegqtatts prgakpsvks
2281 elspvarqts qiggsskaps rsgsrdstps rpaqqplsrp iqspgrnsis pgrngisppn
2341 klsqlprtss pstastkssg sgkmsytspg rqmsqqnltk qtglsknass iprsesaskg
2401 lnqmnngnga nkkvelsrms stkssgsesd rserpvlvrq stfikeapsp tlrrkleesa
2461 sfeslspssr pasptrsqaq tpvlspslpd mslsthssvq aggwrklppn lsptieyndg
2521 rpakrhdiar shsespsrlp inrsgtwkre hskhssslpr vstwrrtgss ssilsasses
2581 sekaksedek hvnsisgtkq skenqvsakg twrkikenef sptnstsqtv ssgatngaes
2641 ktliyqmapa vsktedvwvr iedcpinnpr sgrsptgntp pvidsvseka npnikdskdn
2701 qakqnvgngs vpmrtvglen rlnsfiqvda pdqkgteikp gqnnpvpvse tnessivert
2761 pfsssssskh sspsgtvaar vtpfnynpsp rkssadstsa rpsqiptpvn nntkkrdskt
2821 dstessgtqs pkrhsgsylv tsv
```

APC is a 2843-amino acid polypeptide. The nucleotide sequence of human APC corresponds to nucleotides 86-8617 of the human APC mRNA transcript (variant 3) provided at GenBank Accession No. NM_000038.5, which is reproduced below:

```
  1 gtattggtgc agcccgccag ggtgtcactg gagacagaat ggaggtgctg ccggactcgg
 61 aaatgggtc caagggtagc caaggatggc tgcagcttca tatgatcagt tgttaaagca
121 agttgaggca ctgaagatgg agaactcaaa tcttcgacaa gagctagaag ataattccaa
181 tcatcttaca aaactggaaa ctgaggcatc taatatgaag gaagtactta acaactaca
241 aggaagtatt gaagatgaag ctatggcttc ttctggacag attgatttat tagagcgtct
301 taaagagctt aacttagata gcagtaattt ccctggagta aaactgcggt caaaaatgtc
361 cctccgttct tatggaagcc gggaaggatc tgtatcaagc cgttctggag agtgcagtcc
421 tgttcctatg ggttcatttc caagaagagg gtttgtaaat ggaaacagag aaagtactgg
481 atatttagaa gaacttgaga agagaggtc attgcttctt gctgatcttg acaaagaaga
541 aaaggaaaaa gactggtatt acgctcaact tcagaatctc actaaaagaa tagatagtct
601 tcctttaact gaaaattttt ccttacaaac agatatgacc agaaggcaat tggaatatga
```

-continued

```
 661 agcaaggcaa atcagagttg cgatggaaga caactaggt acctgccagg atatggaaaa
 721 acgagcacag cgaagaatag ccagaattca gcaaatcgaa aaggacatac ttcgtatacg
 781 acagctttta cagtcccaag caacagaagc agagaggtca tctcagaaca agcatgaaac
 841 cggctcatat gatgctgagc ggcagaatga aggtcaagga gtgggagaaa tcaacatggc
 901 aacttctggt aatggtcagg gttcaactac acgaatggac catgaaacag ccagtgtttt
 961 gagttctagt agcacacact ctgcacctcg aaggctgaca agtcatctgg aaccaaggt
1021 ggaaatggtg tattcattgt tgtcaatgct tggtactcat gataaggatg atatgtcgcg
1081 aactttgcta gctatgtcta gctcccaaga cagctgtata tccatgcgac agtctggatg
1141 tcttcctctc ctcatccagc ttttacatgg caatgacaaa gactctgtat tgttgggaaa
1201 ttcccggggc agtaaagagg ctcgggccag ggccagtgca gcactccaca acatcattca
1261 ctcacagcct gatgacaaga gaggcaggcg tgaaatccga gtccttcatc ttttggaaca
1321 gatacgcgct tactgtgaaa cctgttggga gtggcaggaa gctcatgaac caggcatgga
1381 ccaggacaaa aatccaatgc cagctcctgt tgaacatcag atctgtcctg ctgtgtgtgt
1441 tctaatgaaa ctttcatttg atgaagagca tagacatgca atgaatgaac tagggggact
1501 acaggccatt gcagaattat tgcaagtgga ctgtgaaatg tatgggctta ctaatgacca
1561 ctacagtatt acactaagac gatatgctgg aatggctttg acaaacttga cttttggaga
1621 tgtagccaac aaggctacgc tatgctctat gaaaggctgc atgagagcac ttgtggccca
1681 actaaaatct gaaagtgaag acttacagca ggttattgcg agtgttttga ggaatttgtc
1741 ttggcgagca gatgtaaata gtaaaaagac gttgcgagaa gttggaagtg tgaaagcatt
1801 gatggaatgt gctttagaag ttaaaaagga atcaaccctc aaaagcgtat tgagtgcctt
1861 atggaatttg tcagcacatt gcactgagaa taaagctgat atatgtgctg tagatggtgc
1921 acttgcattt ttggttggca ctcttactta ccggagccag acaaacactt tagccattat
1981 tgaaagtgga ggtgggatat tacggaatgt gtccagcttg atagctacaa atgaggacca
2041 caggcaaatc ctaagagaga acaactgtct acaaacttta ttacaacact taaaatctca
2101 tagtttgaca atagtcagta atgcatgtgg aactttgtgg aatctctcag caagaaatcc
2161 taaagaccag gaagcattat gggacatggg ggcagttagc atgctcaaga acctcattca
2221 ttcaaagcac aaaatgattg ctatgggaag tgctgcagct ttaaggaatc tcatggcaaa
2281 taggcctgcg aagtacaagg atgccaatat tatgtctcct ggctcaagct tgccatctct
2341 tcatgttagg aaacaaaaag ccctagaagc agaattagat gctcagcact tatcagaaac
2401 ttttgacaat atagacaatt taagtcccaa ggcatctcat cgtagtaagc agagacacaa
2461 gcaaagtctc tatggtgatt atgtttttga caccaatcga catgatgata ataggtcaga
2521 caatttaat actggcaaca tgactgtcct ttcaccatat ttgaatacta cagtgttacc
2581 cagctcctct tcatcaagag gaagcttaga tagttctcgt tctgaaaaag atagaagttt
2641 ggagagagaa cgcggaattg gtctaggcaa ctaccatcca gcaacagaaa atccaggaac
2701 ttcttcaaag cgaggtttgc agatctccac cactgcagcc cagattgcca aagtcatgga
2761 agaagtgtca gccattcata cctctcagga agacagaagt tctgggtcta ccactgaatt
2821 acattgtgtg acagatgaga gaaatgcact tagaagaagc tctgctgccc atacacattc
2881 aaacacttac aatttcacta agtcggaaaa ttcaaatagg acatgttcta tgccttatgc
2941 caaattagaa tacaagagat cttcaaatga tagtttaaat agtgtcagta gtagtgatgg
3001 ttatggtaaa agaggtcaaa tgaaaccctc gattgaatcc tattctgaag atgatgaaag
```

-continued

```
3061 taagttttgc agttatggtc aatacccagc cgacctagcc cataaaatac atagtgcaaa 3121 tcatatggat gataatgatg gagaactaga tacaccaata aattatagtc ttaaatattc 3181 agatgagcag ttgaactctg gaaggcaaag tccttcacag aatgaaagat gggcaagacc 3241 caaacacata atagaagata aataaaaaca aagtgagcaa agacaatcaa ggaatcaaag 3301 tacaacttat cctgtttata ctgagagcac tgatgataaa cacctcaagt tccaaccaca 3361 ttttggacag caggaatgtg tttctccata caggtcacgg ggagccaatg gttcagaaac 3421 aaatcgagtg ggttctaatc atggaattaa tcaaaatgta agccagtctt tgtgtcaaga 3481 agatgactat gaagatgata agcctaccaa ttatagtgaa cgttactctg aagaagaaca 3541 gcatgaagaa gaagagagac caacaaatta tagcataaaa tataatgaag agaacgtca 3601 tgtggatcag cctattgatt atagtttaaa atatgccaca gatattcctt catcacagaa 3661 acagtcattt tcattctcaa agagttcatc tggacaaagc agtaaaaccg aacatatgtc 3721 ttcaagcagt gagaatacgt ccacaccttc atctaatgcc aagaggcaga atcagctcca 3781 tccaagttct gcacagagta gaagtggtca gcctcaaaag gctgccactt gcaaagtttc 3841 ttctattaac caagaaacaa tacagactta ttgtgtagaa gatactccaa tatgtttttc 3901 aagatgtagt tcattatcat ctttgtcatc agctgaagat gaaataggat gtaatcagac 3961 gacacaggaa gcagattctg ctaatacccct gcaaatagca gaaataaaag aaaagattgg 4021 aactaggtca gctgaagatc ctgtgagcga agttccagca gtgtcacagc ccctagaac 4081 caaatccagc agactgcagg gttctagttt atcttcagaa tcagccaggc acaaagctgt 4141 tgaattttct tcaggagcga aatctccctc caaaagtggt gctcagacac ccaaaagtcc 4201 acctgaacac tatgttcagg agaccccact catgtttagc agatgtactt ctgtcagttc 4261 acttgatagt tttgagagtc gttcgattgc cagctccgtt cagagtgaac catgcagtgg 4321 aatggtaagt ggcattataa gccccagtga tcttccagat agccctggac aaaccatgcc 4381 accaagcaga agtaaaacac ctccaccacc tcctcaaaca gctcaaacca gcgagaagt 4441 acctaaaaat aaagcaccta ctgctgaaaa gagagagagt ggacctaagc aagctgcagt 4501 aaatgctgca gttcagaggg tccaggttct tccagatgct gatactttat tacattttgc 4561 cacggaaagt actccagatg gattttcttg ttcatccagc ctgagtgctc tgagcctcga 4621 tgagccattt atacagaaag atgtggaatt aagaataatg cctccagttc aggaaaatga 4681 caatgggaat gaaacagaat cagagcagcc taaagaatca atgaaaaacc aagagaaaga 4741 ggcagaaaaa actattgatt ctgaaaagga cctattagat gattcagatg atgatgatat 4801 tgaaatacta gaagaatgta ttatttctgc catgccaaca aagtcatcac gtaaagcaaa 4861 aaagccagcc cagactgctt caaaattacc tccacctgtg gcaaggaaac caagtcagct 4921 gcctgtgtac aaacttctac catcacaaaa caggttgcaa ccccaaaagc atgttagttt 4981 tacaccgggg gatgatatgc cacgggtgta ttgtgttgaa gggacaccta taaacttttc 5041 cacagctaca tctctaagtg atctaacaat cgaatcccct ccaaatgagt tagctgctgg 5101 agaaggagtt agaggagggg cacagtcagg tgaatttgaa aaacgagata ccattcctac 5161 agaaggcaga agtacagatg aggctcaagg aggaaaaacc tcatctgtaa ccatacctga 5221 attggatgac aataaagcag aggaaggtga tattcttgca gaatgcatta attctgctat 5281 gcccaaaggg aaagtcaca agcttttccg tgtgaaaaag ataatggacc aggtccagca 5341 agcatctgcg tcttcttctg cacccaacaa aaatcagtta gatggtaaga aaaagaaacc 5401 aacttcacca gtaaaaccta taccacaaaa tactgaatat aggacacgtg taagaaaaaa 5461 tgcagactca aaaaataatt taaatgctga gagagttttc tcagacaaca agattcaaa
```

-continued

```
5521 gaaacagaat tgaaaaata attccaaggt cttcaatgat aagctcccaa ataatgaaga
5581 tagagtcaga ggaagttttg cttttgattc acctcatcat tacacgccta ttgaaggaac
5641 tccttactgt ttttcacgaa atgattcttt gagttctcta gattttgatg atgatgatgt
5701 tgacctttcc agggaaaagg ctgaattaag aaaggcaaaa gaaaataagg aatcagaggc
5761 taaagttacc agccacacag aactaacctc caaccaacaa tcagctaata agacacaagc
5821 tattgcaaag cagccaataa atcgaggtca gcctaaaccc atacttcaga aacaatccac
5881 ttttccccag tcatccaaag acataccaga cagaggggca gcaactgatg aaaagttaca
5941 gaattttgct attgaaaata ctccggtttg cttttctcat aattcctctc tgagttctct
6001 cagtgacatt gaccaagaaa acaacaataa agaaaatgaa cctatcaaag agactgagcc
6061 ccctgactca cagggagaac caagtaaacc tcaagcatca ggctatgctc ctaaatcatt
6121 tcatgttgaa gatacccag tttgtttctc aagaaacagt tctctcagtt ctcttagtat
6181 tgactctgaa gatgacctgt tgcaggaatg tataagctcc gcaatgccaa aaaagaaaaa
6241 gccttcaaga ctcaagggtg ataatgaaaa acatagtccc agaaatatgg gtggcatatt
6301 aggtgaagat ctgacacttg atttgaaaga tatacagaga ccagattcag aacatggtct
6361 atccctgat tcagaaaatt ttgattggaa agctattcag gaaggtgcaa attccatagt
6421 aagtagttta catcaagctg ctgctgctgc atgtttatct agacaagctt cgtctgattc
6481 agattccatc ctttccctga aatcaagaat ctctctggga tcaccatttc atcttacacc
6541 tgatcaagaa gaaaaaccct ttacaagtaa taaaggccca cgaattctaa accaggggga
6601 gaaaagtaca ttggaaacta aaaagataga atctgaaagt aaaggaatca aaggaggaaa
6661 aaaagtttat aaaagtttga ttactggaaa agttcgatct aattcagaaa tttcaggcca
6721 aatgaaacag cccccttcaag caaacatgcc ttcaatctct cgaggcagga caatgattca
6781 tattccagga gttcgaaata gctcctcaag tacaagtcct gtttctaaaa aaggcccacc
6841 ccttaagact ccagcctcca aaagccctag tgaaggtcaa acagccacca cttctcctag
6901 aggagccaag ccatctgtga aatcagaatt aagccctgtt gccaggcaga catcccaaat
6961 aggtgggtca agtaaagcac cttctagatc aggatctaga gattcgaccc cttcaagacc
7021 tgcccagcaa ccattaagta gacctataca gtctcctggc cgaaactcaa tttcccctgg
7081 tagaaatgga ataagtcctc ctaacaaatt atctcaactt ccaaggacat catccctag
7141 tactgcttca actaagtcct caggttctgg aaaaatgtca tatacatctc caggtagaca
7201 gatgagccaa cagaaccttta ccaaacaaac aggtttatcc aagaatgcca gtagtattcc
7261 aagaagtgag tctgcctcca aaggactaaa tcagatgaat aatggtaatg gagccaataa
7321 aaaggtagaa ctttctagaa tgtcttcaac taaatcaagt ggaagtgaat ctgatagatc
7381 agaaagacct gtattagtac gccagtcaac tttcatcaaa gaagctccaa gcccaacctt
7441 aagaagaaaa ttggaggaat ctgcttcatt tgaatctctt tctccatcat ctagaccagc
7501 ttctcccact aggtcccagg cacaaactcc agttttaagt ccttccttc ctgatatgtc
7561 tctatccaca cattcgtctg ttcaggctgg tggatggcga aaactcccac ctaatctcag
7621 tcccactata gagtataatg atggaagacc agcaaagcgc catgatattg cacggtctca
7681 ttctgaaagt ccttctagac ttccaatcaa taggtcagga acctggaaac gtgagcacag
7741 caaacattca tcatcccttc ctcgagtaag cacttggaga agaactggaa gttcatcttc
7801 aattctttct gcttcatcag aatccagtga aaaagcaaaa agtgaggatg aaaaacatgt
7861 gaactctatt tcaggaacca aacaaagtaa agaaaaccaa gtatccgcaa aaggaacatg
```

-continued

```
7921 gagaaaaata aaagaaaatg aattttctcc cacaaatagt acttctcaga ccgtttcctc
7981 aggtgctaca aatggtgctq aatcaaagac tctaatttat caaatggcac ctgctgtttc
8041 taaaacagag gatgtttggg tgagaattga ggactgtccc attaacaatc ctagatctgg
8101 aagatctccc acaggtaata ctcccccggt gattgacagt gtttcagaaa aggcaaatcc
8161 aaacattaaa gattcaaaag ataatcaggc aaaacaaaat gtgggtaatg gcagtgttcc
8221 catgcgtacc gtgggtttgg aaaatcgcct gaactccttt attcaggtgg atgcccctga
8281 ccaaaaagga actgagataa aaccaggaca aaataatcct gtccctgtat cagagactaa
8341 tgaaagttct atagtggaac gtaccccatt cagttctagc agctcaagca aacacagttc
8401 acctagtggg actgttgctg ccagagtgac tccttttaat tacaacccaa gccctaggaa
8461 aagcagcgca gatagcactt cagctcggcc atctcagatc ccaactccag tgaataacaa
8521 cacaaagaag cgagattcca aaactgacag cacagaatcc agtggaaccc aaagtcctaa
8581 gcgccattct gggtcttacc ttgtgacatc tgttaaaaag agaggaagaa tgaaactaag
8641 aaaattctat gttaattaca actgctatat agacattttg tttcaaatga aactttaaaa
8701 gactgaaaaa ttttgtaaat aggtttgatt cttgttagag ggttttttgtt ctggaagcca
8761 tatttgatag tatactttgt cttcactggt cttattttgg gaggcactct tgatggttag
8821 gaaaaaaata gtaaagccaa gtatgtttgt acagtatgtt ttacatgtat ttaaagtagc
8881 atcccatccc aacttccttt aattattgct tgtcttaaaa taatgaacac tacagataga
8941 aaatatgata tattgctgtt atcaatcatt tctagattat aaactgacta aacttacatc
9001 agggaaaaat tggtatttat gcaaaaaaaa atgttttgt ccttgtgagt ccatctaaca
9061 tcataattaa tcatgtggct gtgaaattca cagtaatatg gttcccgatg aacaagttta
9121 cccagcctgc tttgctttac tgcatgaatg aaactgatgg ttcaatttca gaagtaatga
9181 ttaacagtta tgtggtcaca tgatgtgcat agagatagct acagtgtaat aatttacact
9241 attttgtgct ccaaacaaaa caaaaatctg tgtaactgta aaacattgaa tgaaactatt
9301 ttacctgaac tagattttat ctgaaagtag gtagaatttt tgctatgctg taatttgttg
9361 tatattctgg tatttgaggt gagatggctg ctcttttatt aatgagacat gaattgtgtc
9421 tcaacagaaa ctaaatgaac atttcagaat aaattattgc tgtatgtaaa ctgttactga
9481 aattggtatt tgtttgaagg gtcttgtttc acatttgtat taataattgt ttaaaatgcc
9541 tcttttaaaa gcttatataa atttttttct tcagcttcta tgcattaaga gtaaaattcc
9601 tcttactgta ataaaaacaa ttgaagaaga ctgttgccac ttaaccattc catgcgttgg
9661 cacttatcta ttcctgaaat ttcttttatg tgattagctc atcttgattt ttaatatttt
9721 tccacttaaa ctttttttc ttactccact ggagctcagt aaaagtaaat tcatgtaata
9781 gcaatgcaag cagcctagca cagactaagc attgagcata ataggcccac ataatttcct
9841 ctttcttaat attatagaat tctgtacttg aaattgattc ttagacattg cagtctcttc
9901 gaggctttac agtgtaaact gtcttgcccc ttcatcttct tgttgcaact gggtctgaca
9961 tgaacacttt ttatcaccct gtatgttagg gcaagatctc agcagtgaag tataatcagc
10021 actttgccat gctcagaaaa ttcaaatcac atggaacttt agaggtagat ttaatacgat
10081 taagatattc agaagtatat tttagaatcc ctgcctgtta aggaaacttt atttgtggta
10141 ggtacagttc tggggtacat gttaagtgtc cccttataca gtggagggaa gtcttccttc
10201 ctgaaggaaa ataaactgac acttattaac taagataatt tacttaatat atcttccctg
10261 atttgtttta aaagatcaga gggtgactga tgatacatgc atacatattt gttgaataaa
10321 tgaaaattta ttttttagtga taagattcat acactctgta tttggggagg gaaaaccttt
```

```
10381 ttaagcatgg tggggcactc agataggagt gaatacacct acctggtgcc ttgaaaatca 10441 catcaagtag ttaattatct accccttacc tgtgtttata acttccaggt aatgagaatg 10501 atttttttta aagctaaaat gccagtaaat aaaagtgcta tgacttgagc taagatattt 10561 gactccaatg cctgtactgt gtctactgca ccactttgta aacacttcaa tttactatct 10621 ttgaaatgat tgacctttaa atttttgcca aatgttatct gaaattgtct atgaatacca 10681 tctacttctg ttgttttccc aggcttccat aaacaatgga gatacatgca aaaaaaaaa
```

Familial adenomatous polyposis (FAP) is caused by mutations in the APC gene. More than 800 mutations in the APC gene have been identified in families with classic and attenuated types of familial adenomatous polyposis. Most of these mutations cause the production of an APC protein that is abnormally short and nonfunctional. This short protein cannot suppress the cellular overgrowth that leads to the formation of polyps, which can become cancerous. The most common mutation in familial adenomatous polyposis is a deletion of five bases in the APC gene. This mutation changes the sequence of amino acids in the resulting APC protein beginning at position 1309.

Another mutation is carried by approximately 6 percent of people of Ashkenazi (eastern and central European) Jewish heritage. This mutation results in the substitution of the amino acid lysine for isoleucine at position 1307 in the APC protein (also written as I1307K or Ile1307Lys). This change was initially thought to be harmless, but has recently been shown to be associated with a 10 to 20 percent increased risk of colon cancer.

Detection of Biomarkers

Any suitable method can be used to detect the biomarker(s). Successful practice of the invention can be achieved with one or a combination of methods that can detect and, in embodiments, quantify the biomarker(s). Detection of the biomarkers of the invention (e.g. symmetric-dimethylarginine, symmetric-dimethylarginine, carnitine, methionine, dimethylglycine, betaine, proline, glutamine, glutamic acid, threonine, and Nα-acetyllysine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline and M264 can be detected using one or more methods well known in the art, including, without limitation, mass spectrometry, chromatography, spectroscopy (e.g., NMR), elemental analysis, conventional chemical methods, immunoassays, and the like.

Detection of the biomarkers can be conducted in the same or different samples, the same or separate assays, and may be conducted in the same or different reaction mixtures. Where the biomarkers are assayed in different samples, the samples are usually obtained from the subject during the same procedure (e.g., urine collection, blood draw, tissue extraction, and the like) or with only a relative short time intervening so as to avoid an incorrect result due to passage of time. Where the biomarkers are detected in separate assays, the samples assayed are can be derived from the same or different samples obtained from the subject to be tested.

In embodiments, the biomarker(s) are detected using mass spectrometry. Mass spectrometry-based methods exploit the differences in mass of biomarkers to facilitate detection. Mass spectrometry can be combined with other assays, e.g., resolving the analyte in a sample by one or two passes through liquid or gas chromatography followed by mass spectrometry analysis. Methods for preparing a biological sample for analysis by mass spectrometry are well known in the art. Suitable mass spectrometers for use include, without limit, electrospray ionization mass spectrometry (ESI-MS), ESIMS/MS, ESI-MS/(MS)n (n is an integer greater than zero), matrix-assisted laser desorption ionization time-of-flight mass spectrometry (MALDI-TOF-MS), electron impact ionization mass spectrometry (EI-MS), chemical ionization mass spectrometry (CI-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI (MS)11, atmospheric pressure photoionization mass spectrometry (APPI-MS), APPI-MS/MS, APPI-(MS), quadrupole, fourier transform mass spectrometry (FTMS), ion trap, and hybrids of these methods, e.g., electrospray ionization quadrupole time-of-flight mass spectrometry (UPLC-ESI-QTOFMS) and two-dimensional gas chromatography electron impact ionization mass spectrometry (GC×GC-EI-MS).

The methods may be performed in an automated (Villanueva, et al., Nature Protocols (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454 and 20050035286; U.S. Pat. No. 5,800,979; and the references disclosed therein.

Samples are collected on a collection layer. They may then be analyzed by a spectroscopic method based on matrix-assisted laser desorption/ionization (MALDI), electrospray ionization (ESI), and the like.

Other techniques for improving the mass accuracy and sensitivity of the MALDI-TOF MS can be used to analyze the analytes obtained on the collection membrane. These include the use of delayed ion extraction, energy reflectors and ion-trap modules. In addition, post source decay and MS-MS analysis are useful to provide further structural analysis. With ESI, the sample is in the liquid phase and the analysis can be by ion-trap, TOF, single quadrupole or multi-quadrupole mass spectrometers. The use of such devices (other than a single quadrupole) allows MS-MS or MS" analysis to be performed. Tandem mass spectrometry allows multiple reactions to be monitored at the same time.

Capillary infusion may be employed to introduce the marker to a desired MS implementation, for instance, because it can efficiently introduce small quantities of a sample into a mass spectrometer without destroying the vacuum. Capillary columns are routinely used to interface the ionization source of a MS with other separation techniques including gas chromatography (GC) and liquid chromatography (LC). GC and LC can serve to separate a solution into its different components prior to mass analysis. Such techniques are readily combined with MS, for instance. One variation of the technique is that high performance liquid chromatography (HPLC) can now be directly coupled to mass spectrometer for integrated sample separation/and mass spectrometer analysis.

Quadrupole mass analyzers may also be employed as needed to practice the invention. Fourier-transform ion cyclotron resonance (FTMS) can also be used for some invention embodiments. It offers high resolution and the ability of tandem MS experiments. FTMS is based on the principle of a charged particle orbiting in the presence of a magnetic field. Coupled to ESI and MALDI, FTMS offers high accuracy with errors as low as 0.001%.

In embodiments, the diagnostic methods of the invention may further comprise identifying significant peaks from combined spectra. The methods may also further comprise searching for outlier spectra. In other embodiments, the methods of the invention further comprise determining distant dependent K-nearest neighbors.

In embodiments, an ion mobility spectrometer can be used to detect and characterize the biomarker(s). The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a biomarker or other substances in a sample. One advantage of ion mobility spectrometry is that it can operate at atmospheric pressure.

In embodiments, the procedure is electrospray ionization quadrupole mass spectrometry with time of flight (TOF) analysis, known as UPLC-ESI-QTOFMS. UPLC-ESI-QTOFMS is well known in the art (see, e.g., Manna et al., *J. Proteome Res.* 9:4176-88 (2010)) and methods for using UPLC-ESI-QTOFMS are described in detail herein.

In embodiments, detection of the biomarker(s) involves chemical methods well known in the art. In embodiments, the chemical method is chemical extraction. In embodiments, the chemical method is chemical derivitization.

In embodiments, detection of the biomarker(s) involves use of chromatography methods that are well known in the art. Such chromatography methods include, without limit, column chromatography, ion exchange chromatography, hydrophobic (reverse phase) liquid chromatography, normal phase chromatography, hydrophilic interaction liquid chromatography, or other chromatography, such as thinlayer, gas, or liquid chromatography (e.g., high-performance or ultra-performance liquid chromatography), or any combination thereof.

In embodiments, detection of the biomarker(s) involves use of spectroscopy methods that are well known in the art. Such chromatography methods include, without limitation, NMR, IR, and the like.

In embodiments, detection of the biomarker(s) involves elemental analysis methods that are well known in the art. Such elemental analysis methods include, without limitation, combustion analysis, gravimetry, atomic spectroscopy, and the like.

In embodiments, detection of the biomarker(s) involves use of immunoassays. In embodiments, the immunoassays involve the use of antibodies. Suitable immunoassays include, without limitation, ELISA, flow chamber adhesion, colorimetric assays (e.g., antibody based colorimetric assays), biochip (e.g., antibody based biochip), and the like.

Analytes (e.g., biomarkers) can be detected by a variety of detection methods. Detection methods may include use of a biochip array. Biochip arrays useful in the invention include protein and polynucleotide arrays. One or more markers are captured on the biochip array and subjected to analysis to detect the level of the markers in a sample.

Markers may be captured with capture reagents immobilized to a solid support, such as a biochip, a multiwell microtiter plate, a resin, or a nitrocellulose membrane that is subsequently probed for the presence or level of a marker. Capture can be on a chromatographic surface or a biospecific surface. For example, a sample containing the markers, such as serum, may be used to contact the active surface of a biochip for a sufficient time to allow binding. Unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. In one embodiment, mass spectrometry, and in particular, SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Other variations of the assays described herein to provide for different assay formats for detection of the biomarker(s) will be readily apparent to the one of ordinary skill in the art upon reading the present disclosure.

Types of Biological Samples

The level of symmetric-dimethylarginine, symmetric-dimethylarginine, carnitine, methionine, dimethylglycine, betaine, proline, glutamine, glutamic acid, threonine, and Nα-acetyllysine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline and M264, or a combination thereof, is measured in different types of samples. In embodiment, the level of the biomarker(s) is measured in a biologic sample. Suitable biologic samples include, without limit, a tissue sample (e.g., from a biopsy) and biological or physiological fluids (e.g., urine, blood, blood serum, plasma, fecal aspirate, intestinal aspirate, bile, saliva, cerebrospinal fluid or any other biological fluid useful in the methods of the invention). In embodiments, the sample is a urine sample derived from the patient. In particular embodiments, the collection of a biological fluid is noninvasive (e.g., urine).

Subject Monitoring

The disease state or treatment of a subject having neoplasia (including colorectal cancer), or a propensity to develop such a condition can be monitored using the methods and biomarkers of the invention. In embodiments, methods and biomarkers of the invention are used by a clinician to identify subjects as having or not having neoplasia. For example, a general practitioner may use the methods delineated herein to screen patients for the presence of neoplasia. In embodiments, the level of biomarker(s) present in a patient sample, e.g., bodily fluid such as urine, blood, blood serum, plasma, fecal aspirate, bile, intestinal aspirate, or saliva, is monitored. Such monitoring may be useful, for example, in assessing disease progression or in assessing the efficacy of a particular drug in a subject. An increase in the level of a biomarker of the invention (e.g., symmetric-dimethylarginine, symmetric-dimethylarginine, carnitine, methionine, dimethylglycine, betaine, proline, glutamine, glutamic acid, threonine, and Nα-acetyllysine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline and M264, or a combination thereof as specified herein) may indicate cancer onset or relapse. A decrease in the level of a biomarker of the invention (e.g., symmetric-dimethylarginine, symmetric-dimethylarginine, carnitine, methionine, dimethylglycine, betaine, proline, glutamine, glutamic acid, threonine, and Nα-acetyllysine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline and M264, or a combination thereof as specified herein) may indicate cancer remission or the effectiveness of a therapy. Therapeutics that decrease the level of a biomarker of the invention (e.g., symmetric-dimethylarginine, symmetric-dimethylarginine, carnitine, methionine, dimethylglycine, betaine, proline, glutamine, glutamic acid, threonine, and Nα-acetyllysine, xanthosine, inosine, deoxyuridine, thymidine, deoxycytidine, cytosine, hypoxanthine, xanthine, uracil, guanosine, adenosine, N1-acetylspermidine, N8-acetylspermidine, spermine, arginine ornithine, citrulline and M264, or a combination thereof as specified herein) are taken as particularly useful in the invention.

In embodiments, the biomarker(s) are monitored prior to administering therapy. These results provide a baseline that describes the level of the biomarker(s) prior to treatment. In embodiments, the biomarker(s) are monitored periodically. In embodiments, the biomarker(s) are monitored periodically throughout treatment. A therapy is identified as efficacious when a diagnostic assay of the invention detects a decrease in marker levels relative to the baseline level of marker prior to treatment.

Selection of a Treatment Method

After a subject is diagnosed as having colorectal cancer, a method of treatment is selected. In colorectal cancer, for example, a number of standard treatment regimens are available. The marker profile of the neoplasia is used in selecting a treatment method. Increased levels of symmetric-dimethylarginine, symmetric-dimethylarginine, carnitine, methionine, dimethylglycine, or betaine (methylation) correlate with a poor prognosis and an increased risk of death. Additionally, the levels of the methylation biomarkers may be used alone or in combination with the levels of biomarkers from one or more of the following groups: biomarkers related to nucleic acid metabolism including xanthosine, inosine, deoxyuridine, thymidine, deoxycytidine, cytosine, hypoxanthine, xanthine, uracil, guanosine, and adenosine; biomarkers related to urea cycle and polyamine metabolism including N1-acetylspermidine, N8-acetylspermidine, spermine, arginine omithine, and citrulline; and biomarkers related to amino acid metabolism including proline, glutamine, glutamic acid, threonine, and Nα-acetyllysine, and M264 or a combination thereof. Increased levels of amino acid metabolism, nucleic acid metabolism, and/or polyamine metabolism biomarkers correlate with a poor prognosis and an increased risk of death. Such neoplasias are identified as aggressive neoplasias. Marker profiles that correlate with good clinical outcomes (e.g., decreased or basal levels of asymmetric-dimethylarginine and symmetric-dimethylarginine) are identified as less aggressive neoplasias.

Less aggressive neoplasias are likely to be susceptible to conservative treatment methods. Conservative treatment methods include, for example, cancer surveillance, which involves periodic patient monitoring using diagnostic assays of the invention. Cancer surveillance is selected when diagnostic assays indicate that the adverse effects of treatment (e.g., impotence, urinary, and bowel disorders) are likely to outweigh therapeutic benefits.

More aggressive neoplasias are less susceptible to conservative treatment methods. When methods of the invention indicate that a neoplasia is very aggressive, an aggressive method of treatment should be selected. Aggressive therapeutic regimens typically include one or more of the following therapies: radical surgery, radiation therapy (e.g., external beam and brachytherapy), and chemotherapy.

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As used herein, the term "colorectal cancer" is meant a collection of colon, rectum, large intestine, or appendix cells multiplying in an abnormal manner. Cancer growth is uncontrolled and progressive, and occurs under conditions that would not elicit, or would cause cessation of, multiplication of normal cells.

Patient Monitoring

The diagnostic methods of the invention are also useful for monitoring the course of a colon cancer in a patient or for assessing the efficacy of a therapeutic regimen. In one embodiment, the diagnostic methods of the invention are used periodically to monitor the levels of biomarkers in one or more of the following groups: biomarkers related to methylation including asymmetric-dimethylarginine, symmetric-dimethylarginine, carnitine, methionine, dimethylglycine, and betaine; biomarkers related to nucleic acid metabolism including xanthosine, inosine, deoxyuridine, thymidine, deoxycytidine, cytosine, hypoxanthine, xanthine, uracil, guanosine, and adenosine; the biomarker related to urea cycle and polyamine metabolism including N1-acetylspermidine, N8-acetylspermidine, spermine, arginine ornithine, and citrulline; and biomarkers related to amino acid metabolism including proline, glutamine, glutamic acid, threonine, and Nα-acetyllysine, and M264 or a combination thereof. In one example, the neoplasia is characterized using a diagnostic assay of the invention prior to administering therapy. This assay provides a baseline that describes the level of one or more markers of the neoplasia prior to treatment. Additional diagnostic assays are administered during the course of therapy to monitor the efficacy of a selected therapeutic regimen. A therapy is identified as efficacious when a diagnostic assay of the invention detects a decrease in marker levels relative to the baseline level of marker prior to treatment.

Microarrays

The invention provides diagnostic arrays or microarrays for measuring the levels of a metabolic biomarker in accordance with the invention. Capture reagents, including organic molecules, peptides, peptide mimetics, polypeptides, nucleic acid ligands, aptamers, and antibodies are useful array elements in the microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28:e3.i-e3.vii, 2000), MacBeath et al., (Science 289:1760-1763, 2000), Zhu et al. (Nature Genet. 26:283-289), and in U.S. Pat. No. 6,436,665, hereby incorporated by reference.

To produce a nucleic acid microarray oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

Metabolic biomarkers, such as those described herein, may also be analyzed using protein microarrays. Such arrays are useful in high-throughput low-cost screens to identify peptide or candidate compounds that bind a polypeptide of the invention, or fragment thereof. Typically, protein microarrays feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins are spotted on a substrate using any convenient method known to the skilled artisan (e.g., by hand or by inkjet printer). Preferably, such methods retain the biological activity or function of the protein bound to the substrate (Ge et al., supra; Zhu et al., supra).

The microarray is hybridized with a detectable probe. Such probes can be small molecules, polypeptides, or nucleic acids. For some applications, small molecule probes are derived from a biological sample taken from a patient, such as a bodily fluid (e.g., urine, blood, blood serum, plasma, bile, fecal aspirate, intestinal aspirate, cerebrospinal fluid, and saliva); a homogenized tissue sample (e.g. a tissue sample obtained by biopsy); or cultured cells (e.g., colorectal cancer cells). Binding or capture conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes (e.g., by washing), specifically bound probes are detected, for example, by fluorescence, enzyme activity (e.g., an enzyme-linked calorimetric assay), direct immunoassay, radiometric assay, or any other suitable detectable method known to the skilled artisan. A detection system may be used to measure the absence, presence, and amount of binding or capture for all of the biomarkers simultaneously (e.g., Heller et al., Proc. Natl. Acad. Sci. 94:2150-2155, 1997). Preferably, a scanner is used to determine the levels and patterns of fluorescence.

Diagnostic Kits

The invention provides kits for diagnosing or monitoring neoplasia (e.g., colorectal cancer), or for selecting a treatment for neoplasia. In embodiments, the kits include one or more reagents capable of detecting and/or capturing one or more of the following groups of biomarkers: biomarkers related to methylation including asymmetric-dimethylarginine, symmetric-dimethylarginine, carnitine, methionine, dimethylglycine, and betaine; biomarkers related to nucleic acid metabolism including xanthosine, inosine, deoxyuridine, thymidine, deoxycytidine, cytosine, hypoxanthine, xanthine, uracil, guanosine, and adenosine; biomarkers related to urea cycle and polyamine metabolism including N1-acetylspermidine, N8-acetylspermidine, spermine, arginine ornithine, and citrulline; and biomarkers related to amino acid metabolism including proline, glutamine, glutamic acid, threonine, and Nα-acetyllysine and M264 or a combination thereof. In certain embodiments, the reagent is an antibody or a mass spectrometry probe. The kit may include a collection of detection/capture reagents in the form of an array or panel which can be used for high throughput screening and/or profiling of samples.

In various embodiments, the kits include an affinity agent or adsorbent that retains one or more of the biomarkers, or a combination thereof. In related embodiments, the kit further contains directions for contacting a test sample with the affinity agent or adsorbent and detecting one or more of the biomarkers, or a combination thereof retained by the affinity agent or adsorbent. In various embodiments, the reagents and/or affinity agents are provided on a solid support (e.g., chip, microtiter plate, bead, resin, and the like). In embodiments, the kits include washing solution(s) or instructions for making a washing solution, in which the combination of the reagent/adsorbent and the washing solution allows capture of the biomarkers on the reagent/adsorbent.

In various embodiments, the kits include the biomarkers, which can be used as standard(s) for calibration as may be desired.

In various embodiments, the kit contains a container(s) that houses the components of the kit (e.g., reagent, adsorbant, solid support, and the like). Such containers can be boxes, ampoules, bottles, vials, tubes, bags, pouches, blister-packs, or other suitable container forms known in the art. Such containers can be made of plastic, glass, laminated paper, metal foil, and the like.

In various embodiments, the kits further contain directions for using the kit in any of the methods described herein (e.g., diagnosing neoplasia, monitoring neoplasia, characterizing neoplasia, selecting a treatment for neoplasia, and the like). In various embodiments, the instructions include at least one of the following: description of the reagents, supports, and/or affinity agents; warnings; indications; counter-indications; animal study data; clinical study data; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 2:
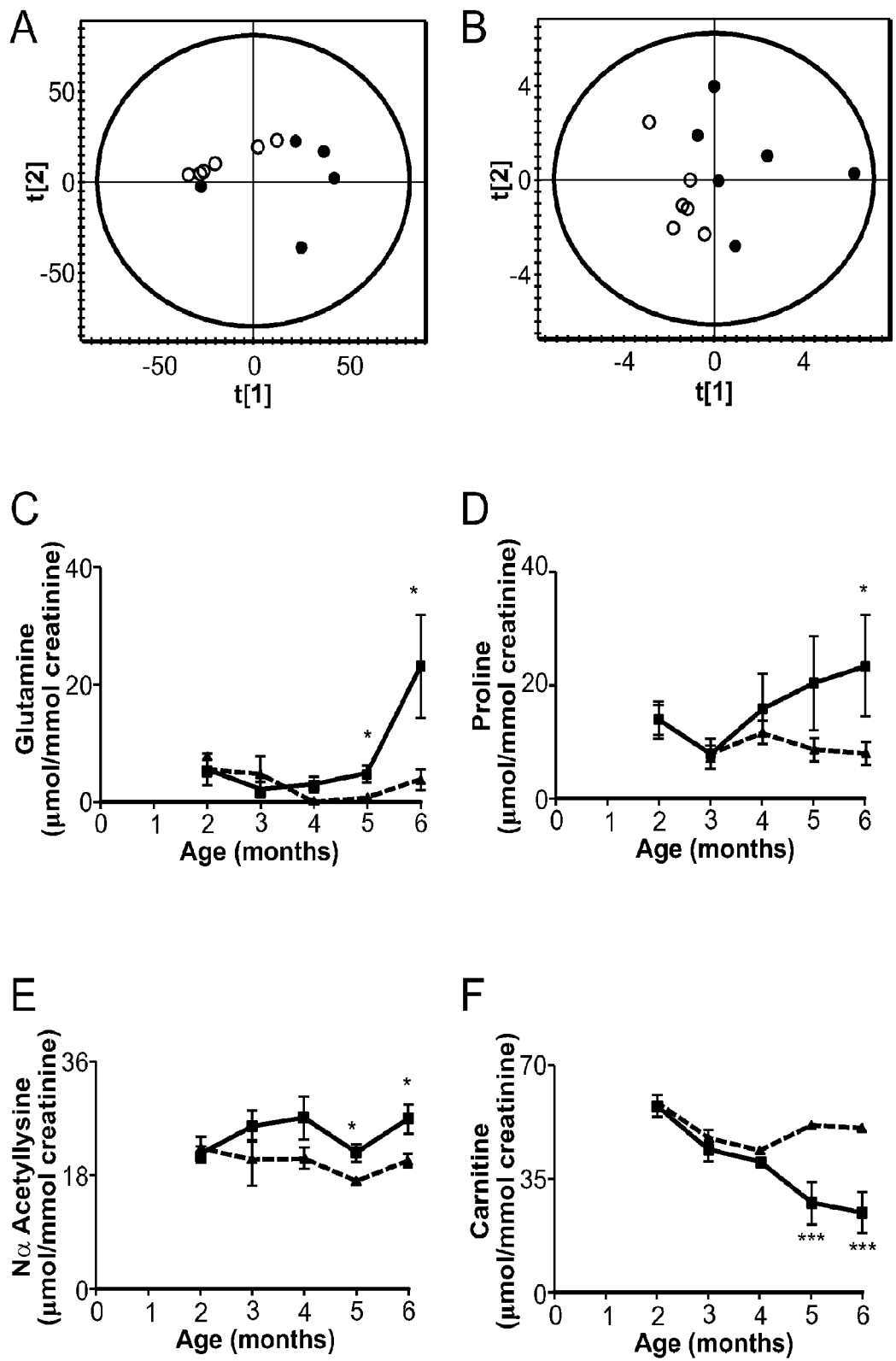
FIGS. 2A-2F depict the effect of tumorigenesis on global metabolomic signature and amino acid metabolism.
Figure 3:
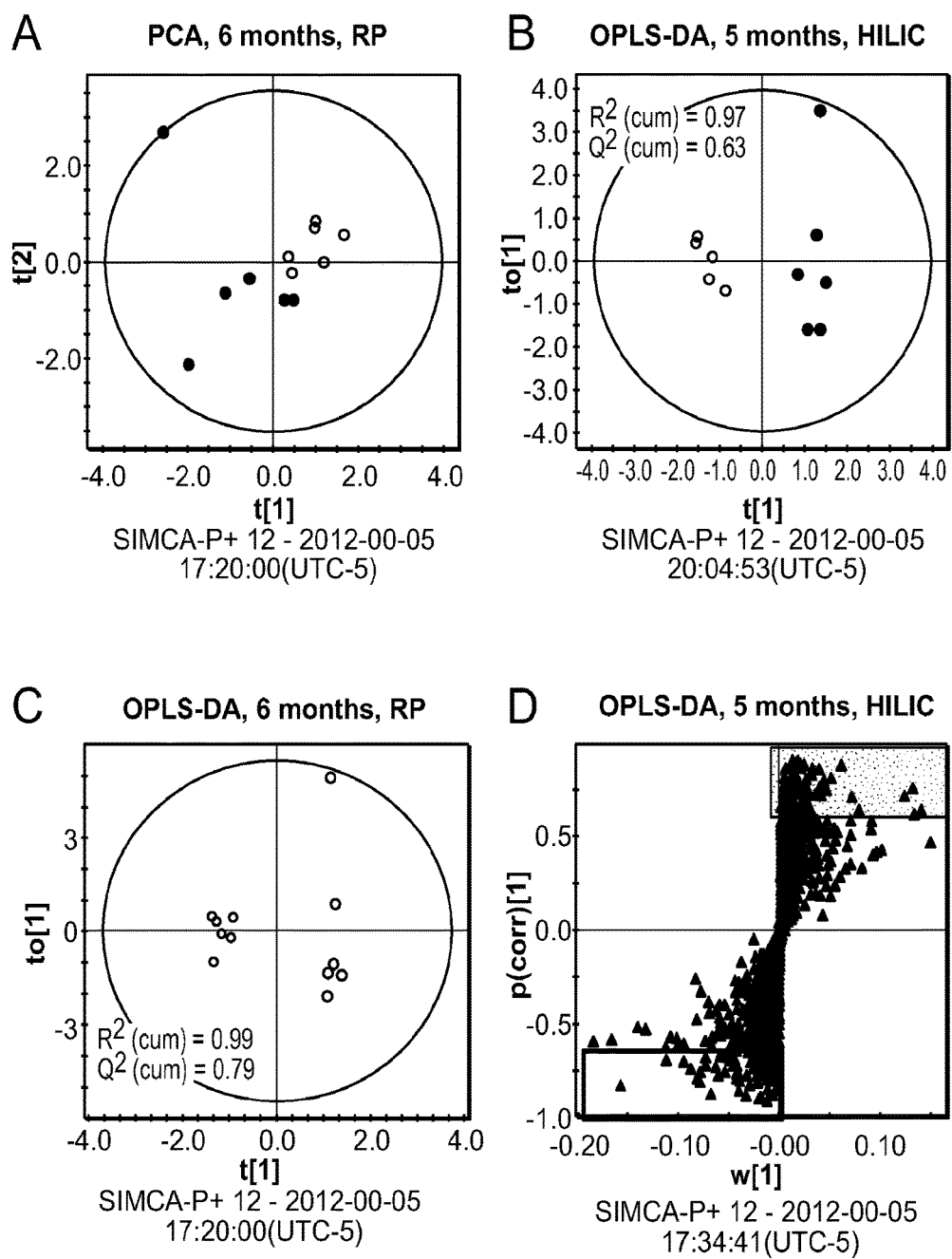
FIGS. 3A-3D depict analysis of creatinine-normalized metabolomic signature using reverse-phase separation.

Example 1. Distinct Metabolic Traits Correlated with Colorectal Tumor Development in APC$^{Min/+}$ Mice All APC$^{Min/+}$ mice studied developed colorectal tumors along with multiple intestinal polyps compared to wild-type mice, which were tumor-free at six months of age (FIG. 1A). The unsupervised principal components analysis of the total ion count-normalized urinary metabolomics data were acquired with hydrophilic interaction chromatography-based separation of the metabolites (FIG. 2A). Analysis of the urinary metabolomics data did not show segregation of APC$^{Min/+}$ and wild-type metabolomes. However, creatinine-normalized data (FIG. 2B) showed clear separation of the wild-type and APC$^{Min/+}$ animals along the first component in the principal components analysis (PCA), although none of the mice were visibly sick and there was no significant drop in body weight (FIG. 1B) or change in liver enzyme levels in serum (FIG. 1C) even at six months of age. Similarly, analysis of the creatinine-normalized metabolomic signature using reverse-phase separation also showed that while wild-type animals tended to cluster together, APC$^{Min/+}$ animals separated from the cluster along first component in PCA (FIG. 3A). These observations indicated that tumorigenesis in APC$^{Min/+}$ mice was associated with development of a distinct metabolic trait.

In order to identify the ions contributing to segregation of the metabolomic signature of naïve and tumor bearing mice, supervised orthogonal projection to latent structure analysis was performed (see FIGS. 3B and 3C). A significant number of ions were modulated as a result of tumorigenesis (FIG. 3D). The identities of these ions were confirmed and concentrations measured with authentic standards. The creatinine-normalized excretion of glutamine, proline, citrulline, Nα-acetyllysine, spermine, N1-acetylspermidine, N8-acetylspermidine, spermine, xanthosine, inosine, xanthine, deoxyuridine, cytidine, and thymidine were progressively elevated whereas those of ornithine and carnitine were reduced in tumor-bearing animals. A detailed description of quantitative ranges and statistical significances (P value and odds ratio) of these urinary biomarkers is provided at Table 1. The urinary excretion of glutamic acid, aspartic acid, lysine, arginine, hypoxanthine, creatine, Nω-monomethyl-arginine, and uridine were found to be unaffected during tumorigenesis.

Longitudinal Variation in Excretion of Amino Acid Metabolites.

The excretion of glutamine (FIG. 2C) was found to be progressively elevated in APC$^{Min/+}$ mice and was 7.2-fold and 6.1-fold higher than that in wild-type mice at five and six months, respectively. The excretion of proline was also were found to increase by 3.0-fold in tumor-bearing mice at six months (FIG. 2D). However, Nα-acetyllysine was elevated in urine of tumor bearing mice by 1.3-fold at both five and six months (FIG. 2E).

Longitudinal Variation in Excretion of Hypermethylated Metabolites.

Urinary excretion of carnitine, a permethylated metabolite of lysine, was reduced by 1.9- and 2.1-fold at five and six months, respectively (FIG. 2F). However, the urinary excretion of hypermethylated arginine metabolite symmetric-dimethylarginine was elevated by 1.7-fold and 1.6-fold at five and six months (FIG. 4A), while that of asymmetric-dimethylarginine (FIG. 4B) was also elevated by 1.7-fold and 2-fold at four and six months, respectively.

Longitudinal Variation in Urea Cycle and Polyamine Metabolites in Urine.

Figure 4:
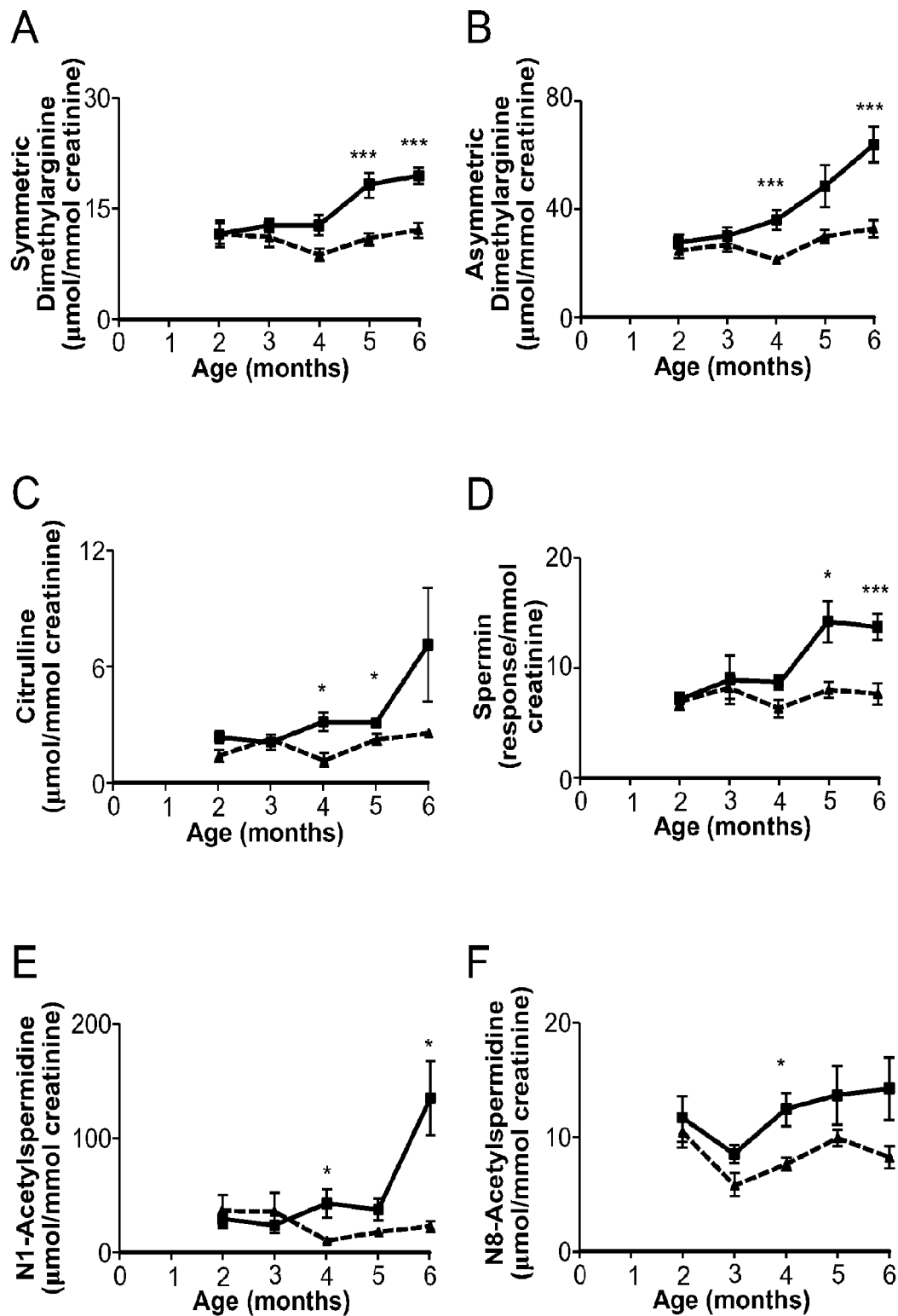
FIGS. 4A-4F depict the effect of tumorigenesis on urinary excretion of metabolites related to arginine and polyamine metabolism.

The creatinine-normalized urinary excretion of citrulline (FIG. 4C) was 2.7-fold and 1.4-fold higher at four and five months, respectively, while that of ornithine (FIG. 5A) was found to be lower by 1.4-fold at six months. Spermine excretion was progressively elevated in urine of tumor bearing animals and was found to be 1.8-fold higher at both five and six months (FIG. 4D). Acetylated polyamine metabolite N1-acetylspermidine (FIG. 4E) was elevated by 4.3-fold and 6.0-fold at four and six months, respectively, whereas N8-acetylspermidine (FIG. 4F) was elevated by 1.6-fold at four months.

Longitudinal Variation in Excretion of Purine and Pyrimidine Metabolites.

Figure 6:
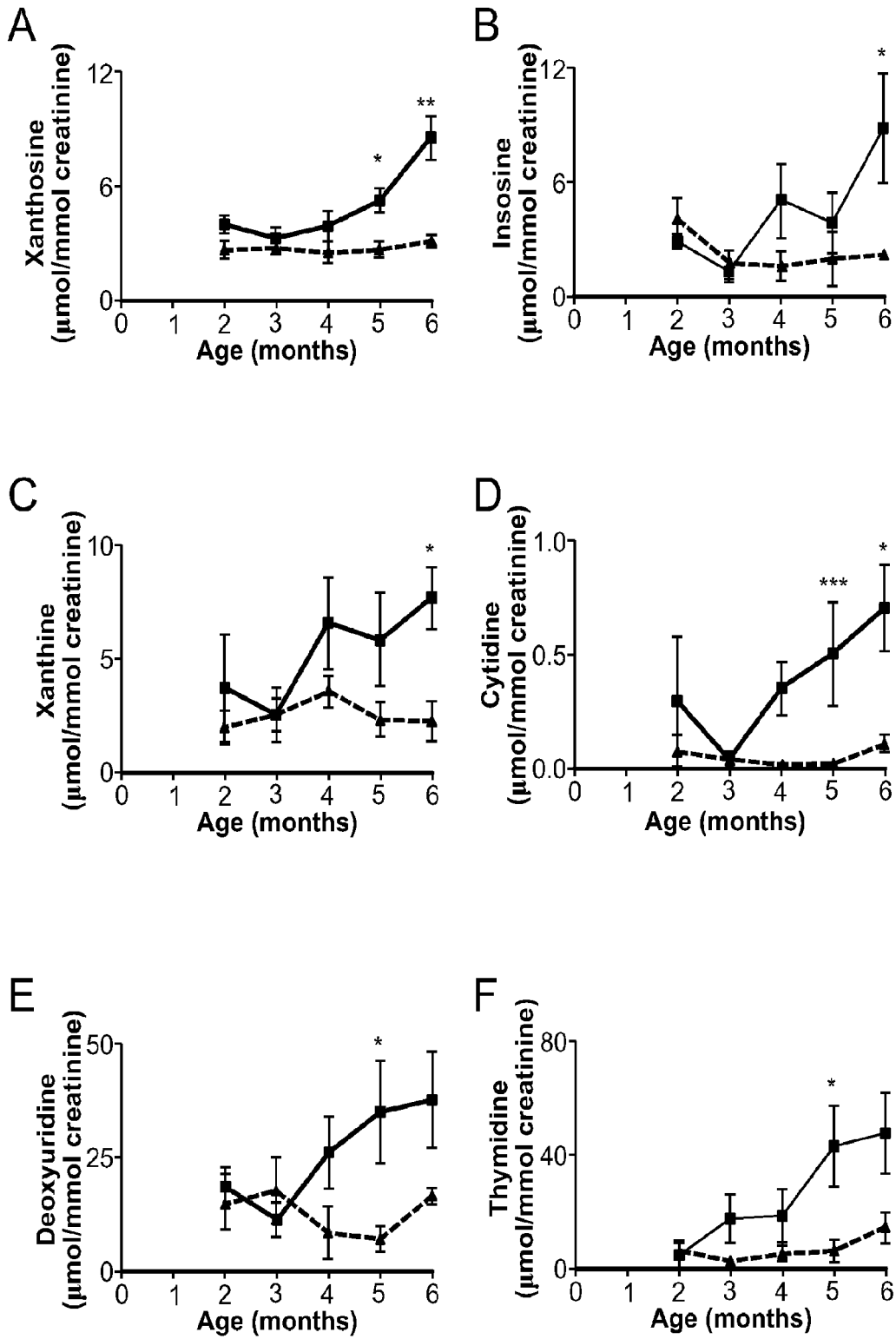
FIGS. 6A-6F depict the effect of tumorigenesis on urinary excretion of metabolites related to nucleic acid metabolism.

The urinary excretion of xanthosine (FIG. 6A) was elevated 2.0- and 2.8-fold at five and six months, respectively, whereas inosine (FIG. 6B) and xanthine (FIG. 6C) were elevated by 3.5- and 4.2-fold, respectively, at six months. The urinary excretion of cytidine (FIG. 6D) was elevated 28.7- and 6.8-fold at five and six months, respectively whereas that of deoxyuridine (FIG. 6E) and thymidine (FIG. 6F) were elevated by 5.0- and 7.4-fold, respectively, at five months.

Figure 7:
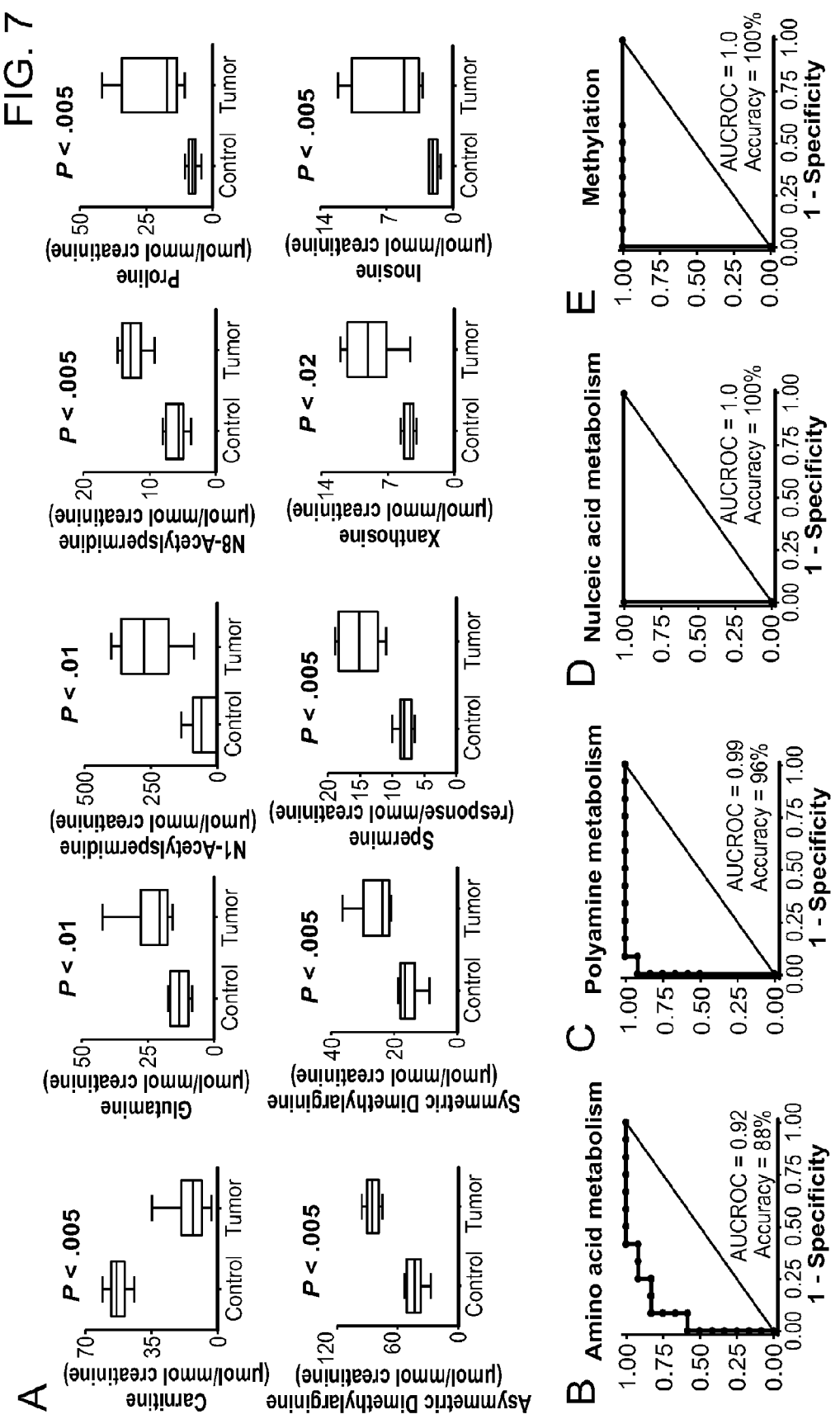
FIGS. 7A-7E depict validation of metabolomic biomarkers and evaluation of diagnostic power.
Figures 8A, 8B:
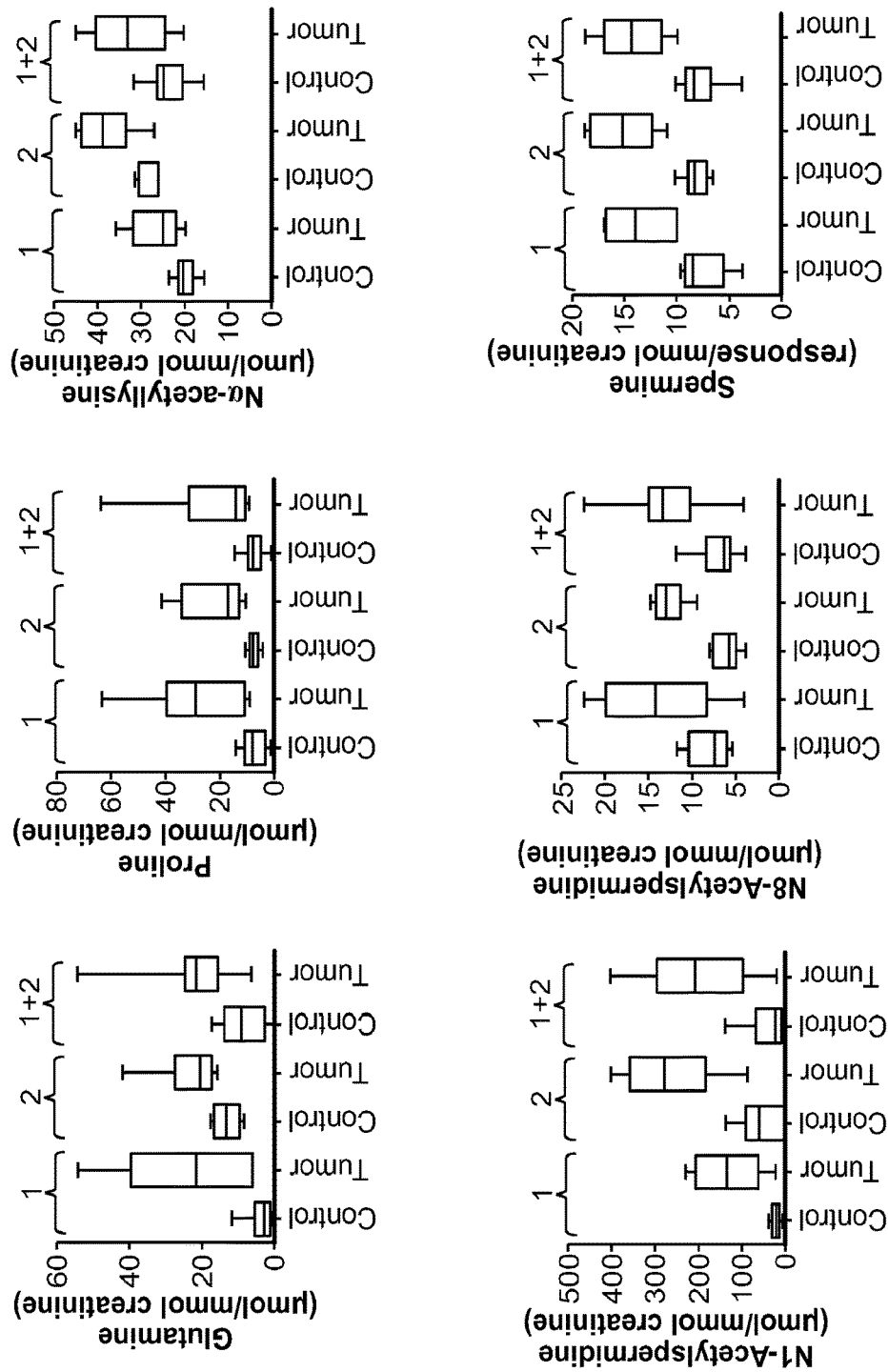
FIGS. 8A-8D are graphs of Box plots for comparison of ranges of creatinine-normalized urinary excretion of individual metabolites in discovery, validation and combined cohorts at six months.
Figures 8C, 8D:
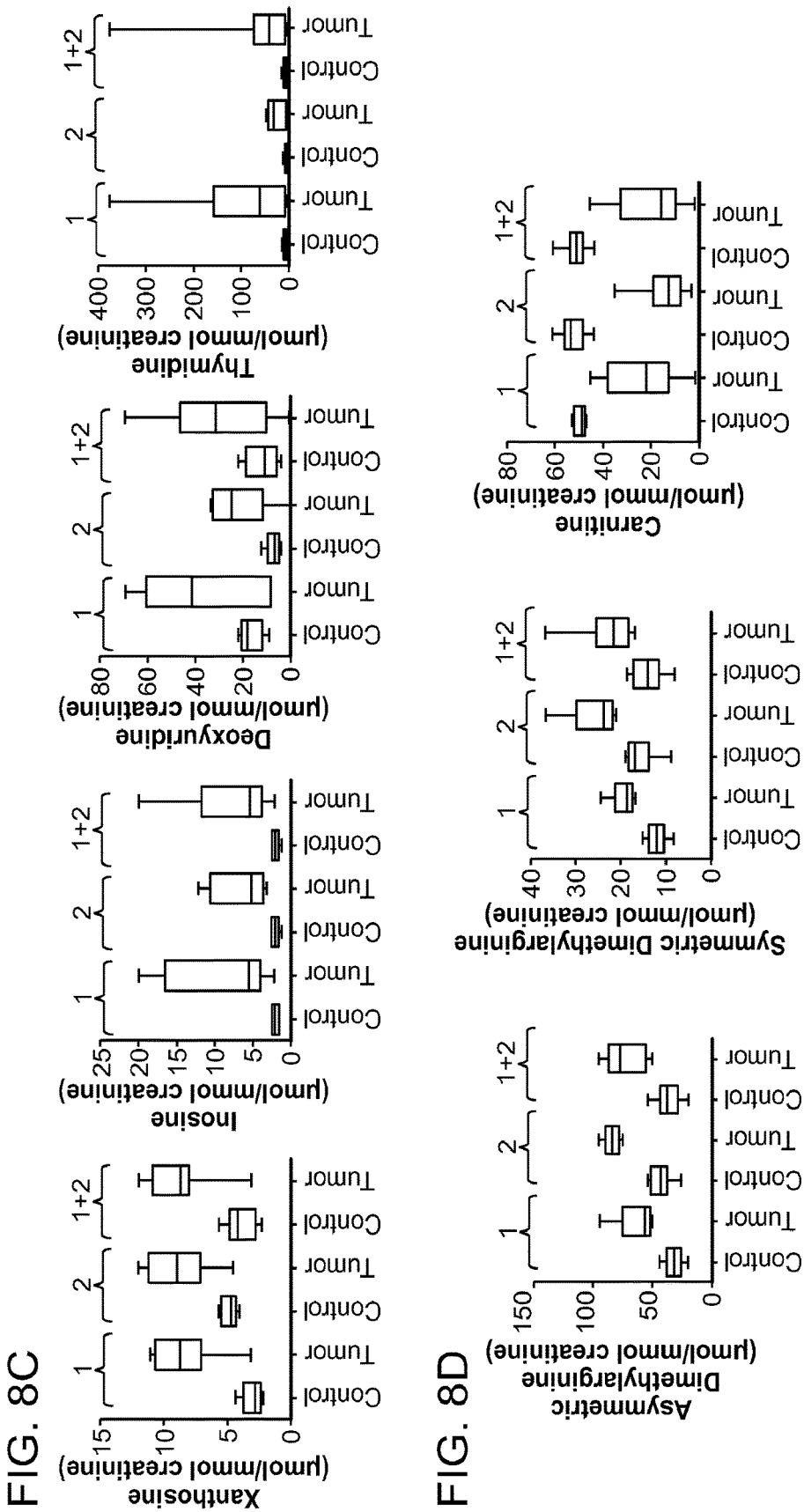

Example 2. Validation and Predictive Power of Urinary Excreted Metabolic Cancer Biomarkers The robustness of the biomarkers was tested in an independent cohort. Similar to that in the discovery cohort, the creatinine-normalized urinary excretions (FIG. 7A) of carnitine (3.6-fold) was reduced whereas those of glutamine (1.8-fold), NJ-acetylspermidine (4.8-fold), N8-acetylspermidine (2.1-fold), proline (2.9-fold), asymmetric-dimethylarginine (2-fold), symmetric-dimethylarginine (1.6-fold), spermine (1.9-fold), xanthosine (1.9-fold),

TABLE 1

| Metabolic pathway | | Identity | WT (av (95% CI) umol/mmol creatinine | APC (av (95% CI) umol/mmol creatinine | P (Mann-Whitney) | Fold change | OR (95% CI) |
|---|---|---|---|---|---|---|---|
| Amino acid metabolism | m5 | Proline | 22.4 (11.8-33.01) | 7.6(5.36-9.75) | 0.0004 | 2.96 | 1.82 (1.02-3.25) |
| | m9 | Glutamine | 23.14 (13.67-32.62) | 8.52 (4.58-12.47) | 0.0023 | 2.71 | 1.23 (1.04-1.47) |
| | m13 | Nα-acetyllysine | 32.52 (27.17-37.87) | 24.16 (21.2-27.13) | 0.0226 | 1.34 | 1.21 (1.02-1.45) |
| Polyamine metabolism | m1 | N1-acetylspermidine | 200.5 (127.8-273.1) | 39.06 913.26-64.85) | 0.0006 | 5.13 | 1.03 (1.01-1.05) |
| | m2 | N8-acetylspermidine | 13.26 (10.3-16.23) | 7.03 (5.62-8.44) | 0.0011 | 1.89 | 1.71 (1.15-2.54) |
| | m6 | Spermine | 14.28 (12.32-16.24) | 7.8 (6.7-8.91) | <0.0001 | 1.83 | 110.681 (0.04-334763) |
| Nucleic acid metabolism | | Xanthosine | 8.62 (6.98-10.28) | 3.91 (3.20-4.63) | 0.0005 | 2.21 | 2.7 (1.26-5.78) |
| | | Inosine | 7.64 (4.16-11.11) | 2.06 (1.80-2.32) | 0.0002 | 3.71 | 49.3 (0.7-4371) |
| | | Deoxyuridine | 29.5 (16.19-42.8) | 11.74 (7.76-15.72) | 0.0304 | 2.51 | 1.1 (1.01-1.22) |
| | | Thymidine | 63.37 (−1.40-128.1) | 5.55 (2.37-8.72) | 0.0004 | 11.43 | 1.14 (.99-1.32) |
| Methylation | | Asymmetric dimethylarginine | 73.86 (63.34-84.38) | 37.69 (31.26-44.12) | <0.0001 | 1.96 | 1.56 (.88-2.76) |
| | | Symmetric dimethylarginine | 22.49 (18.99-25.98) | 13.82 (11.62-16.01) | 0.0002 | 1.63 | 2.87 (.96-8.59) |
| | | Carnitine | 19.22 (10.62-27.83) | 51.39 (48.61-54.18) | <0.0001 | 0.37 | 0.53 (0.2-1.41) |

Figure 5:
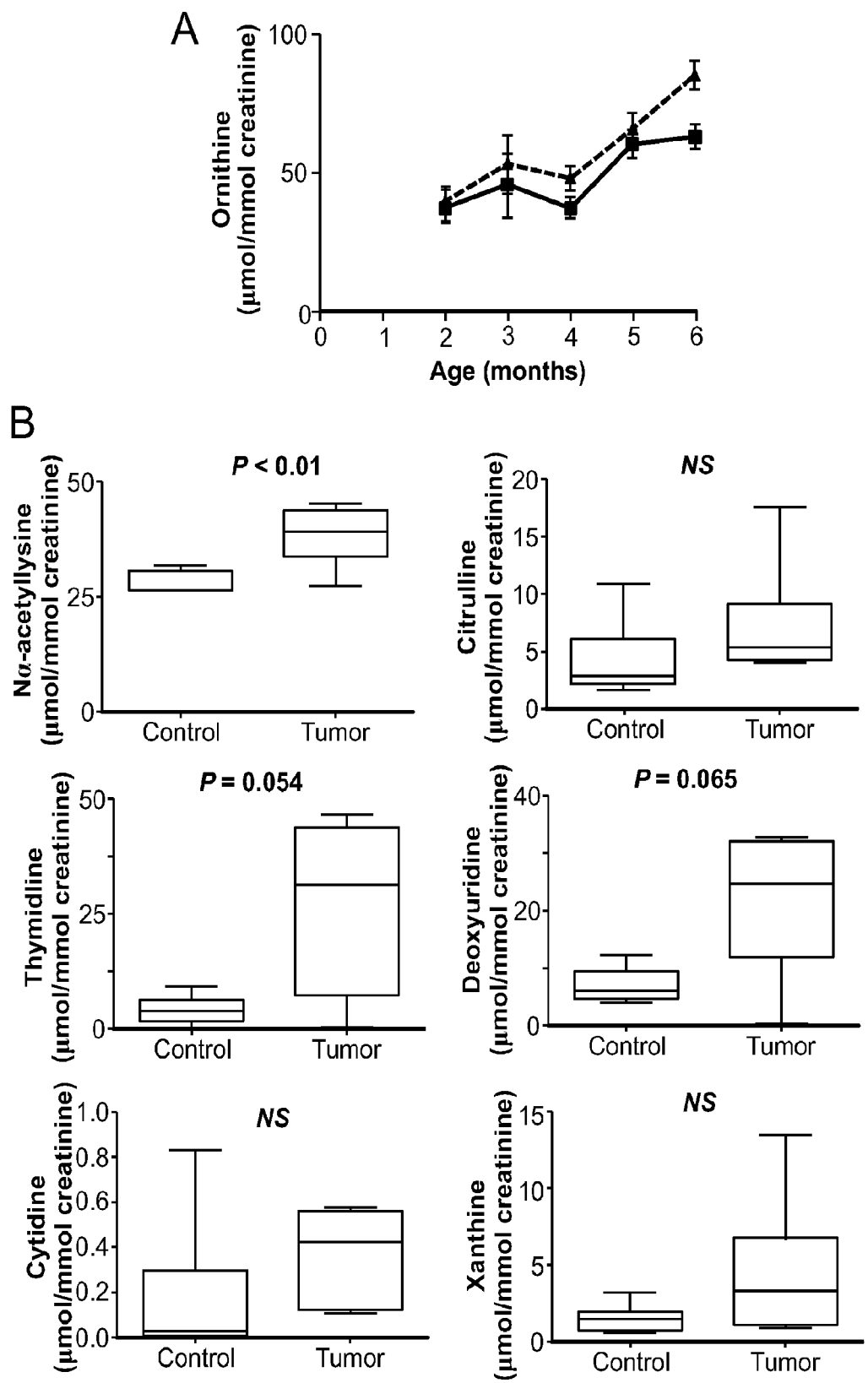
FIGS. 5A and 5B depict the effect of tumorigenesis on urinary excretion of metabolites related to urea cycle and polyamine metabolism.

| Metabolic pathway | | Identity | P (ROC) | AUCROC | Cut off | Sensitivity | Specificity | Accuracy |
|---|---|---|---|---|---|---|---|---|
| Amino acid metabolism | m5 | Proline | 0.044 | .93 (.82-1) | ≥10.79 | 83 | 92 | 88 |
| | m9 | Glutamine | 0.019 | 0.88 (0.73-1.0) | ≥18.19 | 73 | 100 | 87 |
| | m13 | Nα-acetyllysine | 0.026 | .77 (5.58-.97) | ≥35.96 | 50 | 100 | 75 |
| Polyamine metabolism | m1 | N1-acetylspermidine | 0.017 | 0.92 | ≥88.6 | 83 | 92 | 88 |
| | m2 | N8-acetylspermidine | 0.008 | 0.9 (.74-1.0) | ≥9.34 | 92 | 83 | 88 |
| | m6 | Spermine | 0.25 | .99 (.95-10 | ≥12.6 | 83 | 100 | 92 |
| Nucleic acid metabolism | | Xanthosine | 0.011 | 0.92 (.80-1.0) | ≥7.95 | 83 | 100 | 92 |
| | | Inosine | 0.073 | 0.96 (.87-1) | ≥3.20 | 92 | 100 | 96 |
| | | Deoxyuridine | 0.038 | .77 (.55-.97) | ≥30.0 | 58 | 100 | 79 |
| | | Thymidine | 0.066 | 0.84 (.67-1.0) | ≥21.02 | 67 | 100 | 83 |
| Methylation | | Asymmetric dimethylarginine | 0.123 | 0.98 (.94-1) | ≥52.31 | 92 | 92 | 92 |
| | | Symmetric dimethylarginine | 0.06 | .95 (.88-1) | ≥18.14 | 83 | 92 | 88 |
| | | Carnitine | 0.205 | 0.99 (.97-1.0) | ≥34.71 | 92 | 100 | 96 | inosine (3.2-fold), and Nα-acetyllysine (1.4-fold; FIG. 5B) were elevated in the urine of tumor-bearing animals. Although not statistically significant, urinary excretion of thymidine (6.6-fold, P=0.054) and deoxyuridine (3.1-fold, P=0.065), showed a trend toward elevation as observed in the discovery cohort (FIG. 5B).

Figure 9C:
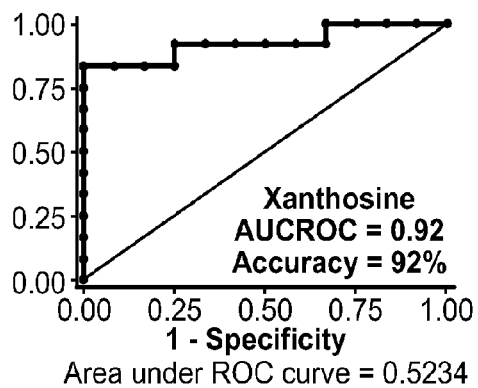
Figure 9C:
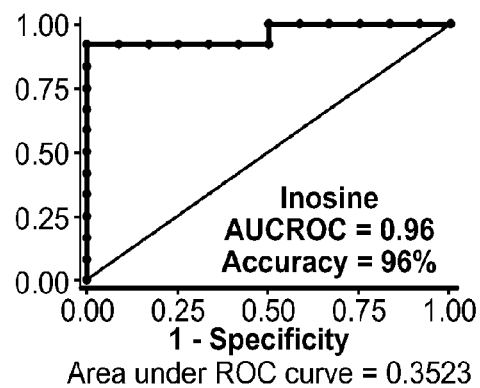
Figure 9C:
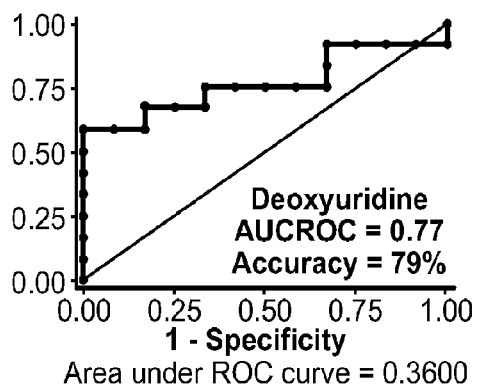
Figure 9C:
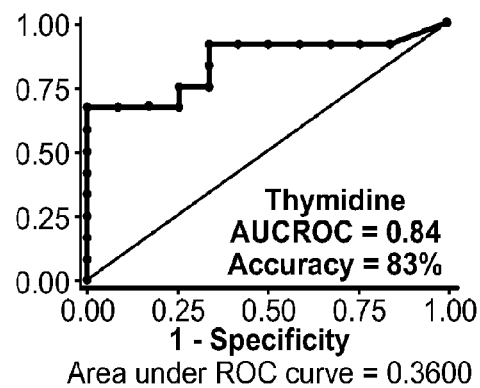
Figure 9D:
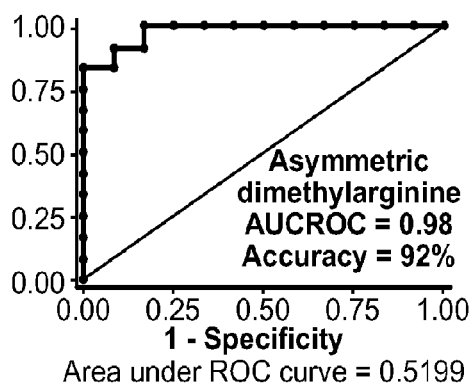
Figure 9D:
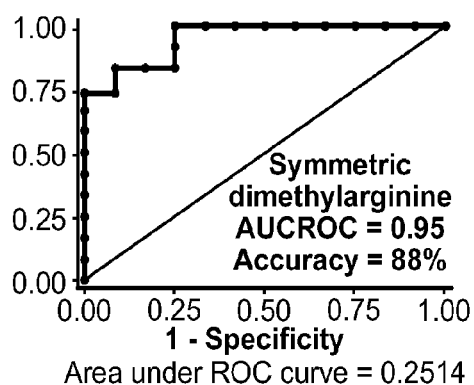
Figure 9D:
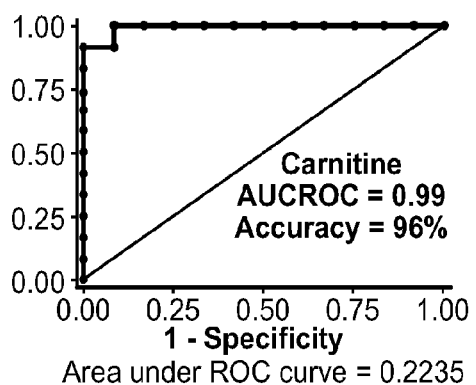
Figure 10A:
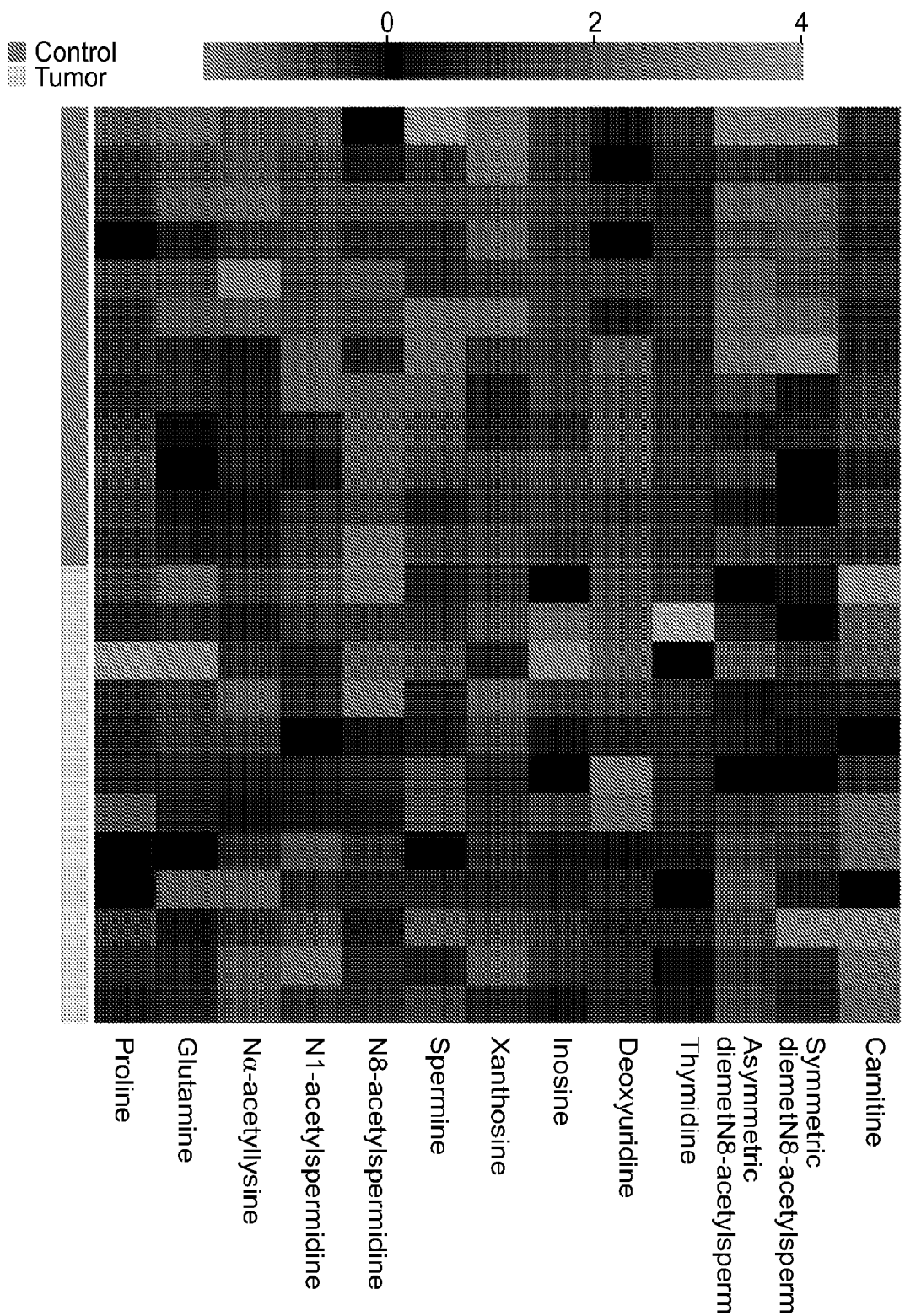
FIGS. 10A and 10B depict accuracy of tumor diagnosis using a panel of metabolic urinary biomarkers.
Figure 10B:
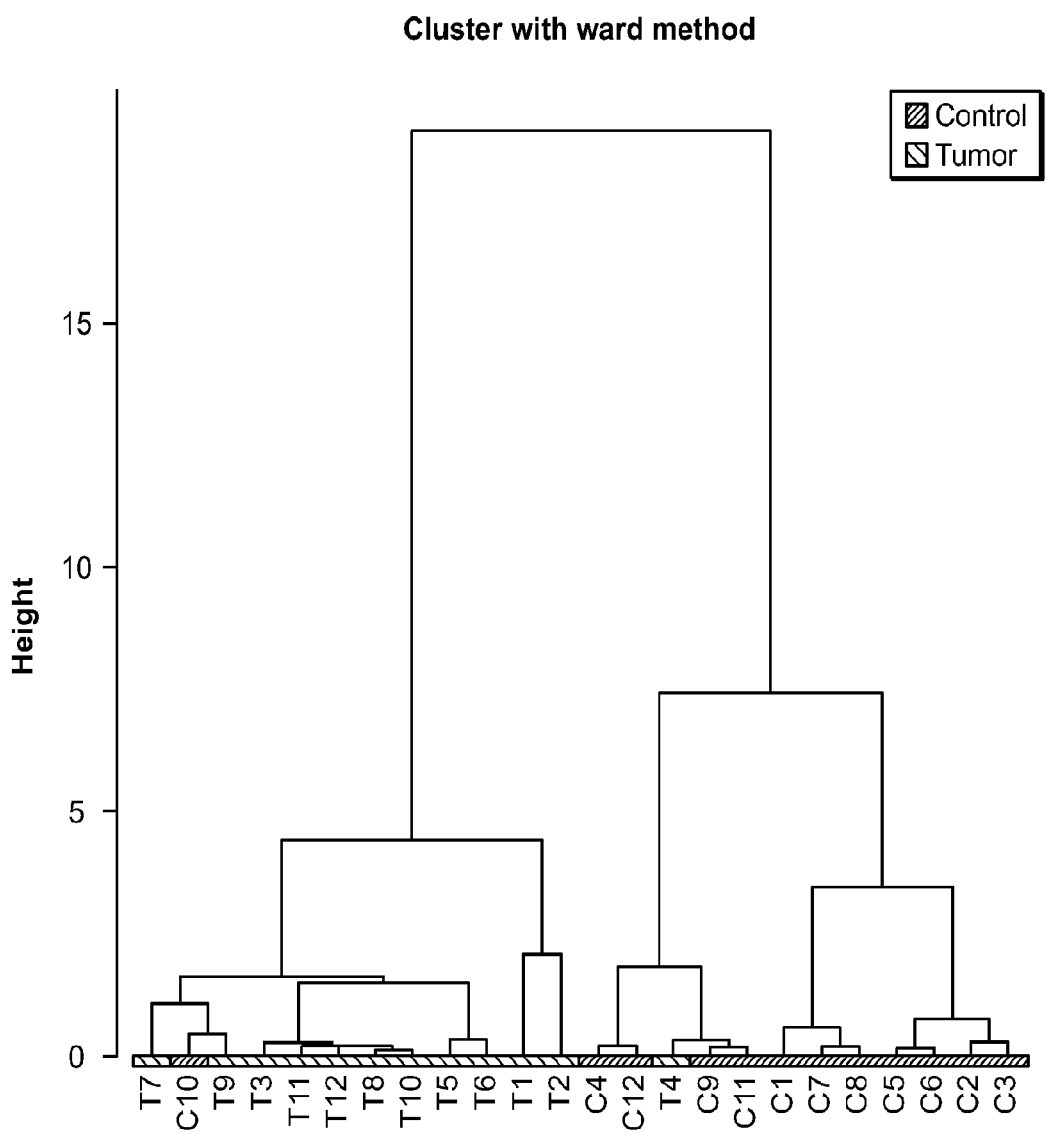

Thirteen biomarkers, related to amino acid metabolism (proline, glutamine and Nα-acetyllysine), nucleic acid metabolism (Xanthosine, inosine, deoxyuridine and thymidine) and polyamine metabolism (N1-acetylspermidine, N8-acetylspermidine and spermine) as well as methylation (asymmetric-dimethylarginine, symmetric-dimethylarginine and carnitine), were selected on the basis of their consistent and significant derangement in both cohorts (see FIGS. 8A-8D for comparison) for evaluation of predictive power using ROC analysis. Individual biomarkers (FIGS. 9A-9D) showed moderate to high (75-99%) accuracy of prediction. However, combining the biomarkers according to metabolic pathway as mentioned above showed significant improvement in (see Table 1) sensitivity as well as specificity. Consequently, biomarker panels comprising amino acid metabolites (FIG. 7B, AUCROC=0.92, sensitivity=83%, specificity=91%), polyamine metabolites (FIG. 9C, AUCROC=0.99, sensitivity=92%, specificity=100%), nucleic acid metabolites (FIG. 4D, AUCROC=1.0, sensitivity=100%, specificity=100%) and methylation metabolites (FIG. 9B, AUCROC=1.0, sensitivity=100%, specificity=100%) showed 88%, 96%, 100% and 100% accuracy of tumor diagnosis, respectively, in combined cohort at six months. The hierarchical clustering analysis (FIG. 10B) of the modulation of metabolomic signature (heatmap shown in FIG. 10A) also correctly classified all except one naïve and one tumor-bearing animal.

Figure 11:
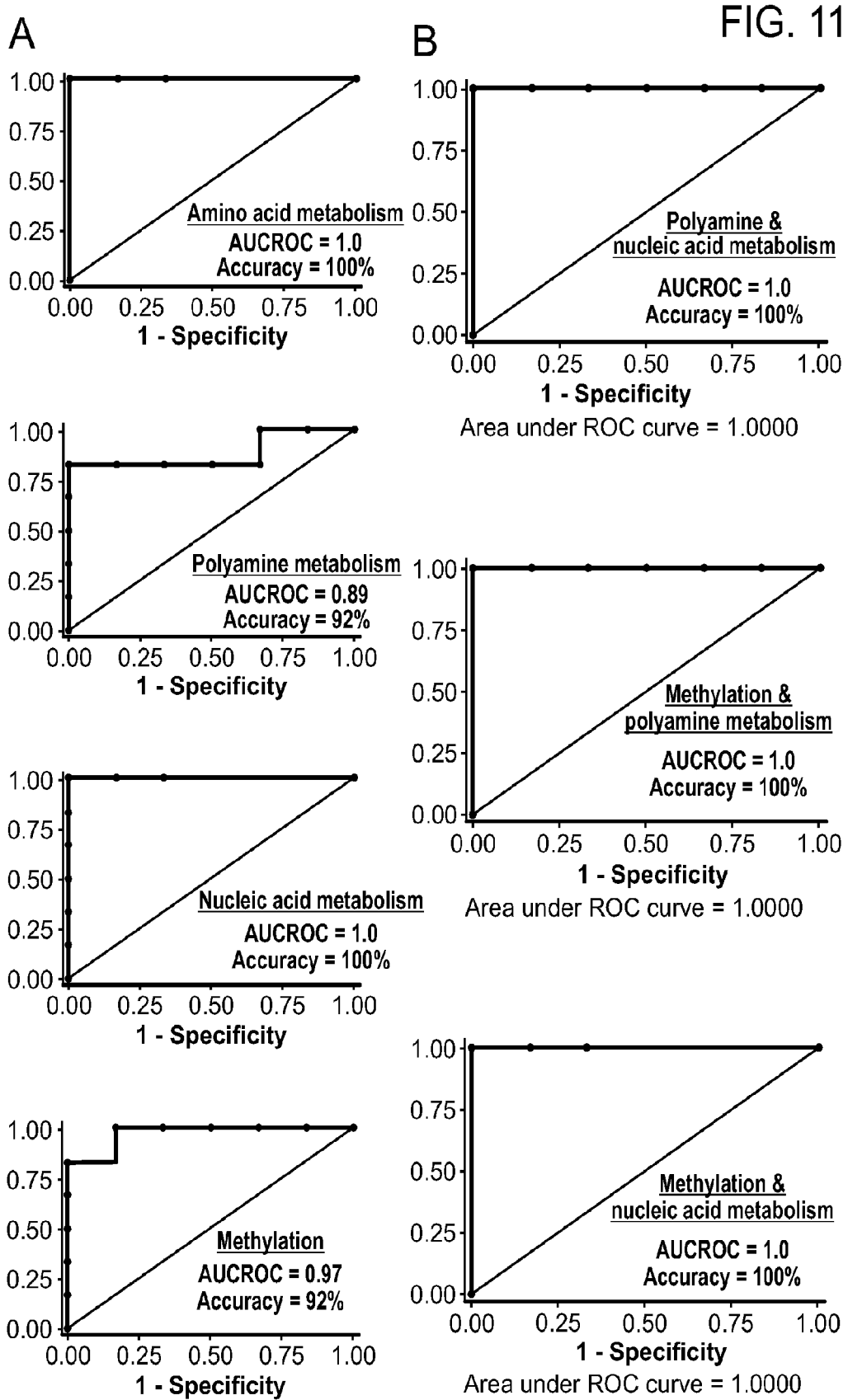
FIGS. 11A and 11B depict the ability of the biomarker panels to distinguish wild-type and mutant animals at 5 months.
Figure 12:
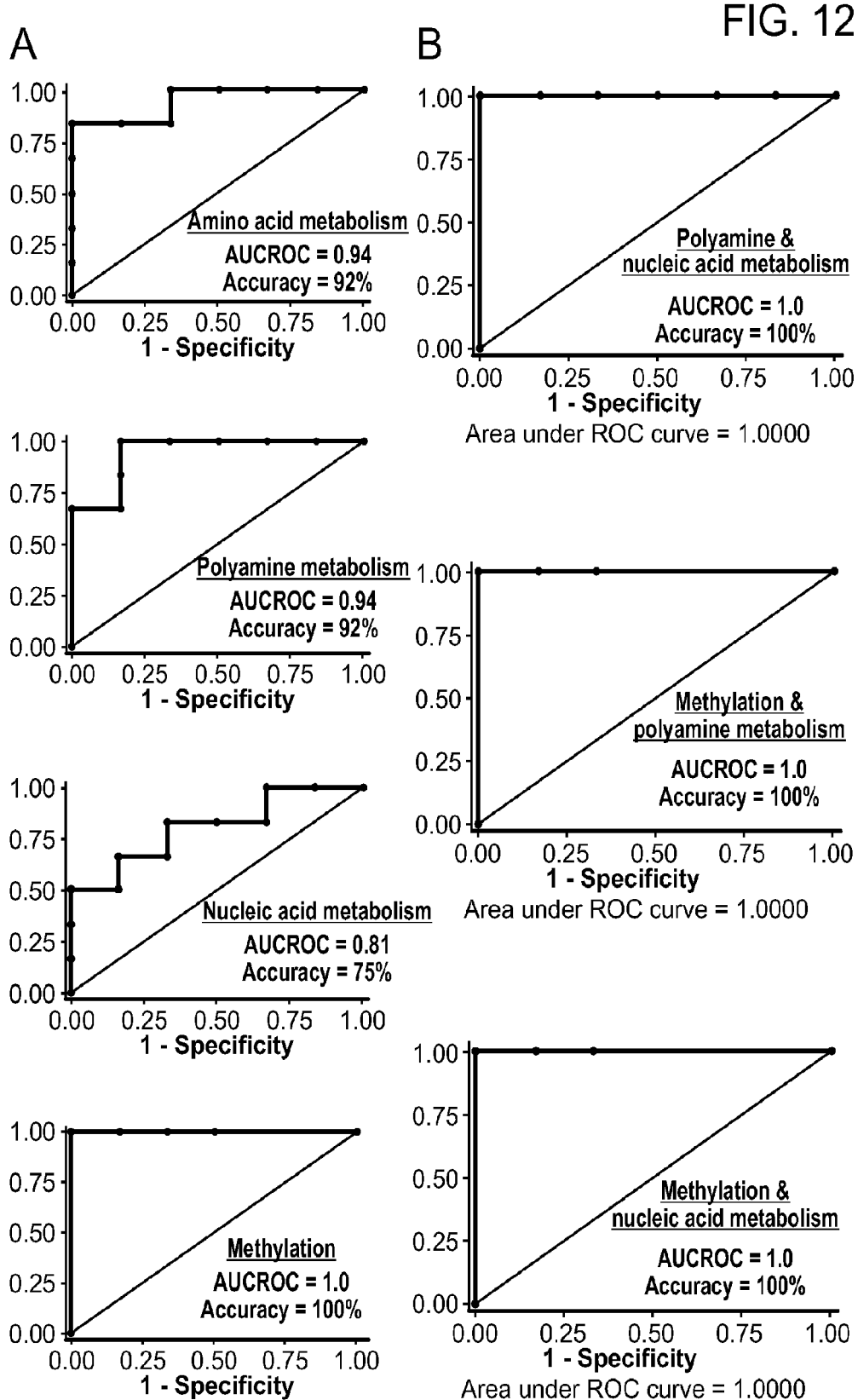
FIGS. 12A and 12B depict the ability of the biomarker panels to distinguish wild-type and mutant animals at 4 months.
Figure 13:
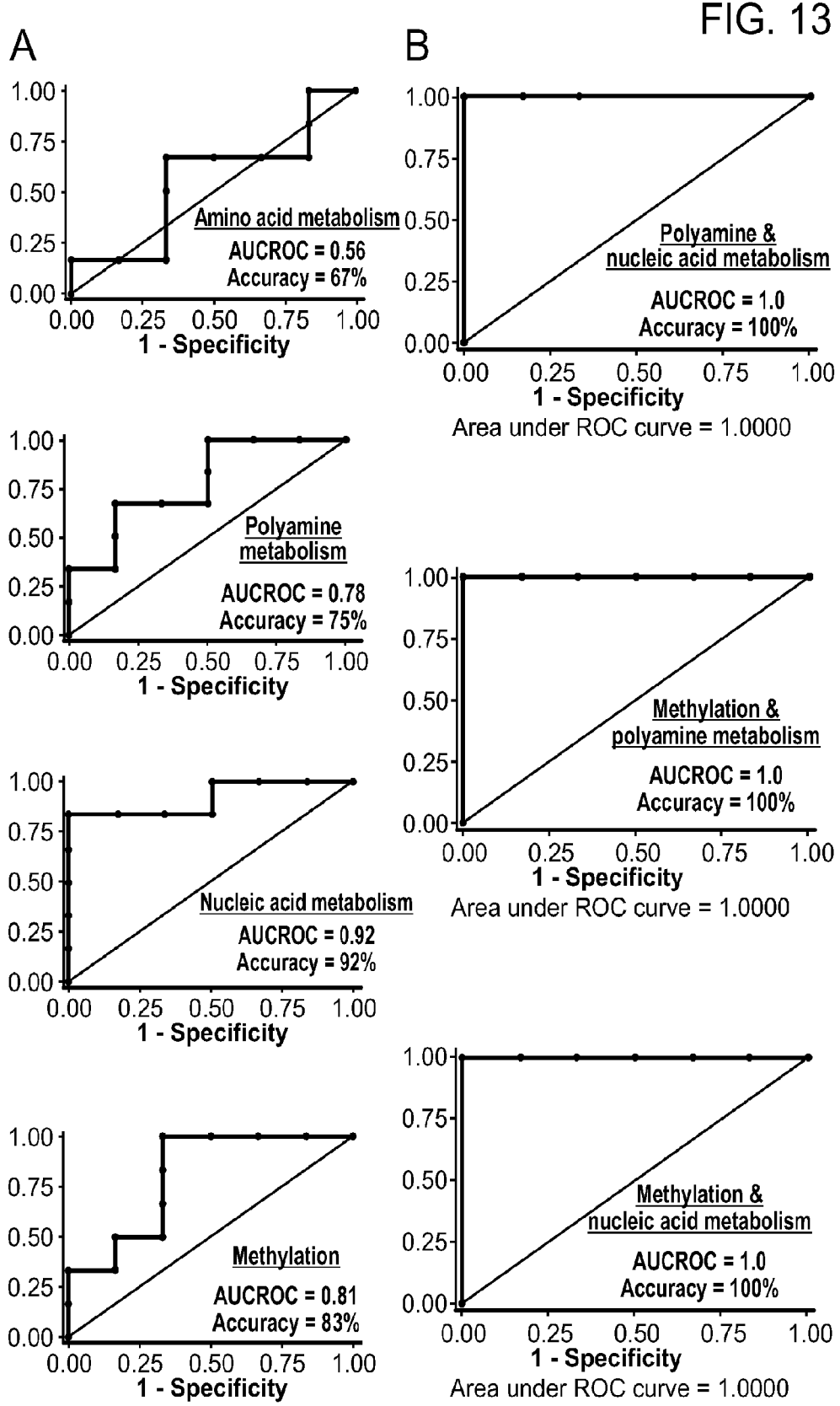
FIGS. 13A and 13B depict the ability of the biomarker panels to distinguish wild-type and mutant animals at 3 months.
Figure 14:
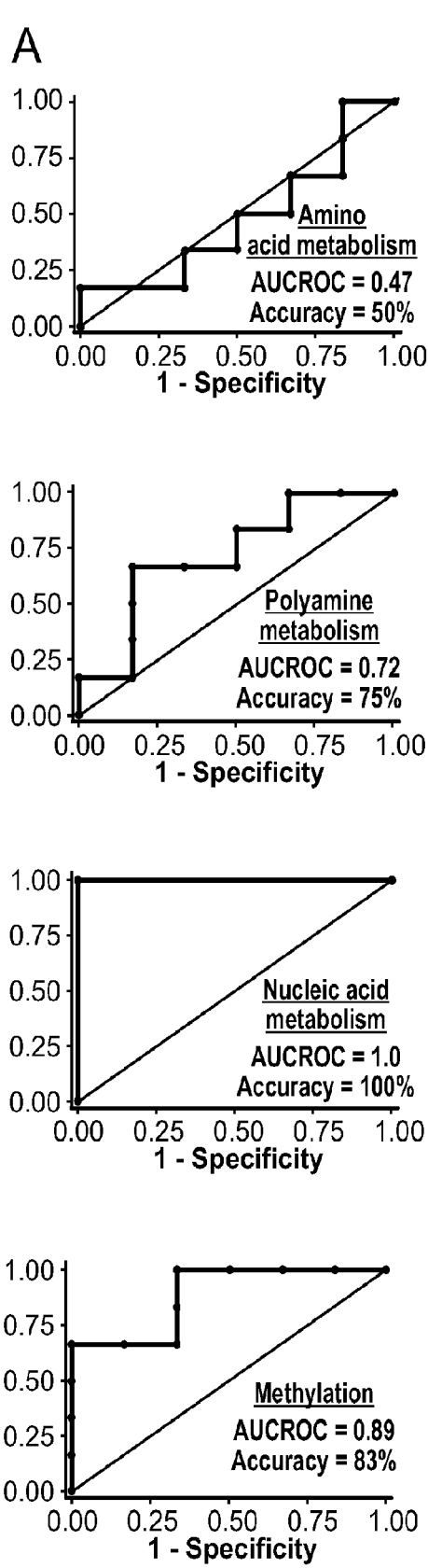
FIGS. 14A and 14B depict the ability of the biomarker panels to distinguish wild-type and mutant animals at 2 months.
Figure 14:
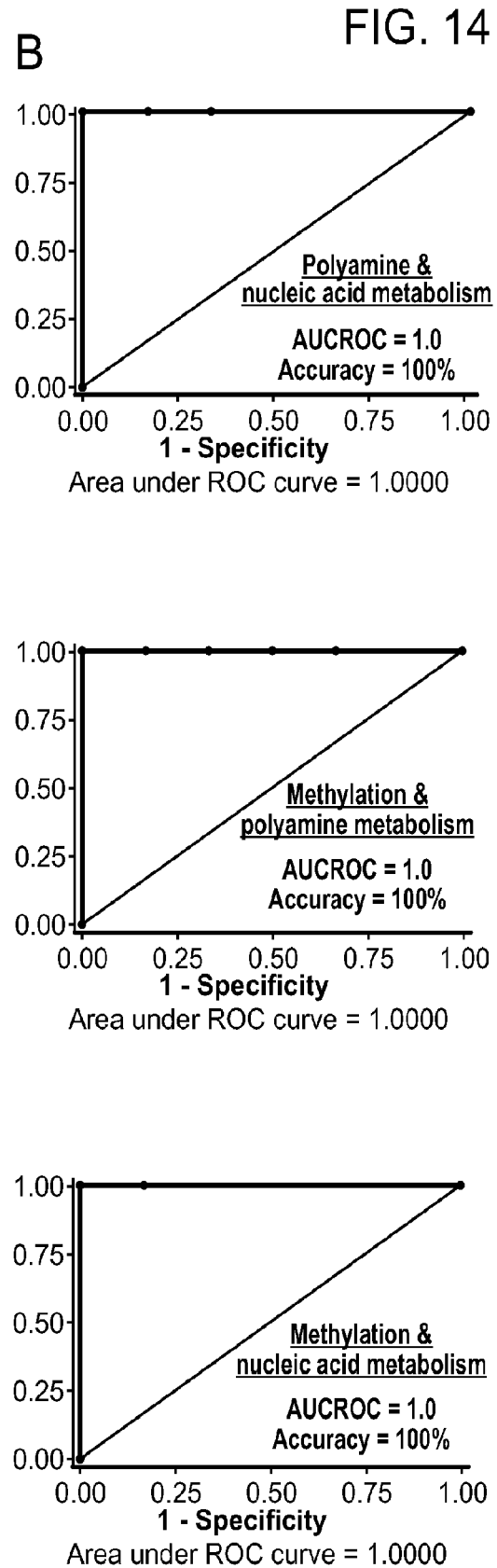

Subsequently, the ability of the biomarker panels to distinguish wild-type and mutant animals during earlier stages (5 months, FIGS. 11A and 11B; 4 months, FIGS. 12A and 12B; 3 months, FIGS. 13A and 13B; and 2 months, FIGS. 14A and 14B) of tumorigenesis were evaluated using ROC analysis. The results showed that although individual metabolites or pathways, especially, amino acid metabolism, performed poorly, any combination of biomarkers related to nucleic acid metabolism, polyamine metabolism and methylation, predicted mutant mice at risk of developing colorectal tumors with 100% sensitivity and specificity even at two months of age, when only few animals start developing tiny polyps.

Example 3. Analysis of Tissue Metabolome

Figure 15A:
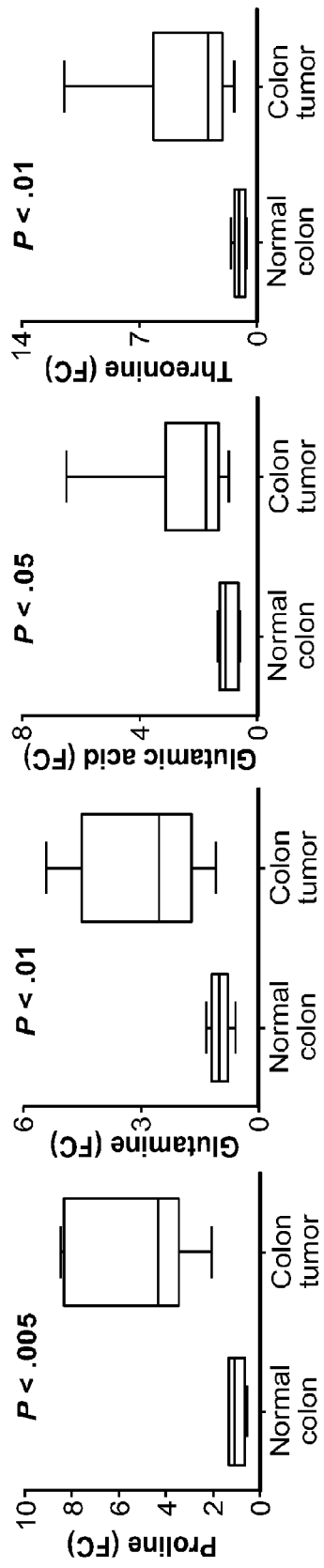
Figure 15B:
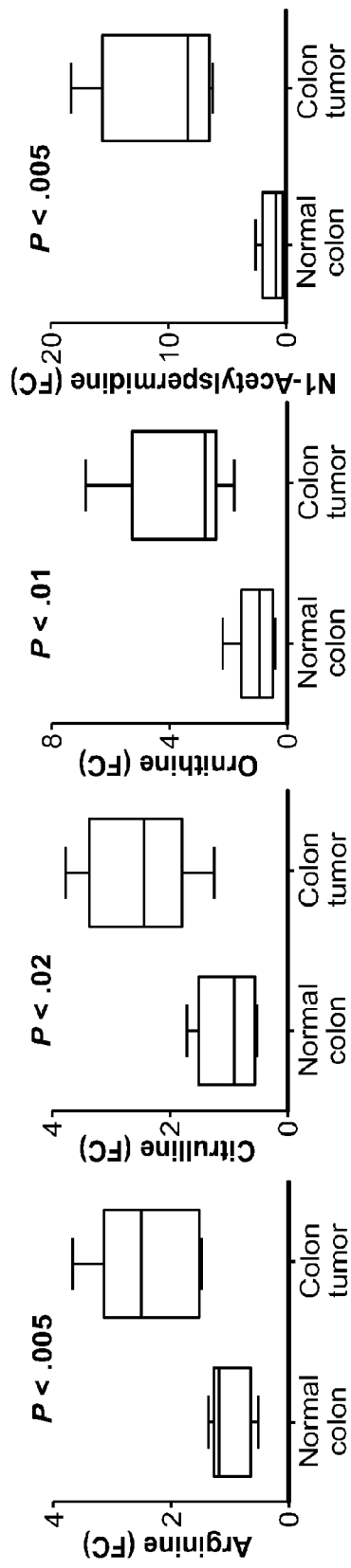

In order to examine whether changes in the urinary biomarkers correlate with changes in the tissue metabolome, the abundance of these and related metabolites were examined in colon tumor and normal colon epithelial tissue. Targeted analysis showed that the abundance of amino acids (FIG. 15A) such as proline (5.2-fold), glutamine (3.0-fold), glutamic acid (2.4-fold), and threonine (4.2-fold) were elevated in colon tumors. Metabolites related to urea cycle and polyamine metabolism (FIG. 15B) such as arginine (2.4-fold), citrulline (2.5-fold), ornithine (3.5-fold) and N1-acetylspermidine (10.3-fold) were also elevated. While metabolites related to nucleic acid metabolism (FIG. 15C) such as thymidine (2.7-fold) was elevated, the abundance of both xanthine (10.0-fold) and inosine (3.4-fold) were reduced in tumors. ATP, which is related to nucleic acid and energy metabolism, was elevated (2.9-fold) in colon tumor. Hypermethylated metabolites, dimethylarginine (3.2-fold) and carnitine (4.2-fold) were also elevated in tumor tissue.

Example 4. Analysis of Gene Expression

Figure 16:
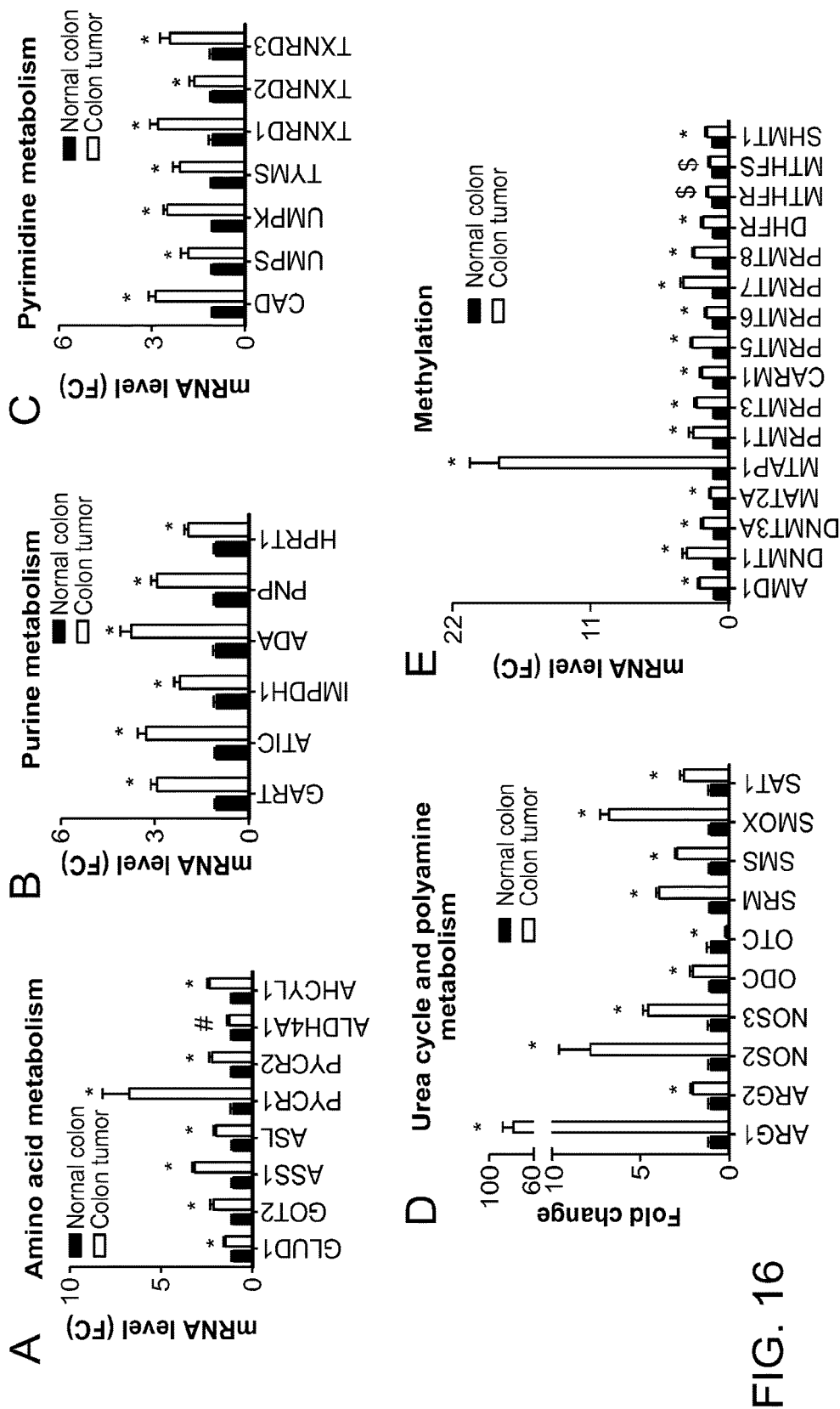
FIGS. 16A-16E depict the effect of colorectal tumorigenesis on tissue transcriptome.
Figure 17A:
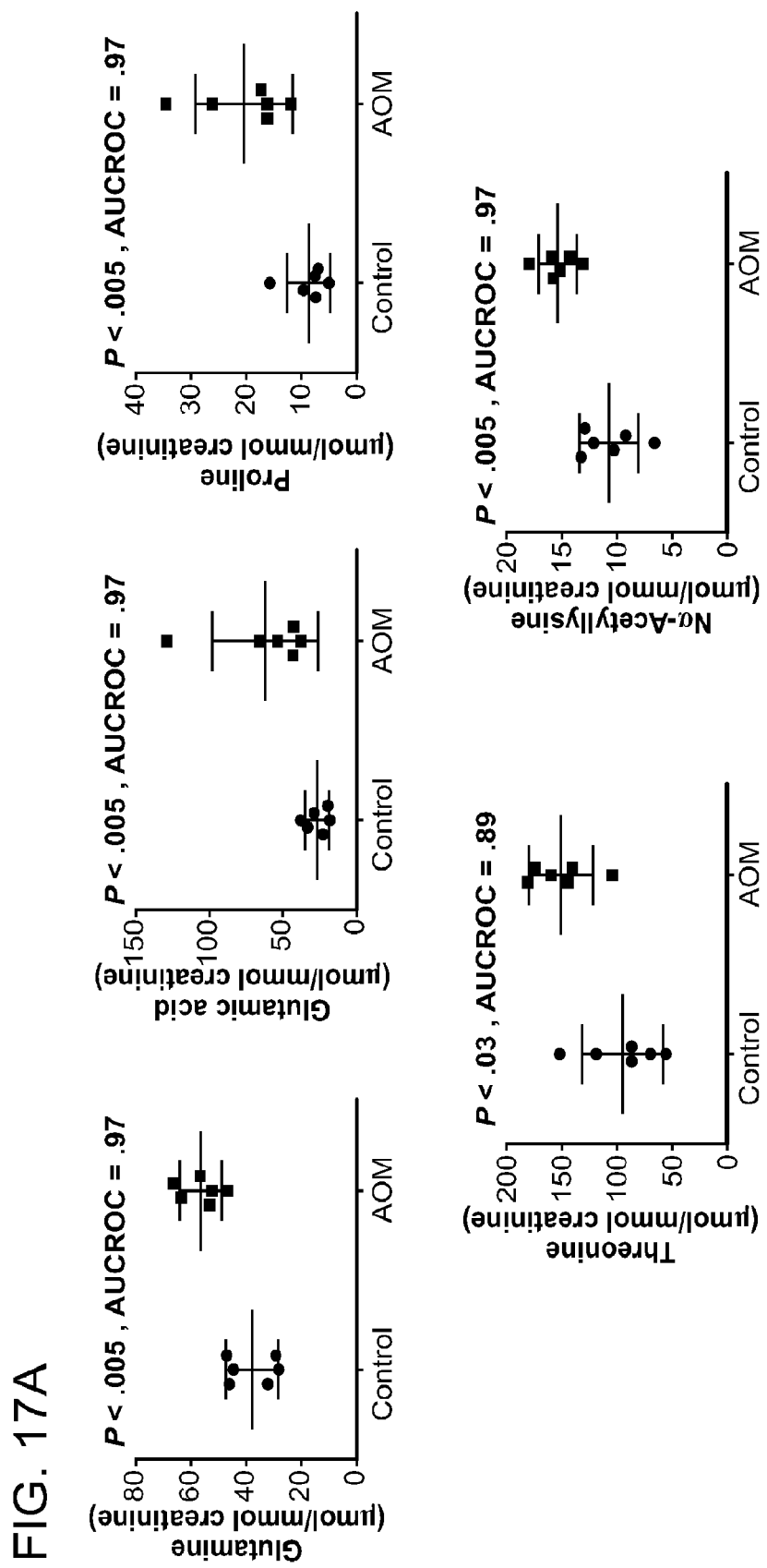
FIG. 17 A-E are a series of graphs that show changes in urinary metabolic profile associated with AOM-induced colorectal carcinogenesis in mice. Dot-scatter plots (presented as mean with 95% confidence interval) showing creatinine-normalized urinary excretion of metabolites related to FIG. 17A shows amino acid metabolism (glutamine, glutamic acid, proline, threonine, and Nα-acetyllysine)
FIG. 17B shows urea cycle and polyamine metabolism (N8-acetylspermidine, N1-acetylspermidine, citrulline, arginine, and ornithine)
FIG. 17C shows pyrimidine metabolism (deoxycytidine, cytosine, deoxyuridine, uracil, and thymidine), FIG. 17D purine metabolism (xanthine, xanthosine, and guanosine), and FIG. 17E methylation (symmetric-dimethylarginine, asymmetric-dimethylarginine, methionine, carnitine, and betaine) in saline-treated healthy (control, N=6) or tumor-bearing mice (AOM, N=6) five months after AOM-treatment. All statistical significances were calculated by two-tailed Mann-Whitney test with 95% confidence interval.
Figure 17B:
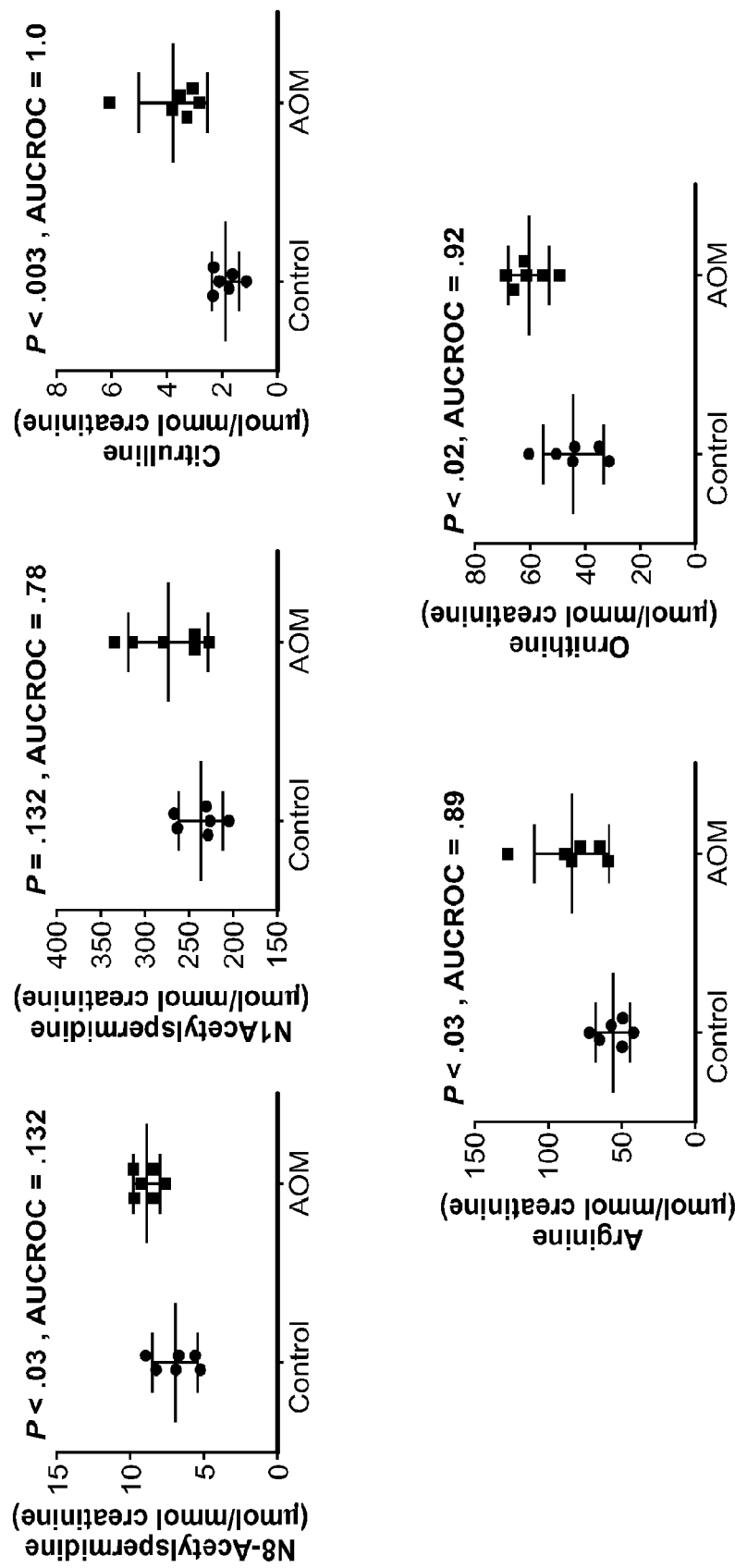
Figure 17C:
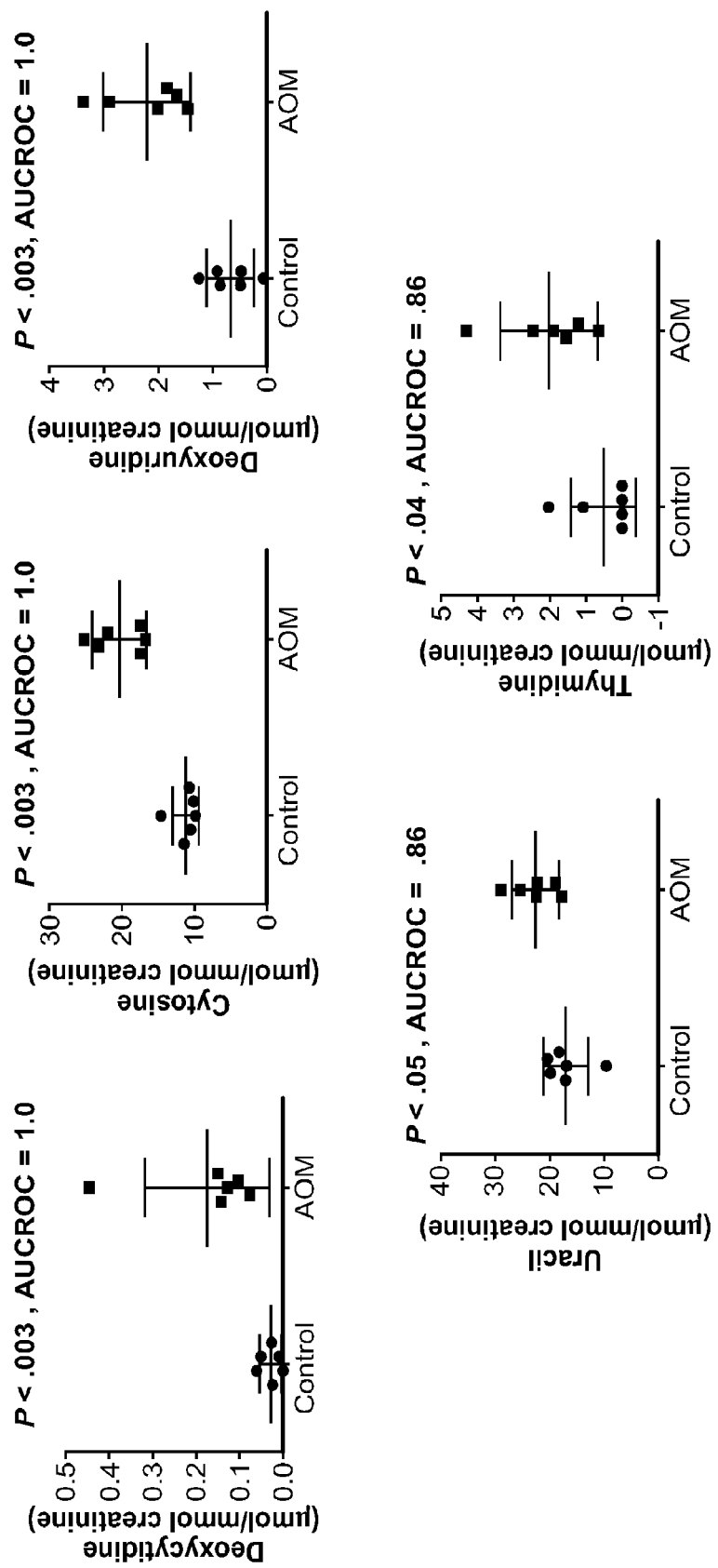
Figure 17E:
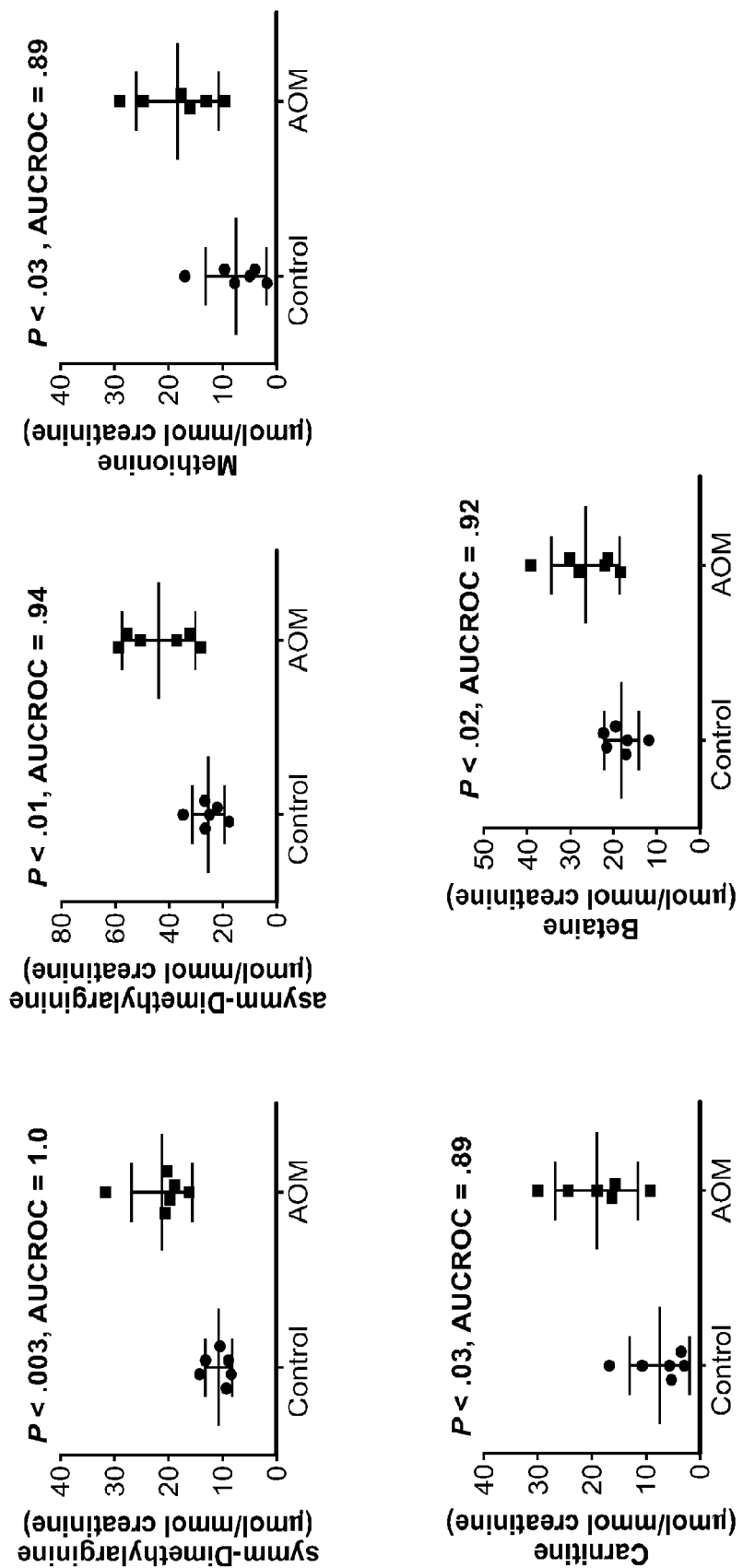

The expression of key genes (see Table 2) related to these metabolic pathways were analyzed in order to elucidate the transcriptomic changes that contributed to changes in metabolic flux and precipitated observed segregation of metabolomic traits. Messenger RNA encoding enzymes involved in de novo amino acid biosynthesis (FIG. 16A), such as GLUD1 (1.5-fold), GOT2 (2.1-fold), ASS1 (3.1-fold), ASL (2-fold), PYCR1 (6.7-fold), PYCR2 (2.2-fold), ALDH4A1 (1.3-fold) and AHCYL1 (2.3-fold) were all elevated in colon tumor. Genes involved in de novo purine biosynthesis such as GART(2.9-fold), ATIC1 (3.3-fold), IMPDH1 (2.2-fold) and metabolism such as ADA (3.7-fold), PNP (2.9-fold), HPRT1 (1.9-fold) were also elevated in tumor tissue along with genes involved in de novo pyrimidine biosynthesis such as CAD (2.9-fold), UMPS (1.8-fold), UMPK (2.5-fold), TYMS (2.1-fold), TXNRD1 (2.7-fold), TXNRD2 (1.6-fold) and TXNRD3 (2.3-fold). Messenger RNA encoding enzymes involved in urea cycle and polyamine metabolism such as ARG1 (78.5-fold), ARG2 (2-fold), NOS2 (7.8-fold), NOS3 (4.6-fold), ODC (2.1-fold), SRM (5-fold), SMS (2.9-fold), SMOX (6.7-fold), and SAT1 (2.5-fold) were elevated whereas OTC (8.2-fold) was reduced. A whole host of mRNAs related to post-translational and epigenetic methylation machinery such as DNMT1 (3.3-fold), DNMT3A (2-fold), PRMT1 (2.7-fold), PRMT3 (2.5-fold), CARM1 (2.1-fold), PRMT5 (2.8-fold), PRMT6 (1.6-fold), PRMT7 (3.5-fold), PRMT8 (2.6-fold), AMD1 (2.4-fold), MAT2A (1.4-fold), MTAP1 (18.2-fold), DHFR (1.9-fold), MTHFR (1.5-fold), MTHFS (1.3-fold) and SHMT1 (1.6-fold) were also elevated.

Example 5. Changes in Amino Acid, Nucleic Acid, and Polyamine Metabolism and Methylation in Tumor Tissue Accompany Neoplasia Metabolomic and transcriptomic analysis revealed changes in amino acid, nucleic acid, polyamine metabolism and methylation in tumor tissue. Changes in the urinary metabolome were found to be in concert with these changes and, consequently, helped to correctly distinguish healthy and tumor-bearing animals. The consistency of longitudinal trait of simultaneous deregulation of these pathways during tumorigenesis resulted in highly accurate and early prediction of subjects at risk of developing colorectal cancer in this mouse model.

Growth and proliferation are hallmarks of cancer cells. Loss-of-function APC mutation leads to activation of Wnt-signaling target genes such as c-Myc, which is a master regulator of genes involved in these processes. Growth demands building blocks for macromolecules and energy, which come from nutrients. It was shown that cancer cells develop an ability to increase nutrient (glucose, glutamine and fatty acid) uptake. In fact, the accumulation of essential amino acids such as threonine in colon tumors of $APC^{Min/+}$ mice indicated development of a similar capability. In order to extract energy from nutrients cancer cells resort to a variety of metabolic reprogramming ranging from increased glycolysis (Warburg effect), Krebs cycle to fatty acid oxidation. The present results showed that urinary carnitine excretion was lower whereas tumor tissue carnitine concen-

TABLE 2

| Gene | Full name | Reaction | Forward primer | Reverse primer |
|---|---|---|---|---|
| CAD | carbamoyl phosphate synthetase | 2 ATP + L-glutamine + HCO3- + H2O = 2 ADP + phosphate + L-glutamate + carbamoyl phosphate | TGGGAGTTGCATGAAGAGTG | TACGCAGTTCTCTCGACCA |
| CAD | aspartate carbamoyltransferase | carbamoyl phosphate + L-aspartate - phosphate + N-carbamoyl-L-aspartate | | |
| CAD | carbamoylaspartic dehydrase | (S)-dihydroorotate + H2O = N-carbamoyl-L-aspartate | | |
| UMPS | orotate phosphoribosyl-transferase | orotidine 5'-phosphate - UMP + CO2 | CTCCTCCCCAGTCTACATCG | AAACTGATCCCCGCATTTTT |
| UMPS | orotidine-5'-phosphate decarboxylase | orotidine 5'-phosphate + diphosphate = orotate + 5-phospho-alpha-D-ribose 1-diphosphate | | |
| UMPK | UMP-CMP kinase | ATP + UMP = ADP + UDP | CTTCCTGATCGGCGTGAG | CCTGCTTCTGGTGGTAATCC |
| TXNRD1 | thioredoxin reductase 1 | thioredoxin + NADP + = thioredoxin disulfide + NADPH + H+ | GAGCTGGTGGTTTCACCTTC | GGTCGAAGTCATAGGACCCA |
| TXNRD2 | thioredoxin reductase 2 | thioredoxin + NADP + = thioredoxin disulfide + NADPH + H+ | GCTTCTGGCAAGGAAGACAC | CCAGCCTTCTCCAGATTCAA |
| TXNRD3 | thioredoxin reductase 3 | thioredoxin + NADP + = thioredoxin disulfide + NADPH + H+ | TTACTGTCCACACAGCACGC | ACTTCCTGAACACTGGCCC |
| TYMS | Thymidilate synthetase | methylenetetrahydrofolate + dUMP =dihydrofolate + dTMP | GAGGCATTTTGGAGCAGAGT | TCAGGGTTGGTTTTGATGGT | trations were higher. Without being bound to a particular theory, this indicates an active retention of carnitine in tumors, presumably to shuttle fatty acids into mitochondrial for β-oxidation to produce energy. It was shown that Wnt-signaling promotes mitochondrial biogenesis via c-Myc, which increases acetyl-CoA production. Therefore, elevated acetylated urinary biomarkers (Nα-acetyllysine and acetyl-spermidines) may be a reflection of c-Myc activation in tumor tissue. Acetyl-CoA can either enter the Krebs cycle or de novo fatty acid synthesis, which is required for cell growth and has been shown to be upregulated in cancer. Mitochondrial Krebs cycle plays an important role in energy production and de novo synthesis of amino acids. Reducing equivalents produced via fatty acid oxidation or Krebs cycle can either be used in fatty acid biosynthesis or to produce ATP via mitochondrial oxidative phosphorylation. c-Myc activation was shown to increase oxidative phosphorylation. The concentration of ATP was indeed found to be higher in tumors.

The gene (GOT2) encoding the mitochondrial anaplerotic enzyme involved in transamination of aspartate and glutamate (1) was found to be overexpressed in tumors. Aspartate is involved in ATP-dependent biosynthesis and regeneration of arginine through urea cycle. The genes involved in this process such as ASS1 and ASL (6) were elevated in tumors. Consequently, arginine concentration in tumors was found to be higher than normal colon. The transamination of oxaloacetate to aspartate requires glutamate with concomitant production of α-ketoglutarate, which can contribute to the biosynthesis of non-essential amino acids via the Krebs cycle. Glutamate can be produced from glutamine, which was significantly elevated in tumor tissue, by glutaminase. c-Myc was shown to increase the production of glutamate without any change in glutaminase expression via suppression of miR-23. Glutamate can also be converted to α-ketoglutarate by GLUD1, which was found to be upregulated in tumors. Glutamate is a precursor to the biosynthesis of proline and the genes involved in this pathway such as ALDH4A1 and PYCR1, PYCR2 were overexpressed in tumors. Consequently, both tissue abundance and urinary excretion of proline was elevated tumor-bearing mice. The transcriptomic and metabolomic enrichment of these pathways, which might be the result of c-Myc activation, reflect hyperactive central carbon metabolism, energy metabolism and de novo amino acid biosynthesis to support growth of colon cancer cells in APC$^{Min/+}$ mice.

Cell proliferation, on the other hand, requires the synthesis of genetic material. It was shown that glutamine plays a central role in c-Myc driven proliferation. Apart from glutamine and ATP, de novo nucleotide synthesis also requires 5-phosphoribosyl 1-pyrophosphate (PRRP), which is synthesized via pentose phosphate pathway (PPP) with concomitant production of NADPH. c-Myc was shown to increase flux through PPP. The present study showed that the expression of genes involved in funneling increased carbamoyl phosphate and PPP flux into purine biosynthesis, such as GART and ATIC, were elevated in colon tumors. In addition, the expression of genes involved in purine interconversion and metabolism such as IMPDH1, ADA, PNP, and HPRT1, were also elevated in tumors. IMPDH1 was shown to be a direct c-Myc target and inhibition of this gene was found to inhibit proliferation. These resulted in the elevation of inosine, xanthosine and xanthine in urine. However, inosine and xanthine were reduced in the tissue, presumably due to the interconversion and/or excretion through urine.

The expression of CAD, another direct target of c-Myc, that encodes a protein with triplet enzymatic activity required for biosynthesis of pyrimidines from glutamine, aspartate and ATP, was elevated in tumors. In addition, the expression of UMPS and UMPK, genes involved in converting PRRP and orotic acid into uridine triphosphate, were also elevated. Uridine triphosphate is the precursor of other pyrimidine nucleotides required for RNA and DNA synthesis. In line with the elevated de novo synthesis flux of pyrimidine nucleotides, excretion of cytidine was found to be elevated in urine. In addition, all three isoforms of thioredoxin reductase, the enzymes involved in synthesis of deoxyribonucleotides, were overexpressed along with TYMS, the gene involved in the synthesis of DNA-specific thymidine nucleotide. As a result, tissue distribution of thymidine as well as urinary excretion of thymidine and deoxyuridine was significantly elevated in tumor-bearing animals. These observations reflect a hyperactivation of RNA and DNA biosynthesis, an essence of proliferative capacity, via synchronized redistribution of central metabolic flux towards PPP and amino acid biosynthesis.

A significant amount of central metabolic flux was also directed towards urea cycle via aspartic acid mediated arginine biosynthesis. However, the arginases were also highly expressed in tumor tissue along with nitric oxide synthases NOS2 and NOS3 that produce citrulline and nitric oxide. Consequently citrulline was found to be elevated in both tumor tissue and urine. Arginase, which produces ornithine, was already shown to be increased in human colorectal cancer tissue. Ornithine can be converted to either citrulline by Ornithine transcarbamylase (OTC) to re-enter the urea cycle or putrescine byornithine decarboxlyase (ODC). The ODC expression was upregulated in tumor with concomitant downregulation of OTC expression that would result in funneling of ornithine into biosynthesis of putrescine. This indicates that the arginine pool is channelized in bifurcated fashion into both urea cycle (via NOS) and polyamine biosynthesis (via ODC). The next step in polyamine biosynthesis involves successive addition of propylamine groups from S-adenosylmethioninamine (SAMA) by SRM to produce spermidine and then, by SRM or SMS to produce spermine. The expression of both enzymes was elevated in tumors that also showed elevated expression of SMOX that reverts spermine to spermidine with concomitant production of $H_2O_2$. This should lead to a build-up of spermidine in tumors. Instead, a marked increase in N8-acetylspermidine in urine and N1-acetylspermidine in tumor and urine was observed in APC$^{Min/+}$. This could be rationalized by the elevated production of acetyl-CoA and increase in expression of SAT1 in tumors. Both of these metabolites were earlier shown to be elevated in the urine of colorectal cancer patients. Polyamines are known to epigenetically modulate gene expression and promote proliferation. ODC, the key enzyme involved in determining the flux into polyamine biosynthesis, was shown to be a direct c-Myc target. Interestingly, polyamines were also shown to induce c-Myc overexpression by perturbing chromatin structure. Thus, these results suggest that activation of Wnt-signaling can direct central carbon flux is directed towards polyamine biosynthesis and epigenetically promote proliferation. It was interesting to note that the expression of MTAP that converts S-methyl-5'-thioadenosine (MTA), the product propylamine transfer from SAMA, into adenine was also increased in tumors. This might, in turn, contribute to the observed increase in purine metabolites in tissue and urine.

Epigenetic modulation of gene expression, particularly, downregulation of tumor suppressor genes, plays an important role in tumorigenesis. These mechanisms involve methylation of DNA as well as methylation and acetylation of arginine and lysine residues of histone. c-Myc has also been shown to influence DNA methylation. An increase in the expression of DNA methyltransferases (DNMT1, DNMT3A) was observed in colon tumors in APC$^{Min/+}$ mice. These enzymes transfer methyl group from S-adenosylmethionine (SAM) to cytosine of CpG islands upstream of the target gene. SAM is converted to S-adenosylhomocysteine in the process, which eventually gets reconverted to SAM via homocysteine and methionine. Genes involved in the process, AHCYL1 and MAT2A were upregulated in tumors. This process requires ATP as well as 5-methyltetrahydrofolate that is derived from folic acid. Another folic acid metabolite, 5,10-methylenetetrahydrofolate, is also involved in thymidine synthesis by TYMS, which was significantly elevated. Purine biosynthetic enzyme GART, which was elevated in tumors, also requires 10-formyltetrahydrofolate. These results indicate funneling of carbon flux into folate-mediated one-carbon transfer machinery. Folic acid fortification has been shown promote colorectal cancer. c-Myc has earlier been shown to increase central carbon flux into one carbon pool and induce genes involved in folate metabolism. Genes involved in folate metabolism such as DHFR, MTHFR, MTHFS (ATP-dependent), and SHMT1 were, indeed, overexpressed in tumors. SHMT1 also participates in biosynthesis of serine. In addition, the gene AMD1 involved in conversion of SAM to SAMA, which drives polyamine biosynthesis, was also elevated in colon tumors. These observations indicate to hyperactive methylation machinery in colon tumors.

In addition to DNA methylation, post-translational modification of protein lysine and arginine residues also plays an important role in the epigenetic regulation of gene expression and modulation of protein activity. Carnitine is produced as a result of trimethylation of protein lysine residues. It was recently shown that trimethylation of lysine residues are involved in regulation of expression of Wnt-signaling target genes. The increase in abundance of carnitine indicates that increase in SAM-dependent lysine methylation might contribute to aberrant gene expression patterns in APC$^{Min/+}$ colon tumors. In addition, the expression and activity of protein arginine methyltransferases (PRMTs) were also elevated. PRMTs transfers methyl groups from SAM to arginine side chains of histones and, thereby, modulate their nucleosome binding affinity to regulate gene expression. While type-I PRMTs typically activates gene expression, type-II PRMTs repress them and they act on different sites. PRMTs can regulate the transcriptional activity of a number of genes, including P53, NF-κB and E2F1 that play important role in tumorigenesis by regulation of downstream signaling for cell survival and proliferation. In addition, arginine methylation also post-translationally modulates the activity of a host of other proteins involved in processes like RNA processing, signal transduction and DNA repair. Arginine residues are methylated either symmetrically (by type-I PRMTs such as PRMT1, PRMT3, CARM1, PRMT6) or asymmetrically (by type-II PRMTs such as PRMT5, PRMT7) to produce symmetric or asymmetric dimethylarginine. The expression of all of these genes was upregulated along with Prmt8, which was recently shown to interact with hnRNPs and RNA-helicases, in the tumor tissue. Consequently, the abundance of dimethylarginines in tumor tissue as well as their excretion in the urine was significantly elevated. Wnt-signaling has been shown to cause arginine methylation of G3BP1 that acts as a molecular switch for fi-catenin activity. Thus, increased arginine methylation due to activation of Wnt-signaling may compound the activation of the proliferative signal and viciously accelerate tumorigenesis.

The results described herein revealed a concerted deregulation of epigenetic, transcriptional, post-translational and metabolic events associated with tumorigenesis in APC$^{Min/+}$ mice. The existing literature suggests that c-Myc can directly contribute to many of these events. However, it remains unclear why all cells harboring APC mutation do not turn into cancer cells. It was proposed that colorectal carcinogenesis is a multi-step process where inflammation and mutagenesis plays the role of a promoter following mutation (genetic or somatic) in a tumor suppressor (such as APC) gene. Increase in production of reducing equivalents (via fatty acid oxidation, TCA cycle and PPP) and oxidative phosphorylation by c-Myc can significantly increase reactive oxygen species (ROS) production. In addition, the activities of ROS-generating metabolic processes, such as oxidation of spermine to spermidine or hypoxanthine to xanthine, were elevated in tumor tissue. Chronic elevation of ROS production can increase inflammation, DNA damage and mutation which keeps accumulating stochastically in cells in a time-dependent manner. ROS production can also induce antioxidant response in cancer cells and prevent apoptosis as well as accelerate ageing-autophagy in tumor microenvironment that helps to feed cancer cells. These may augment the activation of Wnt-signaling due to the APC mutation and promote tumorigenesis in a time-dependent, yet stochastic manner. Taken together, these observations suggest that c-Myc can simultaneously drive inflammation as well as genetic and epigenetic aberrations to precipitate redistribution of metabolic flux towards de novo biosynthesis of amino acids, nucleic acids, polyamines and energy production to promote growth and proliferation.

Without being bound to a particular theory, the results described herein indicate that a coordinate reprogramming of cellular metabolism during tumorigeneis is reflected in the urine metabolome. In particular, progressive elevation of symmetric- and asymmetric-dimethylarginine in urine of animals as a reflection of hyperactive methylation machinery is a novel observation in the context of colorectal cancer. The ability of urinary metabolites to prospectively identify subjects that would eventually develop tumor, indicate combined panel of urinary biomarkers representing synchronized deregulation of amino acid, nucleic acid, polyamine metabolism and methylation has the potential to provide a powerful high-throughput noninvasive method for screening as well as early diagnosis of colorectal cancer.

Example 6. Validation of Urinary Metabolic Signatures in Mouse Model of Sporadic Colorectal Cancer The following examples further demonstrate the utility of metabolic biomarkers belonging to methylation, urea cycle and polyamine metabolism, nucleic acid metabolism and amino acid metabolism in early noninvasive screening and diagnosis of colorectal cancer.

In order to examine whether the noninvasive signatures associated with colorectal tumorigenesis identified in hereditary colorectal cancer mouse model (Apc$^{Min/+}$) is, in general, etiology-independent biomarkers of colorectal cancer, these metabolites were measured in the urine of mouse model of AOM-induced sporadic colorectal carcinogenesis.

Similar to that observed in Apc$^{Min/+}$ mice, AOM-treated mice also show (FIG. 17) elevated excretion of glutamine, proline, Nα-acetyllysine, N8-acetylspermidine, citrulline, deoxyuridine, thymidine, symmetric-dimethylarginine, and asymmetric-dimethylarginine (FIG. 17). Although not statistically significant, xanthine (P=0.065), xanthosine (P=0.132) and N1-acetylspermidine (P=0.132) showed a trend of elevation (Supplementary FIG. 19). In addition, it also showed elevation of glutamic acid, threonine, deoxycytidine, cytosine, guanosine, betaine, methionine (FIG. 17). However, unlike $Apc^{Min/+}$ mice it showed an increase in excretion of ornithine and carnitine. Nevertheless, the overall metabolic signature indicated a concerted dysregulation of the aforementioned metabolic pathways similar to $Apc^{Min/+}$ mice. This indicated that such derangements may be a common feature of colorectal carcinogenesis irrespective of etiological heterogeneity as found in human subjects. The fact that even the genetic background of AOM-treated mice (129P3/J) and $Apc^{Min/+}$ mice (C57/BL6J) were different strongly indicates to the robustness of association of these signatures with colorectal carcinogenesis.

Accordingly, based on the foregoing results, it can be concluded that derangement of urinary excretion of metabolites related to methylation, urea cycle and polyamine metabolism, nucleic acid metabolism and amino acid metabolism is a general phenomenon associated with hereditary as well as sporadic colorectal cancer.

Figure 18A:
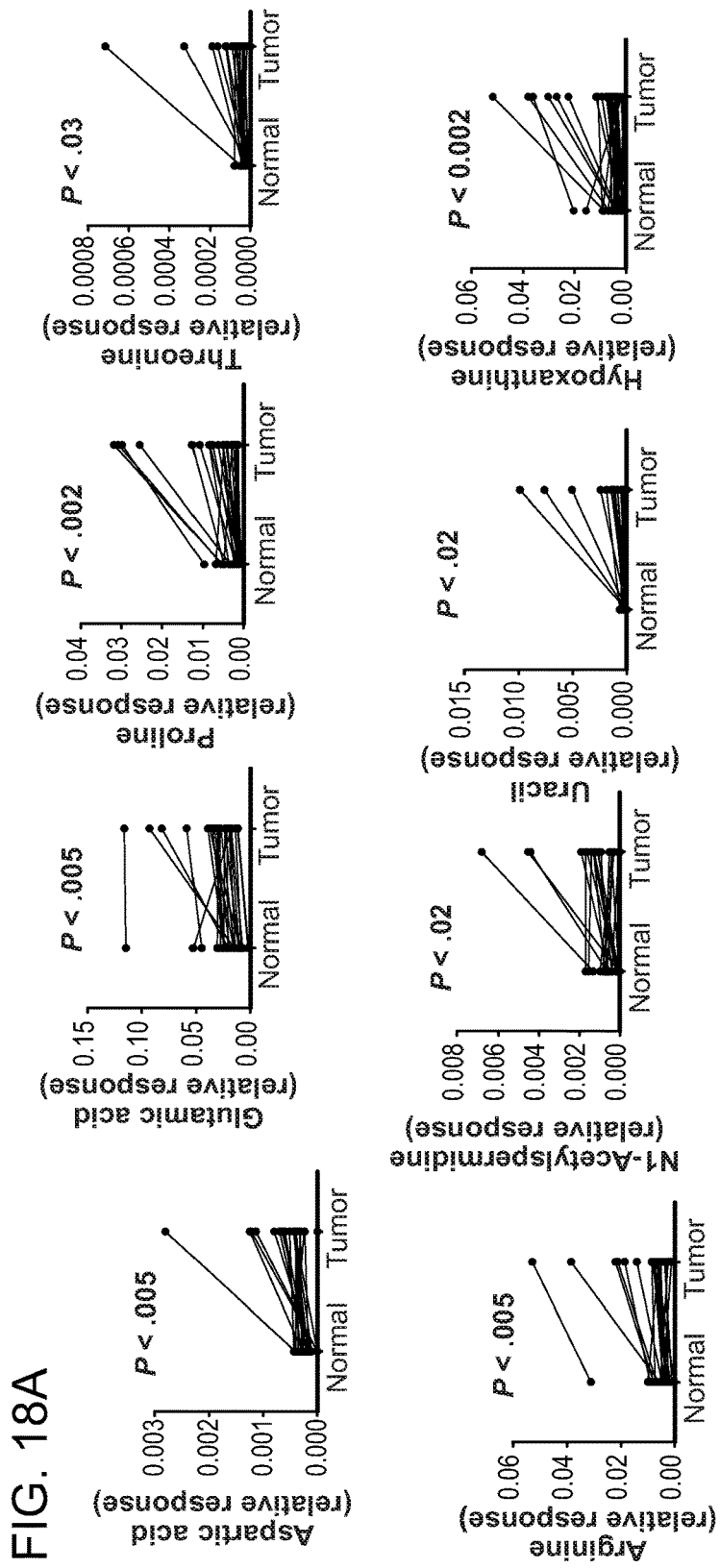
FIGS. 18A and 18B are a series of graphs that show the effect of colorectal tumorigenesis on the metabolome of human epithelial tissue. Arrow plots showing changes in metabolite abundance between paired colon tumor and adjacent non-tumor tissue. All cases (N=23) with tumors found in rectum and sigmoidal, descending or transverse colon are presented. P values were calculated by two-tailed paired t-test with 95% confidence intervals.
Figure 18B:
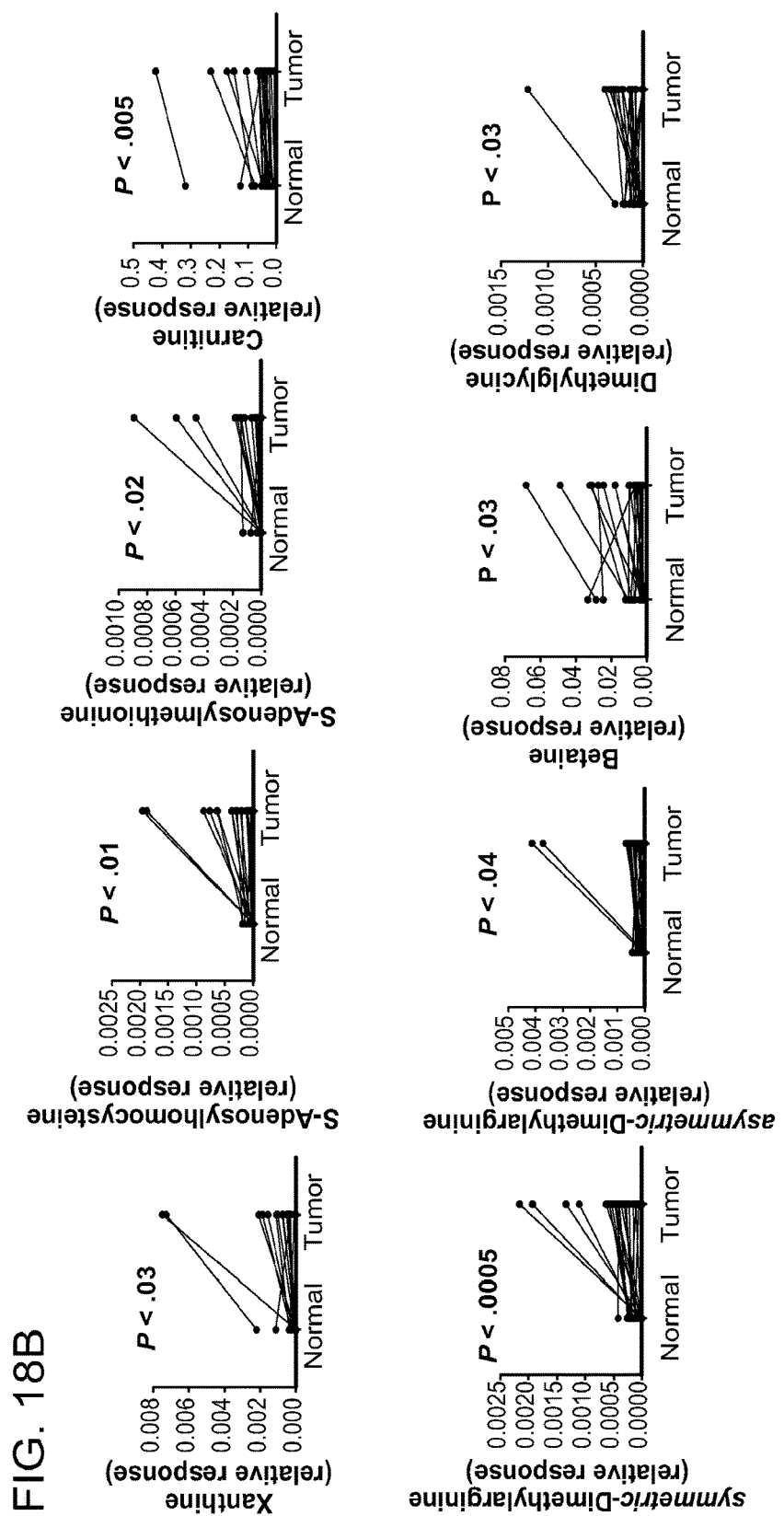
Figure 19A:
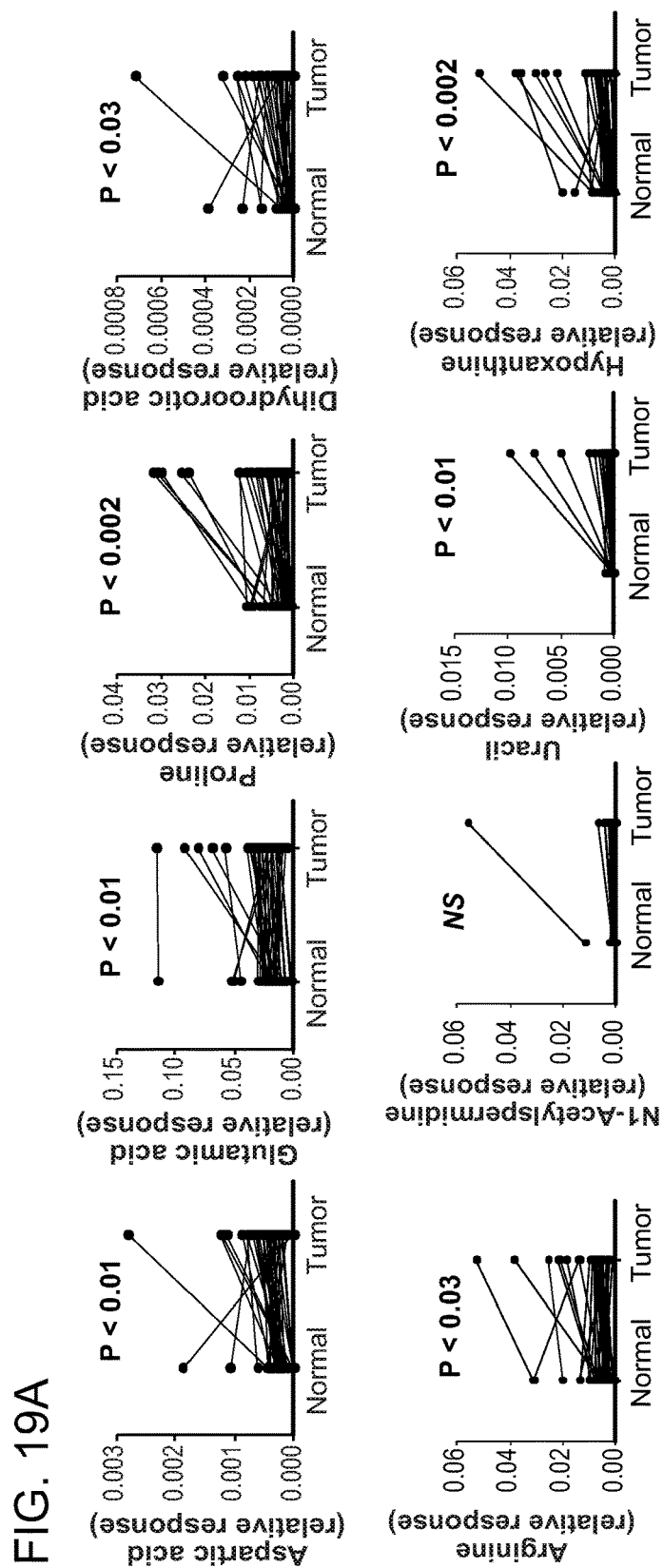
FIGS. 19A and 19B are a series of graphs that shows the effect of colorectal tumorigenesis on the metabolome of human epithelial tissue. Arrow plots showing changes in metabolite abundance between paired colon tumor and adjacent non-tumor tissue. All tumors (N=39) are presented irrespective of location and histology. Statistical significance was calculated by two-tailed paired t-test with 95% confidence intervals.
Figure 19B:
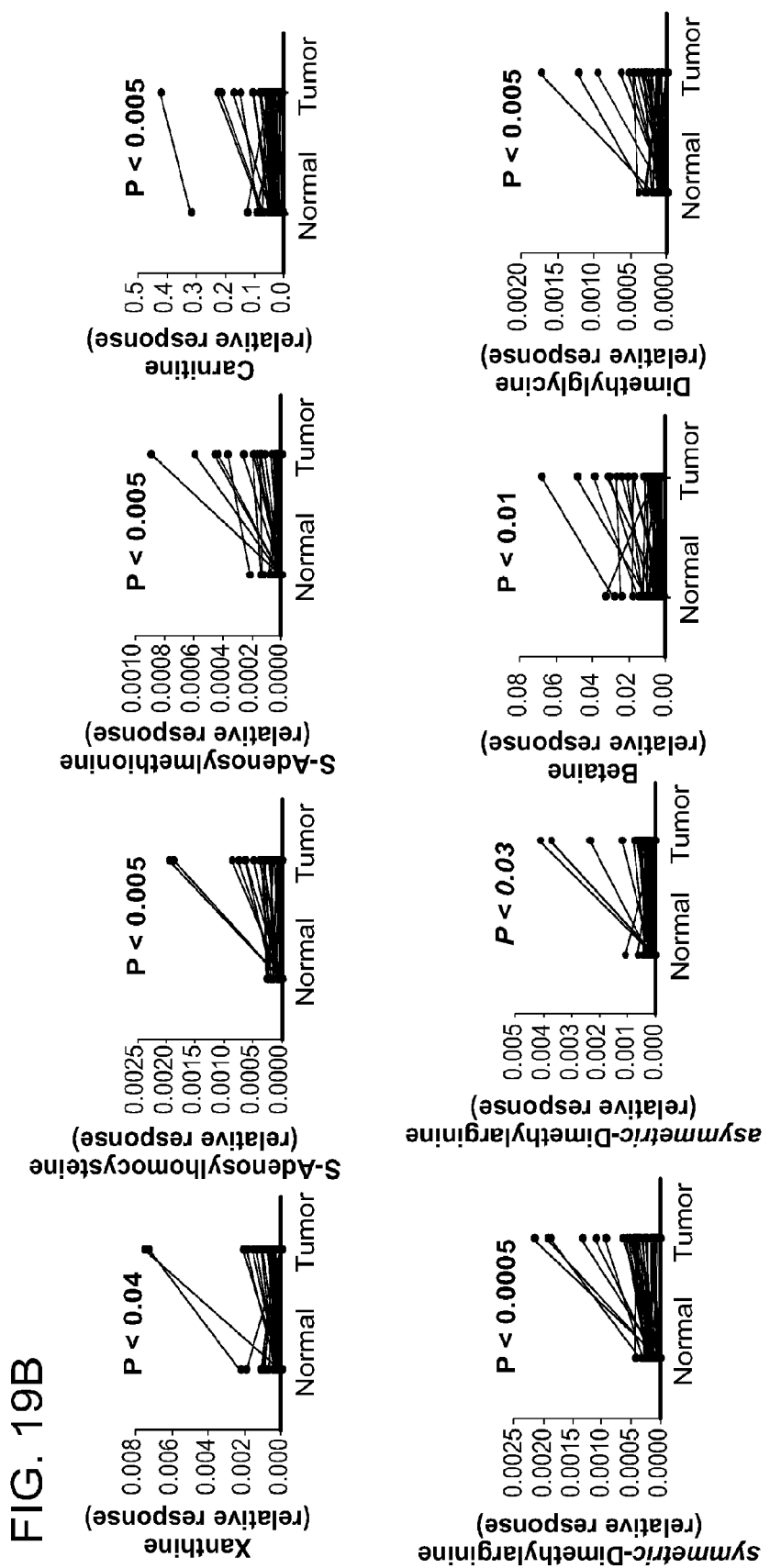

Example 7. Validation of Metabolic Reprogramming Associated with Colorectal Tumorigenesis in Human Colorectal Tumor Samples In order to examine whether the metabolic reprogramming observed in colon tumors from $Apc^{Min/+}$ mice were also associated with human colorectal tumorigenesis, the metabolic profile of human colorectal tumors and adjacent non-tumor tissues from the same patient were analyzed. To compare with the observation made in $Apc^{Min/+}$ mice where colon tumors are found only in lower two-third of the colon, human colon tumors found in rectum and sigmoidal, descending or transverse colon were analyzed together. Similar to that observed in $Apc^{Min/+}$ mice, amino acid metabolites were elevated in human colorectal tumors (FIG. 18). Metabolites connecting amino acid metabolism to urea cycle and polyamine metabolism, such as arginine and N1-acetylspermidine were also elevated. Nucleic acid metabolites such as uracil, hypoxanthine and xanthine were elevated. Similar to $Apc^{Min/+}$ mice, human tumors showed elevation of hypermethylated metabolites such as carnitine, symmetric-dimethylarginine, asymmetric-dimethylarginine, dimethylglycine and betaine along with S-adenosylmethionine and S-adenosylhomocysteine. Even in the overall cohort, which included tumors from ascending colon, aspartic acid, glutamic acid, proline, threonine, lysine, arginine, uracil, xanthine, hypoxanthine, S-adenosylhomocysteine, S-adenosylmethionine, carnitine, symmetric-dimethylarginine, asymmetric-dimethylarginine, betaine and dimethylglycine were significantly elevated (FIG. 19).

Accordingly, based on the foregoing results, it can be concluded that coordinate metabolic reprogramming of metabolic machinery involved in methylation, urea cycle and polyamine metabolism, nucleic acid metabolism and amino acid metabolism is also associated with human colorectal tumorigenesis. Similar to that observed in two independent mouse models, metabolites belonging to these pathways may act as noninvasive biomarkers of colorectal cancer in human subjects.

Example 8. Validation of Urinary Biomarkers of Colorectal Cancer in Human Samples In order to examine whether derangement of urinary metabolic profiles are indeed associated with human colorectal carcinogenesis, a preliminary set urine samples from colorectal cancer patients (N=10) and healthy controls (N=10) were analyzed.

Metabolic profiling showed significant derangement in excretion of metabolites related to amino acid metabolism (glutamine, proline and N-acetyllysine), urea cycle and polyamine metabolism (N-acetylspermidine, arginine, and ornithine), nucleic acid metabolism (deoxycytidine, cytosine, inosine, adenosine, xanthosine and hypoxanthine) and methylation (symmetric-dimethylarginine, betaine, carnitine and methionine). This included ten metabolites that were found to be elevated in the human colorectal tumor samples. In general, metabolites related to methylation and nucleic acid metabolism showed the most consistent trend. A summary of concentration ranges and statistical analysis is presented in Table 3, below.

TABLE 3

Preliminary changes in urinary metabolic profiles of colorectal cancer patients

| Metabolite | Pathway | Healthy controls (av (95% CI))[a] | Colorectal cancer patients (av (95% CI)) | P value[b] | AUCROC |
|---|---|---|---|---|---|
| SDMA | Methylation | 28.09 (21.9-34.3) | 54.85 (41.4-72.7) | <.003 | .88 |
| ADMA | Methylation | 48.5 (41.4-55.6) | 56.81 (41.4-72.7) | .24 | .66 |
| Betaine | Methylation | 1.38 (0.12-2.63) | 9.02 (3.48-14.6) | <.003 | .89 |
| Methionine | Methylation | .045 (.015-.075) | 1.02 (.52-1.5) | <.0001 | 1 |
| Carnitine | Methylation | 9.87 (4.53-15.2) | 4.25 (1.36-7.14) | .052 | .76 |
| Deoxycytidine | Nucleic acid metabolism | .006 (.004-.008) | .0104 (.008-.013) | <.01 | .84 |
| Cytosine | Nucleic acid metabolism | 1.28 (.94-1.61) | 2.35 (1.83-2.31) | .0005 | .93 |
| Inosine | Nucleic acid metabolism | .055 (.032-.078) | .29 (.071-.51) | <.0001 | .96 |
| Hypoxanthine | Nucleic acid metabolism | 14.5 (9.41-19.5) | 36.4 (17.6-55.9) | <.01 | .84 |
| Xanthosine | Nucleic acid metabolism | .91 (.48-1.33) | 4.74 (.73-8.75) | <.0001 | .96 |
| Adenosine | Nucleic acid metabolism | .00014 (.0001-.0004) | .115 (.05-.18) | <.001 | 1 |
| N1-Acetylspermidine | Urea cycle and polyamine | 21.2 (18.14-24.2) | 27.65 (20.54-34.8) | .052 | .76 |
| N8-Acetylspermidine | Urea cycle and polyamine | .86 (.61-1.1) | 1.79 (.92-2.66) | <.02 | .83 |
| Arginine | Urea cycle and polyamine | 9.08 (5.79-12.4) | 16.11 (9.95-22.3) | .03 | .8 |
| Ornithine | Urea cycle and polyamine | 15.0 (10.6-19.4) | 8.84 (6.58-11.1) | <.004 | .87 |
| Glutamine | Amino acid metabolism | 2.01 (1.13-2.89) | 70.46 (25.72-115.2) | <.0001 | 1 |
| Proline | Amino acid metabolism | 4.29 (2.97-5.6) | 1.25 (.49-2.2) | <.004 | .87 |
| Nα-acetyllysine | Amino acid metabolism | 4.32 (2.89-5.75) | 8.82 (6.03-11.6) | <.02 | .83 |

[a]All values are in the units of μmol/mmol creatinine;
[b]P values were calculated by Mann-Whitney test.

In order to further validate and extend the utility of these biomarkers in colorectal cancer screening, and diagnosis, urine samples will be collected from subjects undergoing colonoscopy to compare the metabolic signature of colorectal cancer patients with those having benign polyps as well as other non-cancerous pathologies or normal colon. In this case, the patients serve as their own control. These subjects will be monitored longitudinally to evaluate the utility of noninvasive metabolomic biomarkers in screening, prognosis and prediction of therapeutic response. A repository of urine samples from other GI malignancies will also be examines in order to examine the utility of metabolic biomarkers to other GI malignancies and/to identify signatures specific to GI sites.

Accordingly, based on the foregoing results, biomarkers reflecting metabolic reprogramming of methylation, urea cycle and polyamine metabolism, nucleic acid metabolism and amino acid metabolism can be useful in noninvasive screening and early diagnosis of colorectal cancer.

Figure 20:
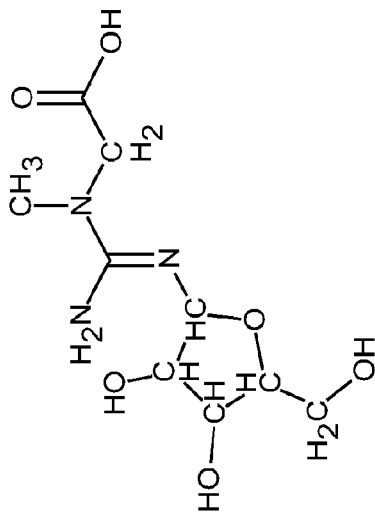
FIG. 20 shows identification of a novel metabolite (M264) as a urinary biomarker of human colorectal cancer.
Figure 20:
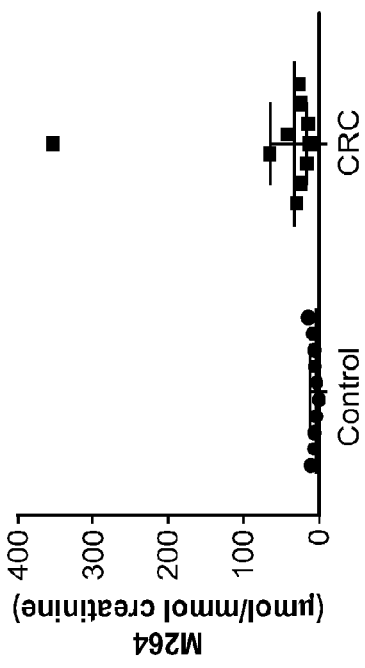
Figure 20:
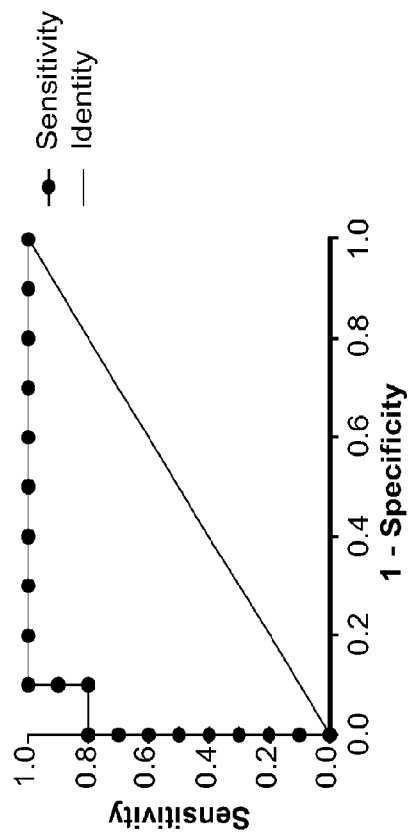
Figure 21A:
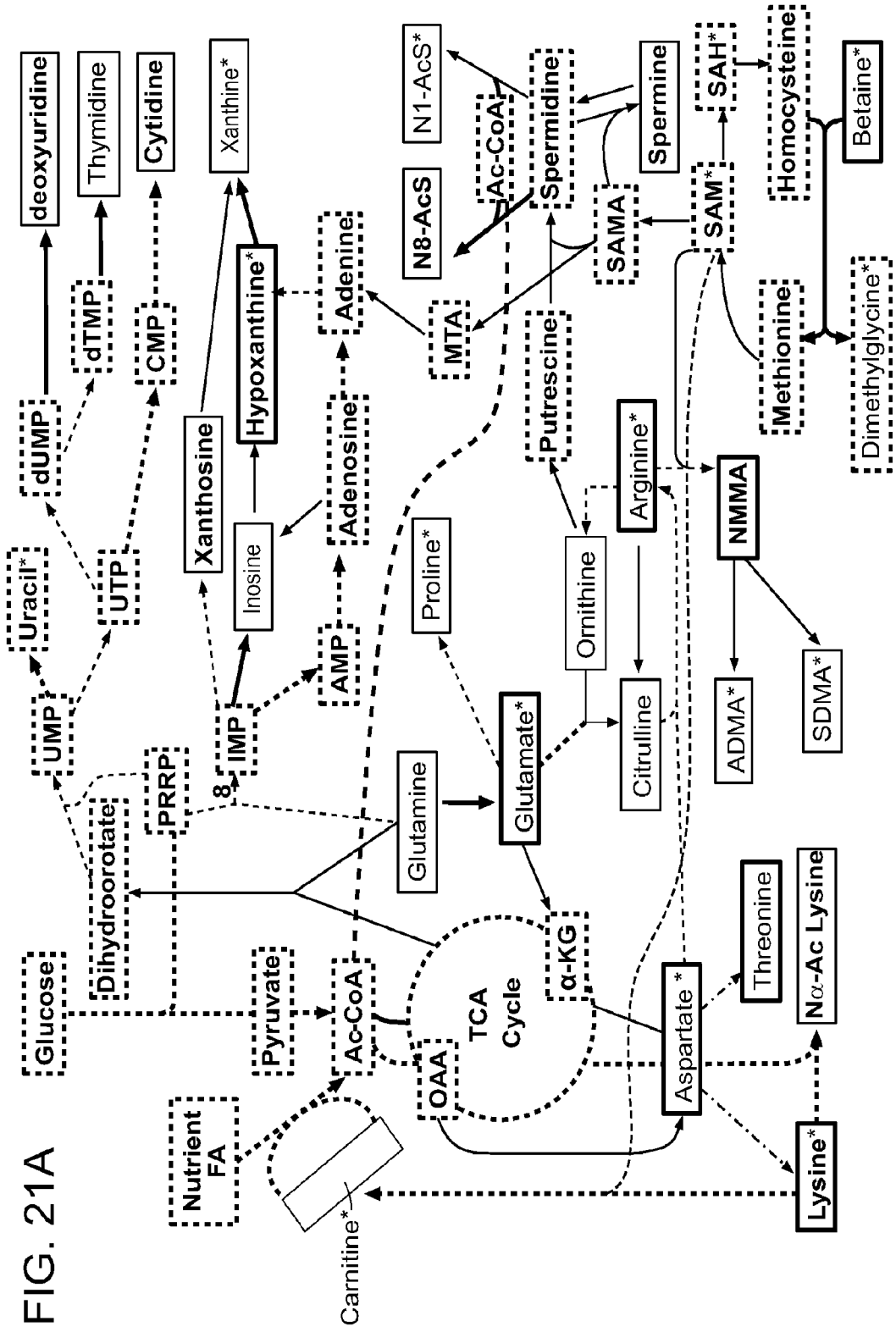
FIGS. 21A and 21B depict the coordinate deregulation and reprogramming of metabolic network in APC mutation-mediated colorectal tumorigenesis. Coordinate reprogramming of metabolic machinery in colorectal tumorigenesis.
Figure 21B:
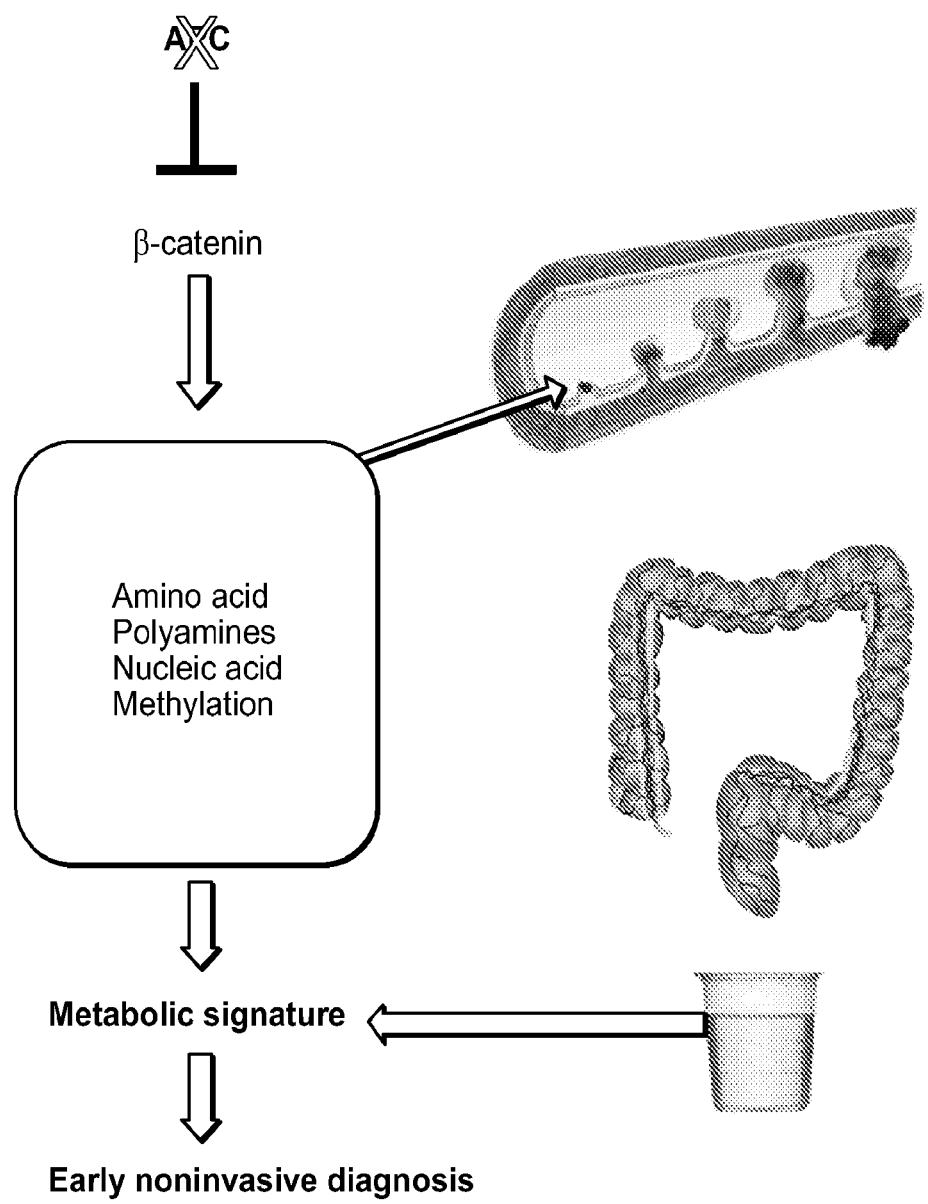

Example 9. Identification of M264 Biomarker in Urine of Colorectal Cancer Patients Another novel ion (M264) has been identified as a biomarker: 2-{2-[(2R,3R,4S,5R)-3,4-dihydroxy-5-(hydroxymethyl)-oxolan-2-yl]-1-methylcarbamimidamido}acetic acid (aka, beta-D-Ribofuranosylcreatine). FIG. 20A shows the structure of the metabolite which has a molecular formula $C_9H_{17}N_3O_6$. M264 has been found to be significantly (p<0.0001) elevated only in the urine samples of CRC patients. FIG. 20B shows the creatinine-normalized relative abundance of this metabolite in control (N=10) and patient (N=10) urine samples. ROC analysis (FIG. 20C) showed that this metabolite can identify colorectal cancer patients with high accuracy (AUCROC=0.98).

Production of this metabolite may be a result of simultaneous upregulation of pentose phosphate pathway (which also contributes to nucleic acid biosynthesis) as well as dysregulation of urea cycle and methylation machinery both of which are involved in creatine biosynthesis.

The results reported herein were obtained using the following methods and materials.

Animal Studies

Wild-type and mutant ($APC^{Min/+}$) mice were purchased from Jackson laboratories (Bar Harbor, Me.). Six age-matched wild-type and six $APC^{Min/+}$ littermates were cohabited one week after weaning in two cages containing equal numbers of wild-type and six $APC^{Min/+}$. Mice were fed with normal chow and water ad libitum and used as discovery cohorts for longitudinal metabolomic studies. Twenty four-hour urine samples were collected monthly starting from two months up to six months of age by placing mice in metabolic cages. Urine samples were also collected from an independent set of age-matched (six wild-type and six $APC^{Min/+}$) non-littermates at six months of age, which were used as a validation cohort. Serum samples were collected by retro-orbital bleeding before euthanasia. Animals were killed through $CO_2$ asphyxiation at the end of the study, intestine flushed with normal saline, longitudinally opened, tumor counted under light microscope, tissue samples harvested and all samples were stored at −80° C.

Biochemistry

Serum ALT and AST levels were measured by using VetSpec kits (Catachem Inc., Bridgeport, Conn.) following the manufacturer's instructions.

Metabolomics

Deproteinated urine and tissue samples were analyzed in Xevo G2 ESIQToFMS coupled with Acquity UPLC BEH amide column (Waters Corp. Milford, Mass.) for HILIC analysis. Reverse-phase analysis of urine samples were performed using SYNAPT HDMS ESIQToFMS coupled with Acquity UPLC BEH $C_{18}$ column. The data was deconvoluted and annotated using MassLynx software (Waters) and analyzed using SIMCA-P12+ (Umetrics, Umea, Sweden) software. The quantitation of the urinary metabolites were performed on a Xevo triple-quadruple ESIQToF platform coupled with an amide column through multiple reaction monitoring and all data were presented as normalized with respect to creatinine concentrations. Changes in relative abundance of the metabolites in tissue were calculated from internal standard-normalized area under extracted chromatograms. See Supplementary methods for detail.

Gene Expression

RNA was isolated using RNAeasy mini kit (Qiagen, Valencia, Calif.) and qPCR was performed using SYBR® GreenER™ Reagent System (Invitrogen, Carlsbad, Calif.) in a 7900 HT Fast Real-Time PCR system (Applied Biosystems, Carlsbad, Calif.). Relative change in gene expressions were calculated by the $\Delta\Delta C_t$ method with normalization to 18S rRNA. See Table 2 for primers used in qPCR.

Chemicals

HPLC grade water, acetonitrile and methanol were purchased from Fisher Scientific (Hampton, N.H.). Difluoromethylornithine, α-aminopimelic acid, creatinine, glutamine, glutamic acid, creatine, aspartic acid, lysine, citrulline, ornithine, proline, threonine, uracil, uridine, deoxyuridine, thymidine, deoxycytidine, cytidine, adenosine, guanosine, xanthine, xanthosine, hypoxanthine, inosine, uridine monophosphate, deoxyuridine monophosphate, cytidine monophosphate, adenosinetriphosphate, acetyl CoA, Nα-acetyllysine, N-acetylglutamic acid, spermine, N1-acetylspermidine, N8-acetylspermidine, arginine, Nω-monomethylarginine, sym-dimethylarginine, and asym-dimethylarginine, dimethylglycine, S-adenosylhomocysteine, S-adenosylmethionine, methionine, and betaine were purchased from Sigma-Aldrich (St. Louis, Mo.).

Global Urinary Metabolomic Analysis and Biomarker Identification.

Urine samples were deproteinated using 50% or 70% acetonitrile containing 5 μM chloropropamide or α-aminopimelic acid as internal standards for reverse-phase (RP) or hydrophilic interaction liquid chromatography (HILIC), respectively. Supernatants were transferred into 96-well sample plates. All pipetting and dilution were performed using a MICROLAB STAR$^{LET}$ automated liquid handler (Hamilton Robotics, Reno, Nev.). For HILIC analysis, 5 μL aliquot of samples were injected in a randomized fashion into a 2.1×50 mm Acquity UPLC BEH amide column (1.7 μM) connected to a XEVO G2 ESIQTOF mass spectrometer (Waters Corporation, Milford, Mass.). Chromatographic separation was achieved by using a mixture of (A) 10 mM ammonium acetate in 90% acetonitrile (pH=8.9) and (B) 10 mM ammonium acetate in 10% acetonitrile (pH1=8.9) as mobile phase. The gradient elution was performed over 10 min using: 1-60% B in 4 min (0.4 ml/min), 60-80% B at 8 min (0.4 ml/min), holding at 80% B up to 8.5 min (0.3 ml/min), bringing back to 1% B at 8.8 min and holding at 1% until end (0.3 ml/min). Column temperature was maintained at 40° C. Column was re-equilibrated with 99% A at the end of each run prior to injection of next sample. For reverse-phase analysis, 5 μL aliquot of samples were injected into a 2.1×50 mm Acquity UPLC BEH Cis column (1.7 μM)

connected to a SYNAPT HDMS ESIQTOF mass spectrometer (Waters Corporation). Chromatographic separation was achieved by using a mixture of (A) water containing 1% formic acid and (B) acetonitrile containing 1% formic acid as mobile phase. The gradient elution was performed over 6 min at a flow rate of 0.3 mL using: 1-99% B in 4 min, holding at 99% B up to 5.0 min, bringing back to 1% at 5.5 min and holding at 1% until end. Column temperature was maintained at 40° C. Column was re-equilibrated with 98% A at the end of each run prior to injection of next sample. Mass spectrometric analysis was performed in both positive and negative ionization modes. Sulfadimethoxine was used as the lock mass (m/z $311.0814^{+)}$ for accurate mass calibration in real time. MassLynx software (Waters Corporation) was used to acquire mass chromatograms and mass spectral data in centroid format.

Chromatograms were manually inspected for chromatogram quality and retention time reproducibility across the run. MarkerLynx software (Waters Corporation) was used to deconvolute chromatograms, bin the data according to mass-retention time pairs and integrate the area under the peak. The intensity of each ion was normalized with respect to the either total ion count (TIC) or creatinine (m/z 114.067, RT=0.3 min or 0.8 min in RP or HILIC mode) count to generate a data matrix consisting of m/z value, retention time, and the normalized peak area. The multivariate data matrix was analyzed by SIMCA-P+12 software (Umetrics, Kinnelon, N.J.). Data quality inspection as well as distribution and unsupervised segregation of wild-type and mutants on global metabolomic space were checked by principal components analysis (PCA) of the Pareto-scaled data. The supervised orthogonal projection to latent structures (OPLS) model was used identify ions contributing to discrimination (indicated by their distance from origin along Y-axes) of metabolic traits. Consistency of longitudinal trend of ions in contributing to difference of wild-type and mutant metabolome was examined to select potential biomarker candidates. Candidate metabolites for these ions were identified on the basis of accurate mass measurement using metabolomic databases such as METLIN or HMDB and MS/MS fragmentation pattern. Finally, identities of biomarker were confirmed by comparison of retention time and fragmentation pattern with authentic standards.

Targeted Urinary Metabolite Quantitation.

Metabolites in the deproteinated urine samples were quantified in multiple reactions monitoring mode on a XEVO triple quadruple mass spectrometer (Water Corporation). α-Aminopimelic acid (5 μM) was used as internal standard. The following metabolites were quantified by monitoring characteristic fragmentation reactions (in bracket); α-aminopimelic acid (176→112, ESI+), creatinine (114→86, ESI+), aspartic acid (132→88, ESI−), glutamine (147→84, ESI+), glutamic acid (148→84, ESI+), creatine (132→90, ESI+), lysine (147→130, ESI+), citrulline (176→159, ESI+), ornithine (133→70, ESI+), arginine (175→60, ESI+), Nω-monomethylarginine (189→84, ESI+), sym-dimethylarginine (203→172, ESI+), and asym-dimethylarginine (203→46, ESI+), proline (116→70, ESI+), threonine (120→74, ESI+), uridine (245→113, ESI+), deoxyuridine (229→117, ESI+), thymidine (241→151, ESI−), cytidine (244→112, ESI+), xanthine (151→108, ESI−), xanthosine, (285→153, ESI+), hypoxanthine (137→119, ESI+), inosine (269→153, ESI+), Nα-acetyllysine (189→129, ESI+), N1-acetylspermidine (188→72, ESI+), N8-acetylspermidine (188→114, ESI+), betaine (118→59, ESI+), deoxycytidine (228→111, ESI+), adenosine (268→136, ESI+), methionine (150→56, ESI+), guanosine (2844→122, ESI+) and M264 (264→132, ESI+). Spermine was measured by single ion monitoring (203, ESI+) and relative abundance was measured by area under the peak. Chromatographic separation was achieved on a 2.1×50 mm Acquity UPLC BEH amide column using the mobile phase as mentioned above. The gradient elution was performed over 10 min at a flow rate of 0.5 ml/min using: 1-40% B in 6 min, 40-60% B at 8 min, 60-80% at 8.2 min, bringing back to 1% B at 9 min and holding at 1% until end. All data were processed using TargetLynx software (Waters Corporation). Internal standard-normalized area under the peak (response) from serially diluted authentic standard solution was used to build calibration curve for each metabolite. The concentration of metabolite was determined from the calibration curve and divided by creatinine concentration to determine creatinine-normalized excretion of the metabolite in 24-hour urine.

Mouse Tissue Metabolite Measurements.

Tumor (n=6) and normal colon mucosal tissue (n=5) samples were weighed and homogenized using a Precellys 24 homogenizer (Bertin technologies, France) and extracted using modified Bligh-Dyer method to separate the polar and non-polar metabolites. α-Aminopimelic acid (10 μM) was added to each sample before extraction to normalize differences in metabolite extraction efficiency. Aqueous layer was vacuum-dried and reconstituted in acetonitrile/water/methanol (65:30:5) mixture containing 5 μM difluoromethylornithine. Samples were analyzed on a XEVO G2 ESI-QTOF instrument connected to a 2.1×50 mm Acquity UPLC BEH amide column (1.7 μM) with mobile phase as mentioned earlier. The gradient elution was performed over 10 min using: 1-40% B in 6 min (0.4 ml/min), 40-80% B at 8 min (0.4 ml/min), holding at 80% B up to 8.5 min (0.3 ml/min), bringing back to 1% B at 8.8 min and holding at 1% until the end of the run (0.3 ml/min). All samples were run in a randomized fashion along with authentic standards. Raw chromatograms were extracted with masses for target compounds and peaks at characteristic retention times (as that of the authentic standard) were integrated to get area under the peak using TargetLynx software. The area under the peak for each metabolite was normalized step-by-step for initial tissue weight, extraction efficiency (α-aminopimelic acid) and instrument response (difluoromethylornithine). The fold change in abundance of metabolites in tumor tissue samples were calculated by dividing the normalized response for the metabolite from tumor samples by the average normalized response from normal mucosal tissue samples. Colon scrapes from tamoxifen-treated Cre+ (n=3) and Cre− (n=3) mice were extracted as mentioned above. Metabolite composition was quantitated using MRM and normalized as mentioned above. In addition to aforementioned MRMs, the following MRMs were also monitored for respective metabolites; adenosine (268→136, ESI+), UMP (325→97, ESI−), dUMP (309→81, ESI+), CMP (324→112, ESI+), ATP (508→136, ESI+), N-acetylglutamic acid (190→84, ESI+), acetyl CoA (810→303, ESI+), uracil (111→42, ESI−−), dimethylglycine (104→58, ESI+), S-adenosylhomocysteine (385→134, ESI+), and S-adenosylmethionine (3994→250, ESI+). The fold change in abundance of metabolites in Cre+ colon epithelium were calculated by dividing the normalized response for the metabolite from tumor samples by the average normalized response from Cre− colon epithelium.

Human Tissue Metabolite Measurements.

Matched tumor (N=39) and adjacent normal tissues were extracted following the same protocol as that described above for mouse tissues. Targeted measurement of metabolite abundances in the reconstituted aqueous extract were performed by MRM reaction monitoring coupled with hydrophilic interaction liquid chromatography as mentioned above for analysis of urine samples. The area under the peak for each metabolite was normalized step-by-step for initial tissue weight, extraction efficiency (α-aminopimelic acid) and instrument response (difluoromethylornithine) and presented as normalized response.

Statistics

Statistical significance of changes in metabolite abundance and gene expression were calculated by two-tailed Mann-Whitney test with 95% confidence interval using Graphpad Prism (San Diego, Calif.) unless mentioned otherwise. The creatinine-normalized urinary excretion of metabolites was used to test the predictive power of individual metabolites or metabolite panels by ROC analysis using STATA software (StataCorp, College Station, Tex.). The statistical significance of the change in metabolite abundances in matched human samples were calculated using two-tailed paired 't'-test with 95% confidence interval. P value <0.05 was considered statistically significant.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and CAS numbers mentioned in this specification are herein incorporated by reference to the same extent as if each independent patent and publication was specifically and individually indicated to be incorporated by reference.

---

What is claimed is:

1. A method for identifying a subject as having colorectal cancer, the method comprising:

identifying a change in the level of a combination of two or more biomarkers in a biological fluid or tissue sample derived from the subject relative to the level present in a reference, wherein a first biomarker is selected from a first group, and at least one additional biomarker is selected from a different group, wherein the groups are selected from among the following:

(a) biomarkers related to methylation comprising at least one of asymmetric-dimethylarginine, symmetric-dimethylarginine, carnitine, methionine, dimethylglycine, or betaine;

(b) biomarkers related to nucleic acid metabolism comprising at least one of xanthosine, inosine, deoxyuridine, thymidine, deoxycytidine, cytosine, hypoxanthine, xanthine, uracil, guanosine, or adenosine;

(c) biomarkers related to urea cycle and polyamine metabolism comprising at least one of N1-acetyl spermidine, N8-acetyl spermidine, spermine, arginine ornithine, or citrulline;

(d) biomarkers related to amino acid metabolism comprising at least one of proline, glutamine, glutamic acid, threonine, or Nα-acetyllysine; and (e) M264 (β-D-Ribofuranosylcreatine), wherein the subject is identified as having colorectal cancer when:

(i) the levels of two or more biomarkers in the biological fluid are increased, or (ii) the change in the levels of the biomarkers in a tissue sample are: (A) increased for asymmetric-dimethylarginine, symmetric-dimethylarginine, carnitine, methionine, dimethylglycine, betaine, deoxyuridine, thymidine, deoxycytidine, cytosine, hypoxanthine, xanthosine, uracil, guanosine, adenosine, N1-acetyl spermidine, N8-acetyl spermidine, spermine, arginine ornithine, citrulline, proline, glutamine, glutamic acid, threonine, Nα-acetyllysine, and M264; and (B) decreased for xanthine and inosine;

normalizing the level of at least one of the biomarkers to the level of creatine in the sample, absolute concentration, 24-hr excretion, or with respect to specific gravity; and treating the colorectal cancer with surgery, radiation therapy, external beam radiation therapy, brachytherapy, chemotherapy, or a combination thereof.

2. The method of claim 1, wherein the groups are selected from the following:
biomarkers related to methylation comprising at least one of asymmetric-dimethylarginine or symmetric-dimethylarginine;
biomarkers related to nucleic acid metabolism comprising at least one of xanthosine, inosine, deoxyuridine, or thymidine;
biomarkers related to polyamine metabolism comprising at least one of N1-acetyl spermidine, N8-acetyl spermidine, or spermine; and
biomarkers related to amino acid metabolism comprising at least one of proline, glutamine, or Nα-acetyllysine.

3. The method of claim 1, wherein the tissue sample is a biopsy.

4. The method of claim 1, wherein the biological fluid is selected from the group consisting of urine, blood, blood serum, plasma, bile, fecal aspirate, intestinal aspirate, cerebrospinal fluid and saliva.

5. The method of claim 1, further comprising measuring the level of carnitine in the biological sample.

6. The method of claim 5, wherein a decrease in the level of carnitine in the biological fluid identifies a subject as having colorectal cancer.

7. The method of claim 5, wherein an increase in the level of carnitine in the biological fluid identifies a subject as having an increased chance of survival.

8. The method of claim 5, wherein an increase in the level of carnitine in the tissue sample identifies a subject as having colorectal cancer.

9. The method of claim 5, wherein a decrease in the level of carnitine in the tissue sample identifies a subject as having an increased chance of survival.

10. The method of claim 1, wherein the colorectal cancer comprises a mutation in APC or a Wnt signaling pathway protein.

11. The method of claim 1, further comprising detecting a mutation in APC or a Wnt signaling pathway protein.

12. The method of claim 1, wherein the level of the biomarker is increased 1.5, 2, 2.5, 3, 3.5, 4, 5, 6, 7, 8, 9, 10, 11, 12, 13, 14, 15-fold or more relative to the reference.

13. The method of claim 1, wherein the reference is a control or a corresponding biological sample derived from a healthy subject.

14. The method of claim 1, wherein the biomarker level is detected by chromatography, mass spectrometry, spectroscopy, or immunoassay.

15. The method of claim 1, wherein the first biomarker or the additional biomarker is M264 (β-D-Ribofuranosylcreatine).

16. The method of claim 1, further comprising characterizing the colorectal cancer, wherein:
an increased level of the biomarker related to methylation relative to the reference identifies a more aggressive colorectal cancer; or
a decreases level of the biomarker related to methylation relative to the reference identifies a less aggressive colorectal cancer.

17. The method of claim 16, wherein the treatment corresponds to the more aggressive colorectal cancer.

18. The method of claim 16, wherein the treatment corresponds to the less aggressive colorectal cancer.

19. A method for identifying a subject as having colorectal cancer, the method comprising:
identifying a change in the level of a combination of two or more biomarkers in a biological fluid or tissue sample derived from the subject relative to the level present in a reference, wherein a first biomarker is M264 (β-D-Ribofuranosylcreatine), and at least one additional biomarker is selected from a different group, wherein the groups are selected from among the following:
(a) biomarkers related to methylation comprising at least one of asymmetric-dimethylarginine, symmetric-dimethylarginine, carnitine, methionine, dimethylglycine, or betaine;
(b) biomarkers related to nucleic acid metabolism comprising at least one of xanthosine, inosine, deoxyuridine, thymidine, deoxycytidine, cytosine, hypoxanthine, xanthine, uracil, guanosine, or adenosine;
(c) biomarkers related to urea cycle and polyamine metabolism comprising at least one of N1-acetyl spermidine, N8-acetyl spermidine, spermine, arginine ornithine, or citrulline; and
(d) biomarkers related to amino acid metabolism comprising at least one of proline, glutamine, glutamic acid, threonine, or Nα-acetyllysine;
wherein the subject is identified as having colorectal cancer when:
(i) the levels of two or more biomarkers in the biological fluid are increased, or
(ii) the change in the levels of the biomarkers in a tissue sample are: (A) increased for asymmetric-dimethylarginine, symmetric-dimethylarginine, carnitine, methionine, dimethylglycine, betaine, deoxyuridine, thymidine, deoxycytidine, cytosine, hypoxanthine, xanthosine, uracil, guanosine, adenosine, N1-acetyl spermidine, N8-acetyl spermidine, spermine, arginine ornithine, citrulline, proline, glutamine, glutamic acid, threonine, Nα-acetyllysine, and M264; and (B) decreased for xanthine and inosine; and
treating the colorectal cancer with surgery, radiation therapy, external beam radiation therapy, brachytherapy, chemotherapy, or a combination thereof.

* * * * *

SEQUENCE LISTING

<160> NUMBER OF SEQ ID NOS: 16

<210> SEQ ID NO 1
<211> LENGTH: 2843
<212> TYPE: PRT
<213> ORGANISM: Homo sapiens

<400> SEQUENCE: 1

```
Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
                20                  25                  30

His Leu Thr Lys Leu Glu Thr Glu Ala Ser Asn Met Lys Glu Val Leu
            35                  40                  45

Lys Gln Leu Gln Gly Ser Ile Glu Asp Glu Ala Met Ala Ser Ser Gly
        50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
                100                 105                 110

Val Pro Met Gly Ser Phe Pro Arg Arg Gly Phe Val Asn Gly Ser Arg
            115                 120                 125

Glu Ser Thr Gly Tyr Leu Glu Glu Leu Glu Lys Glu Arg Ser Leu Leu
        130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
```

-continued

```
            225                 230                 235                 240

Glu Ala Glu Arg Ser Ser Gln Asn Lys His Glu Thr Gly Ser His Asp
                        245                 250                 255

Ala Glu Arg Gln Asn Glu Gly Gln Gly Val Gly Glu Ile Asn Met Ala
                        260                 265                 270

Thr Ser Gly Asn Gly Gln Gly Ser Thr Thr Arg Met Asp His Glu Thr
                        275                 280                 285

Ala Ser Val Leu Ser Ser Ser Thr His Ser Ala Pro Arg Arg Leu
            290                 295                 300

Thr Ser His Leu Gly Thr Lys Val Glu Met Val Tyr Ser Leu Leu Ser
        305                 310                 315                 320

Met Leu Gly Thr His Asp Lys Asp Met Ser Arg Thr Leu Leu Ala
                        325                 330                 335

Met Ser Ser Ser Gln Asp Ser Cys Ile Ser Met Arg Gln Ser Gly Cys
                        340                 345                 350

Leu Pro Leu Leu Ile Gln Leu Leu His Gly Asn Asp Lys Asp Ser Val
                        355                 360                 365

Leu Leu Gly Asn Ser Arg Gly Ser Lys Glu Ala Arg Ala Arg Ala Ser
            370                 375                 380

Ala Ala Leu His Asn Ile Ile His Ser Gln Pro Asp Asp Lys Arg Gly
        385                 390                 395                 400

Arg Arg Glu Ile Arg Val Leu His Leu Leu Glu Gln Ile Arg Ala Tyr
                        405                 410                 415

Cys Glu Thr Cys Trp Glu Trp Gln Glu Ala His Glu Pro Gly Met Asp
                        420                 425                 430

Gln Asp Lys Asn Pro Met Pro Ala Pro Val Glu His Gln Ile Cys Pro
                        435                 440                 445

Ala Val Cys Val Leu Met Lys Leu Ser Phe Asp Glu Glu His Arg His
            450                 455                 460

Ala Met Asn Glu Leu Gly Gly Leu Gln Ala Ile Ala Glu Leu Leu Gln
        465                 470                 475                 480

Val Asp Cys Glu Met Tyr Gly Leu Thr Asn Asp His Tyr Ser Ile Thr
                        485                 490                 495

Leu Arg Arg Tyr Ala Gly Met Ala Leu Thr Asn Leu Thr Phe Gly Asp
                        500                 505                 510

Val Ala Asn Lys Ala Thr Leu Cys Ser Met Lys Gly Cys Met Arg Ala
                        515                 520                 525

Leu Val Ala Gln Leu Lys Ser Glu Ser Glu Asp Leu Gln Gln Val Ile
            530                 535                 540

Ala Ser Val Leu Arg Asn Leu Ser Trp Arg Ala Asp Val Asn Ser Lys
        545                 550                 555                 560

Lys Thr Leu Arg Glu Val Gly Ser Val Lys Ala Leu Met Glu Cys Ala
                        565                 570                 575

Leu Glu Val Lys Lys Glu Ser Thr Leu Lys Ser Val Leu Ser Ala Leu
                        580                 585                 590

Trp Asn Leu Ser Ala His Cys Thr Glu Asn Lys Ala Asp Ile Cys Ala
                        595                 600                 605

Val Asp Gly Ala Leu Ala Phe Leu Val Gly Thr Leu Thr Tyr Arg Ser
            610                 615                 620

Gln Thr Asn Thr Leu Ala Ile Ile Glu Ser Gly Gly Gly Ile Leu Arg
        625                 630                 635                 640

Asn Val Ser Ser Leu Ile Ala Thr Asn Glu Asp His Arg Gln Ile Leu
                        645                 650                 655
```

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asn Arg Ser Asp Asn Phe Asn Thr
                805                 810                 815

Gly Asn Met Thr Val Leu Ser Pro Tyr Leu Asn Thr Thr Val Leu Pro
                820                 825                 830

Ser Ser Ser Ser Ser Arg Gly Ser Leu Asp Ser Ser Arg Ser Glu Lys
            835                 840                 845

Asp Arg Ser Leu Glu Arg Glu Arg Gly Ile Gly Leu Gly Asn Tyr His
        850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Glu Ser
            980                 985                 990

Lys Phe Cys Ser Tyr Gly Gln Tyr Pro Ala Asp Leu Ala His Lys Ile
            995                 1000                1005

His Ser Ala Asn His Met Asp Asp Asn Asp Gly Glu Leu Asp Thr
        1010                1015                1020

Pro Ile Asn Tyr Ser Leu Lys Tyr Ser Asp Glu Gln Leu Asn Ser
        1025                1030                1035

Gly Arg Gln Ser Pro Ser Gln Asn Glu Arg Trp Ala Arg Pro Lys
        1040                1045                1050

His Ile Ile Glu Asp Glu Ile Lys Gln Ser Glu Gln Arg Gln Ser
        1055                1060                1065

```
Arg Asn Gln Ser Thr Thr Tyr Pro Val Tyr Thr Glu Ser Thr Asp
1070             1075             1080

Asp Lys His Leu Lys Phe Gln Pro His Phe Gly Gln Gln Glu Cys
1085             1090             1095

Val Ser Pro Tyr Arg Ser Arg Gly Ala Asn Gly Ser Glu Thr Asn
1100             1105             1110

Arg Val Gly Ser Asn His Gly Ile Asn Gln Asn Val Ser Gln Ser
1115             1120             1125

Leu Cys Gln Glu Asp Asp Tyr Glu Asp Asp Lys Pro Thr Asn Tyr
1130             1135             1140

Ser Glu Arg Tyr Ser Glu Glu Glu Gln His Glu Glu Glu Arg
1145             1150             1155

Pro Thr Asn Tyr Ser Ile Lys Tyr Asn Glu Glu Lys Arg His Val
1160             1165             1170

Asp Gln Pro Ile Asp Tyr Ser Leu Lys Tyr Ala Thr Asp Ile Pro
1175             1180             1185

Ser Ser Gln Lys Gln Ser Phe Ser Phe Ser Lys Ser Ser Ser Gly
1190             1195             1200

Gln Ser Ser Lys Thr Glu His Met Ser Ser Ser Glu Asn Thr
1205             1210             1215

Ser Thr Pro Ser Ser Asn Ala Lys Arg Gln Asn Gln Leu His Pro
1220             1225             1230

Ser Ser Ala Gln Ser Arg Ser Gly Gln Pro Gln Lys Ala Ala Thr
1235             1240             1245

Cys Lys Val Ser Ser Ile Asn Gln Glu Thr Ile Gln Thr Tyr Cys
1250             1255             1260

Val Glu Asp Thr Pro Ile Cys Phe Ser Arg Cys Ser Ser Leu Ser
1265             1270             1275

Ser Leu Ser Ser Ala Glu Asp Glu Ile Gly Cys Asn Gln Thr Thr
1280             1285             1290

Gln Glu Ala Asp Ser Ala Asn Thr Leu Gln Ile Ala Glu Ile Lys
1295             1300             1305

Glu Lys Ile Gly Thr Arg Ser Ala Glu Asp Pro Val Ser Glu Val
1310             1315             1320

Pro Ala Val Ser Gln His Pro Arg Thr Lys Ser Ser Arg Leu Gln
1325             1330             1335

Gly Ser Ser Leu Ser Ser Glu Ser Ala Arg His Lys Ala Val Glu
1340             1345             1350

Phe Ser Ser Gly Ala Lys Ser Pro Ser Lys Ser Gly Ala Gln Thr
1355             1360             1365

Pro Lys Ser Pro Pro Glu His Tyr Val Gln Glu Thr Pro Leu Met
1370             1375             1380

Phe Ser Arg Cys Thr Ser Val Ser Ser Leu Asp Ser Phe Glu Ser
1385             1390             1395

Arg Ser Ile Ala Ser Ser Val Gln Ser Glu Pro Cys Ser Gly Met
1400             1405             1410

Val Ser Gly Ile Ile Ser Pro Ser Asp Leu Pro Asp Ser Pro Gly
1415             1420             1425

Gln Thr Met Pro Pro Ser Arg Ser Lys Thr Pro Pro Pro Pro
1430             1435             1440

Gln Thr Ala Gln Thr Lys Arg Glu Val Pro Lys Asn Lys Ala Pro
1445             1450             1455

Thr Ala Glu Lys Arg Glu Ser Gly Pro Lys Gln Ala Ala Val Asn
```

-continued

```
            1460                1465                1470

Ala Ala Val Gln Arg Val Gln Val Leu Pro Asp Ala Asp Thr Leu
    1475                1480                1485

Leu His Phe Ala Thr Glu Ser Thr Pro Asp Gly Phe Ser Cys Ser
    1490                1495                1500

Ser Ser Leu Ser Ala Leu Ser Leu Asp Glu Pro Phe Ile Gln Lys
    1505                1510                1515

Asp Val Glu Leu Arg Ile Met Pro Pro Val Gln Glu Asn Asp Asn
    1520                1525                1530

Gly Asn Glu Thr Glu Ser Glu Gln Pro Lys Glu Ser Asn Glu Asn
    1535                1540                1545

Gln Glu Lys Glu Ala Glu Lys Thr Ile Asp Ser Glu Lys Asp Leu
    1550                1555                1560

Leu Asp Asp Ser Asp Asp Asp Ile Glu Ile Leu Glu Glu Cys
    1565                1570                1575

Ile Ile Ser Ala Met Pro Thr Lys Ser Ser Arg Lys Ala Lys Lys
    1580                1585                1590

Pro Ala Gln Thr Ala Ser Lys Leu Pro Pro Val Ala Arg Lys
    1595                1600                1605

Pro Ser Gln Leu Pro Val Tyr Lys Leu Leu Pro Ser Gln Asn Arg
    1610                1615                1620

Leu Gln Pro Gln Lys His Val Ser Phe Thr Pro Gly Asp Asp Met
    1625                1630                1635

Pro Arg Val Tyr Cys Val Glu Gly Thr Pro Ile Asn Phe Ser Thr
    1640                1645                1650

Ala Thr Ser Leu Ser Asp Leu Thr Ile Glu Ser Pro Pro Asn Glu
    1655                1660                1665

Leu Ala Ala Gly Glu Gly Val Arg Gly Gly Ala Gln Ser Gly Glu
    1670                1675                1680

Phe Glu Lys Arg Asp Thr Ile Pro Thr Glu Gly Arg Ser Thr Asp
    1685                1690                1695

Glu Ala Gln Gly Gly Lys Thr Ser Ser Val Thr Ile Pro Glu Leu
    1700                1705                1710

Asp Asp Asn Lys Ala Glu Glu Gly Asp Ile Leu Ala Glu Cys Ile
    1715                1720                1725

Asn Ser Ala Met Pro Lys Gly Lys Ser His Lys Pro Phe Arg Val
    1730                1735                1740

Lys Lys Ile Met Asp Gln Val Gln Gln Ala Ser Ala Ser Ser Ser
    1745                1750                1755

Ala Pro Asn Lys Asn Gln Leu Asp Gly Lys Lys Lys Lys Pro Thr
    1760                1765                1770

Ser Pro Val Lys Pro Ile Pro Gln Asn Thr Glu Tyr Arg Thr Arg
    1775                1780                1785

Val Arg Lys Asn Ala Asp Ser Lys Asn Asn Leu Asn Ala Glu Arg
    1790                1795                1800

Val Phe Ser Asp Asn Lys Asp Ser Lys Lys Gln Asn Leu Lys Asn
    1805                1810                1815

Asn Ser Lys Val Phe Asn Asp Lys Leu Pro Asn Asn Glu Asp Arg
    1820                1825                1830

Val Arg Gly Ser Phe Ala Phe Asp Ser Pro His His Tyr Thr Pro
    1835                1840                1845

Ile Glu Gly Thr Pro Tyr Cys Phe Ser Arg Asn Asp Ser Leu Ser
    1850                1855                1860
```

```
Ser Leu Asp Phe Asp Asp Asp Val Asp Leu Ser Arg Glu Lys
1865                1870                1875

Ala Glu Leu Arg Lys Ala Lys Glu Asn Lys Glu Ser Glu Ala Lys
1880                1885                1890

Val Thr Ser His Thr Glu Leu Thr Ser Asn Gln Gln Ser Ala Asn
    1895                1900                1905

Lys Thr Gln Ala Ile Ala Lys Gln Pro Ile Asn Arg Gly Gln Pro
1910                1915                1920

Lys Pro Ile Leu Gln Lys Gln Ser Thr Phe Pro Gln Ser Ser Lys
1925                1930                1935

Asp Ile Pro Asp Arg Gly Ala Ala Thr Asp Glu Lys Leu Gln Asn
1940                1945                1950

Phe Ala Ile Glu Asn Thr Pro Val Cys Phe Ser His Asn Ser Ser
1955                1960                1965

Leu Ser Ser Leu Ser Asp Ile Asp Gln Glu Asn Asn Asn Lys Glu
    1970                1975                1980

Asn Glu Pro Ile Lys Glu Thr Glu Pro Pro Asp Ser Gln Gly Glu
    1985                1990                1995

Pro Ser Lys Pro Gln Ala Ser Gly Tyr Ala Pro Lys Ser Phe His
    2000                2005                2010

Val Glu Asp Thr Pro Val Cys Phe Ser Arg Asn Ser Ser Leu Ser
    2015                2020                2025

Ser Leu Ser Ile Asp Ser Glu Asp Asp Leu Leu Gln Glu Cys Ile
    2030                2035                2040

Ser Ser Ala Met Pro Lys Lys Lys Lys Pro Ser Arg Leu Lys Gly
    2045                2050                2055

Asp Asn Glu Lys His Ser Pro Arg Asn Met Gly Gly Ile Leu Gly
    2060                2065                2070

Glu Asp Leu Thr Leu Asp Leu Lys Asp Ile Gln Arg Pro Asp Ser
    2075                2080                2085

Glu His Gly Leu Ser Pro Asp Ser Glu Asn Phe Asp Trp Lys Ala
    2090                2095                2100

Ile Gln Glu Gly Ala Asn Ser Ile Val Ser Ser Leu His Gln Ala
    2105                2110                2115

Ala Ala Ala Ala Cys Leu Ser Arg Gln Ala Ser Ser Asp Ser Asp
    2120                2125                2130

Ser Ile Leu Ser Leu Lys Ser Gly Ile Ser Leu Gly Ser Pro Phe
    2135                2140                2145

His Leu Thr Pro Asp Gln Glu Glu Lys Pro Phe Thr Ser Asn Lys
    2150                2155                2160

Gly Pro Arg Ile Leu Lys Pro Gly Glu Lys Ser Thr Leu Glu Thr
    2165                2170                2175

Lys Lys Ile Glu Ser Glu Ser Lys Gly Ile Lys Gly Gly Lys Lys
    2180                2185                2190

Val Tyr Lys Ser Leu Ile Thr Gly Lys Val Arg Ser Asn Ser Glu
    2195                2200                2205

Ile Ser Gly Gln Met Lys Gln Pro Leu Gln Ala Asn Met Pro Ser
    2210                2215                2220

Ile Ser Arg Gly Arg Thr Met Ile His Ile Pro Gly Val Arg Asn
    2225                2230                2235

Ser Ser Ser Ser Thr Ser Pro Val Ser Lys Lys Gly Pro Pro Leu
    2240                2245                2250
```

```
Lys Thr Pro Ala Ser Lys Ser Pro Ser Glu Gly Gln Thr Ala Thr
    2255                2260                2265

Thr Ser Pro Arg Gly Ala Lys Pro Ser Val Lys Ser Glu Leu Ser
    2270                2275                2280

Pro Val Ala Arg Gln Thr Ser Gln Ile Gly Gly Ser Ser Lys Ala
    2285                2290                2295

Pro Ser Arg Ser Gly Ser Arg Asp Ser Thr Pro Ser Arg Pro Ala
    2300                2305                2310

Gln Gln Pro Leu Ser Arg Pro Ile Gln Ser Pro Gly Arg Asn Ser
    2315                2320                2325

Ile Ser Pro Gly Arg Asn Gly Ile Ser Pro Pro Asn Lys Leu Ser
    2330                2335                2340

Gln Leu Pro Arg Thr Ser Ser Pro Ser Thr Ala Ser Thr Lys Ser
    2345                2350                2355

Ser Gly Ser Gly Lys Met Ser Tyr Thr Ser Pro Gly Arg Gln Met
    2360                2365                2370

Ser Gln Gln Asn Leu Thr Lys Gln Thr Gly Leu Ser Lys Asn Ala
    2375                2380                2385

Ser Ser Ile Pro Arg Ser Glu Ser Ala Ser Lys Gly Leu Asn Gln
    2390                2395                2400

Met Asn Asn Gly Asn Gly Ala Asn Lys Lys Val Glu Leu Ser Arg
    2405                2410                2415

Met Ser Ser Thr Lys Ser Ser Gly Ser Glu Ser Asp Arg Ser Glu
    2420                2425                2430

Arg Pro Val Leu Val Arg Gln Ser Thr Phe Ile Lys Glu Ala Pro
    2435                2440                2445

Ser Pro Thr Leu Arg Arg Lys Leu Glu Glu Ser Ala Ser Phe Glu
    2450                2455                2460

Ser Leu Ser Pro Ser Ser Arg Pro Ala Ser Pro Thr Arg Ser Gln
    2465                2470                2475

Ala Gln Thr Pro Val Leu Ser Pro Ser Leu Pro Asp Met Ser Leu
    2480                2485                2490

Ser Thr His Ser Ser Val Gln Ala Gly Gly Trp Arg Lys Leu Pro
    2495                2500                2505

Pro Asn Leu Ser Pro Thr Ile Glu Tyr Asn Asp Gly Arg Pro Ala
    2510                2515                2520

Lys Arg His Asp Ile Ala Arg Ser His Ser Glu Ser Pro Ser Arg
    2525                2530                2535

Leu Pro Ile Asn Arg Ser Gly Thr Trp Lys Arg Glu His Ser Lys
    2540                2545                2550

His Ser Ser Ser Leu Pro Arg Val Ser Thr Trp Arg Arg Thr Gly
    2555                2560                2565

Ser Ser Ser Ser Ile Leu Ser Ala Ser Ser Glu Ser Ser Glu Lys
    2570                2575                2580

Ala Lys Ser Glu Asp Glu Lys His Val Asn Ser Ile Ser Gly Thr
    2585                2590                2595

Lys Gln Ser Lys Glu Asn Gln Val Ser Ala Lys Gly Thr Trp Arg
    2600                2605                2610

Lys Ile Lys Glu Asn Glu Phe Ser Pro Thr Asn Ser Thr Ser Gln
    2615                2620                2625

Thr Val Ser Ser Gly Ala Thr Asn Gly Ala Glu Ser Lys Thr Leu
    2630                2635                2640

Ile Tyr Gln Met Ala Pro Ala Val Ser Lys Thr Glu Asp Val Trp
```

```
                2645              2650                   2655
Val Arg Ile Glu Asp Cys Pro Ile Asn Asn Pro Arg Ser Gly Arg
    2660            2665             2670
Ser Pro Thr Gly Asn Thr Pro Pro Val Ile Asp Ser Val Ser Glu
    2675            2680             2685
Lys Ala Asn Pro Asn Ile Lys Asp Ser Lys Asp Asn Gln Ala Lys
    2690            2695             2700
Gln Asn Val Gly Asn Gly Ser Val Pro Met Arg Thr Val Gly Leu
    2705            2710             2715
Glu Asn Arg Leu Asn Ser Phe Ile Gln Val Asp Ala Pro Asp Gln
    2720            2725             2730
Lys Gly Thr Glu Ile Lys Pro Gly Gln Asn Asn Pro Val Pro Val
    2735            2740             2745
Ser Glu Thr Asn Glu Ser Ser Ile Val Glu Arg Thr Pro Phe Ser
    2750            2755             2760
Ser Ser Ser Ser Ser Lys His Ser Ser Pro Ser Gly Thr Val Ala
    2765            2770             2775
Ala Arg Val Thr Pro Phe Asn Tyr Asn Pro Ser Pro Arg Lys Ser
    2780            2785             2790
Ser Ala Asp Ser Thr Ser Ala Arg Pro Ser Gln Ile Pro Thr Pro
    2795            2800             2805
Val Asn Asn Asn Thr Lys Lys Arg Asp Ser Lys Thr Asp Ser Thr
    2810            2815             2820
Glu Ser Ser Gly Thr Gln Ser Pro Lys Arg His Ser Gly Ser Tyr
    2825            2830             2835
Leu Val Thr Ser Val
    2840

<210> SEQ ID NO 2
<211> LENGTH: 10740
<212> TYPE: DNA
<213> ORGANISM: Homo sapiens

<400> SEQUENCE: 2
gtattggtgc agcccgccag ggtgtcactg gagacagaat ggaggtgctg ccggactcgg      60
aaatggggtc caagggtagc caaggatggc tgcagcttca tatgatcagt tgttaaagca     120
agttgaggca ctgaagatgg agaactcaaa tcttcgacaa gagctagaag ataattccaa     180
tcatcttaca aaactggaaa ctgaggcatc taatatgaag gaagtactta acaactaca      240 aggaagtatt gaagatgaag ctatggcttc ttctggacag attgatttat tagagcgtct     300
taaagagctt aacttagata gcagtaattt ccctggagta aaactgcggt caaaaatgtc     360
cctccgttct tatggaagcc gggaaggatc tgtatcaagc cgttctggag agtgcagtcc     420
tgttcctatg ggttcatttc caagaagagg gtttgtaaat ggaagcagag aaagtactgg     480
atatttagaa gaacttgaga agagaggtc attgcttctt gctgatcttg acaaagaaga     540
aaaggaaaaa gactggtatt acgctcaact tcagaatctc actaaaagaa tagatagtct     600
tcctttaact gaaaattttt ccttacaaac agatatgacc agaaggcaat tggaatatga     660
agcaaggcaa atcagagttg cgatggaaga caactaggac ctgccagg atatggaaaa      720 acgagcacag cgaagaatag ccagaattca gcaaatcgaa aaggacatac ttcgtatacg     780
acagctttta cagtcccaag caacagaagc agagaggtca tctcagaaca agcatgaaac     840
cggctcacat gatgctgagc ggcagaatga aggtcaagga gtgggagaaa tcaacatggc     900
```

-continued

```
aacttctggt aatggtcagg gttcaactac acgaatggac catgaaacag ccagtgtttt    960
gagttctagt agcacacact ctgcacctcg aaggctgaca agtcatctgg gaaccaaggt   1020
ggaaatggtg tattcattgt tgtcaatgct tggtactcat gataaggatg atatgtcgcg   1080
aactttgcta gctatgtcta gctcccaaga cagctgtata tccatgcgac agtctggatg   1140
tcttcctctc ctcatccagc ttttacatgg caatgacaaa gactctgtat tgttgggaaa   1200
ttcccggggc agtaaagagg ctcgggccag ggccagtgca gcactccaca acatcattca   1260
ctcacagcct gatgacaaga gaggcaggcg tgaaatccga gtccttcatc ttttggaaca   1320
gatacgcgct tactgtgaaa cctgttggga gtggcaggaa gctcatgaac caggcatgga   1380
ccaggacaaa aatccaatgc cagctcctgt tgaacatcag atctgtcctg ctgtgtgtgt   1440
tctaatgaaa ctttcatttg atgaagagca tagacatgca atgaatgaac taggggggact   1500
acaggccatt gcagaattat tgcaagtgga ctgtgaaatg tatgggctta ctaatgacca   1560
ctacagtatt acactaagac gatatgctgg aatggctttg acaaacttga cttttggaga   1620
tgtagccaac aaggctacgc tatgctctat gaaaggctgc atgagagcac ttgtggccca   1680
actaaaatct gaaagtgaag acttacagca ggttattgcg agtgttttga ggaatttgtc   1740
ttggcgagca gatgtaaata gtaaaaagac gttgcgagaa gttggaagtg tgaaagcatt   1800
gatggaatgt gctttagaag ttaaaaagga atcaaccctc aaaagcgtat tgagtgcctt   1860
atggaatttg tcagcacatt gcactgagaa taaagctgat atatgtgctg tagatggtgc   1920
acttgcattt ttggttggca ctcttactta ccggagccag acaaacactt tagccattat   1980
tgaaagtgga ggtgggatat tacgaatgt gtccagcttg atagctacaa atgaggacca   2040
caggcaaatc ctaagagaga acaactgtct acaaacttta ttacaacact taaaatctca   2100
tagtttgaca atagtcagta atgcatgtgg aactttgtgg aatctctcag caagaaatcc   2160
taaagaccag gaagcattat gggacatggg ggcagttagc atgctcaaga acctcattca   2220
ttcaaagcac aaaatgattg ctatgggaag tgctgcagct ttaaggaatc tcatggcaaa   2280
taggcctgcg aagtacaagg atgccaatat tatgtctcct ggctcaagct tgccatctct   2340
tcatgttagg aaacaaaaag ccctagaagc agaattagat gctcagcact atcagaaac   2400
ttttgacaat atagacaatt taagtcccaa ggcatctcat cgtagtaagc agagacacaa   2460
gcaaagtctc tatggtgatt atgtttttga caccaatcga catgatgata ataggtcaga   2520
caattttaat actggcaaca tgactgtcct ttcaccatat ttgaatacta cagtgttacc   2580
cagctcctct tcatcaagag gaagcttaga tagttctcgt tctgaaaaag atagaagttt   2640
ggagagagaa cgcggaattg gtctaggcaa ctaccatcca gcaacagaaa atccaggaac   2700
ttcttcaaag cgaggtttgc agatctccac cactgcagcc cagattgcca aagtcatgga   2760
agaagtgtca gccattcata cctctcagga agacagaagt tctgggtcta ccactgaatt   2820
acattgtgtg acagatgaga gaaatgcact tagaagaagc tctgctgccc atacacattc   2880
aaacacttac aatttcacta agtcggaaaa ttcaaatagg acatgttcta tgccttatgc   2940
caaattagaa tacaagagat cttcaaatga tagtttaaat agtgtcagta gtagtgatgg   3000
ttatggtaaa agaggtcaaa tgaaaccctc gattgaatcc tattctgaag atgatgaaag   3060
taagttttgc agttatggtc aatacccagc cgacctagcc cataaaatac atagtgcaaa   3120
tcatatggat gataatgatg agaaactaga tacaccaata aattatagtc ttaaatattc   3180
agatgagcag ttgaactctg gaaggcaaag tccttcacag aatgaaagat gggcaagacc   3240
caaacacata atagaagatg aaataaaaca aagtgagcaa agacaatcaa ggaatcaaag   3300
```

-continued

```
tacaacttat cctgtttata ctgagagcac tgatgataaa cacctcaagt tccaaccaca   3360 tttttggacag caggaatgtg tttctccata caggtcacgg ggagccaatg gttcagaaac   3420
aaatcgagtg ggttctaatc atggaattaa tcaaaatgta agccagtctt tgtgtcaaga   3480
agatgactat gaagatgata agcctaccaa ttatagtgaa cgttactctg aagaagaaca   3540
gcatgaagaa gaagagagac caacaaatta tagcataaaa tataatgaag agaaacgtca   3600
tgtggatcag cctattgatt atagtttaaa atatgccaca gatattcctt catcacagaa   3660
acagtcattt tcattctcaa agagttcatc tggacaaagc agtaaaaccg aacatatgtc   3720
ttcaagcagt gagaatacgt ccacaccttc atctaatgcc aagaggcaga atcagctcca   3780
tccaagttct gcacagagta gaagtggtca gcctcaaaag gctgccactt gcaaagtttc   3840
ttctattaac caagaaacaa tacagactta ttgtgtagaa gatactccaa tatgtttttc   3900
aagatgtagt tcattatcat ctttgtcatc agctgaagat gaaataggat gtaatcagac   3960
gacacaggaa gcagattctg ctaatacccct gcaaatagca gaaataaaag aaaagattgg   4020
aactaggtca gctgaagatc ctgtgagcga agttccagca gtgtcacagc accctagaac   4080
caaatccagc agactgcagg gttctagttt atcttcagaa tcagccaggc acaaagctgt   4140
tgaattttct tcaggagcga aatctccctc caaaagtggt gctcagacac ccaaaagtcc   4200
acctgaacac tatgttcagg agaccccact catgtttagc agatgtactt ctgtcagttc   4260
acttgatagt tttgagagtc gttcgattgc cagctccgtt cagagtgaac catgcagtgg   4320
aatggtaagt ggcattataa gccccagtga tcttccagat agccctggac aaaccatgcc   4380
accaagcaga agtaaaacac ctccaccacc tcctcaaaca gctcaaacca gcgagaagt   4440 acctaaaaat aaagcaccta ctgctgaaaa gagagagagt ggacctaagc aagctgcagt   4500
aaatgctgca gttcagaggg tccaggttct tccagatgct gatactttat acattttgc   4560 cacgaaaagt actccagatg gattttcttg ttcatccagc ctgagtgctc tgagcctcga   4620
tgagccattt atacagaaag atgtggaatt aagaataatg cctccagttc aggaaaatga   4680
caatgggaat gaaacagaat cagagcagcc taaagaatca aatgaaaacc aagagaaaga   4740
ggcagaaaaa actattgatt ctgaaaagga cctattagat gattcagatg atgatgatat   4800
tgaaatacta gaagaatgta ttatttctgc catgccaaca aagtcatcac gtaaagcaaa   4860
aaagccagcc cagactgctt caaaattacc tccacctgtg gcaaggaaac caagtcagct   4920
gcctgtgtac aaacttctac catcacaaaa caggttgcaa ccccaaaagc atgttagttt   4980
tacaccgggg gatgatatgc cacgggtgta ttgtgttgaa gggaccccta taaacttttc   5040
cacagctaca tctctaagtg atctaacaat cgaatcccct ccaaatgagt tagctgctgg   5100
agaaggagtt agaggagggg cacagtcagg tgaatttgaa aaacgagata ccattcctac   5160
agaaggcaga agtacagatg aggctcaagg aggaaaaacc tcatctgtaa ccatacctga   5220
attggatgac aataaagcag aggaaggtga tattcttgca gaatgcatta attctgctat   5280
gcccaaaggg aaaagtcaca agcctttccg tgtgaaaag ataatggacc aggtccagca   5340
agcatctgcg tcttcttctg cacccaacaa aaatcagtta gatggtaaga aaaagaaacc   5400
aacttcacca gtaaaaccta taccacaaaa tactgaatat aggacacgtg taagaaaaaa   5460
tgcagactca aaaaataatt taaatgctga gagagttttc tcagacaaca aagattcaaa   5520
gaaacagaat ttgaaaaaata attccaaggt cttcaatgat aagctcccaa ataatgaaga   5580
tagagtcaga ggaagttttg cttttgattc acctcatcat tacacgccta ttgaaggaac   5640
```

```
tccttactgt ttttcacgaa atgattcttt gagttctcta gattttgatg atgatgatgt   5700
tgacctttcc agggaaaagg ctgaattaag aaaggcaaaa gaaaataagg aatcagaggc   5760
taaagttacc agccacacag aactaacctc caaccaacaa tcagctaata agacacaagc   5820
tattgcaaag cagccaataa atcgaggtca gcctaaaccc atacttcaga acaatccac    5880
ttttccccag tcatccaaag acataccaga cagaggggca gcaactgatg aaaagttaca   5940
gaattttgct attgaaaata ctccggtttg cttttctcat aattcctctc tgagttctct   6000
cagtgacatt gaccaagaaa acaacaataa agaaaatgaa cctatcaaag agactgagcc   6060
ccctgactca cagggagaac caagtaaacc tcaagcatca ggctatgctc ctaaatcatt   6120
tcatgttgaa gatacccag tttgtttctc aagaaacagt tctctcagtt ctcttagtat     6180
tgactctgaa gatgacctgt tgcaggaatg tataagctcc gcaatgccaa aaagaaaaa    6240
gccttcaaga ctcaagggtg ataatgaaaa acatagtccc agaaatatgg gtggcatatt   6300
aggtgaagat ctgacacttg atttgaaaga tatacagaga ccagattcag aacatggtct   6360
atcccctgat tcagaaaatt ttgattggaa agctattcag gaaggtgcaa attccatagt   6420
aagtagttta catcaagctg ctgctgctgc atgtttatct agacaagctt cgtctgattc   6480
agattccatc cttcccctga aatcaggaat ctctctggga tcaccatttc atcttacacc   6540
tgatcaagaa gaaaaaccct ttacaagtaa taaaggccca cgaattctaa accaggggga   6600
gaaaagtaca ttggaaacta aaagataga atctgaaagt aaaggaatca aaggaggaaa     6660
aaaagtttat aaaagtttga ttactggaaa agttcgatct aattcagaaa tttcaggcca   6720
aatgaaacag cccccttcaag caaacatgcc ttcaatctct cgaggcagga caatgattca   6780
tattccagga gttcgaaata gctcctcaag tacaagtcct gtttctaaaa aaggcccacc    6840
ccttaagact ccagcctcca aaagccctag tgaaggtcaa acagccacca cttctccctag  6900
aggagccaag ccatctgtga atcagaatt aagccctgtt gccaggcaga catcccaaat    6960
aggtgggtca agtaaagcac cttctagatc aggatctaga gattcgaccc cttcaagacc   7020
tgcccagcaa ccattaagta gacctataca gtctcctggc cgaaactcaa tttcccctgg   7080
tagaaatgga ataagtcctc ctaacaaatt atctcaactt ccaaggacat catcccctag    7140
tactgcttca actaagtcct caggttctgg aaaaatgtca tatacatctc caggtagaca   7200
gatgagccaa cagaaccta ccaaacaaac aggtttatcc aagaatgcca gtagtattcc     7260
aagaagtgag tctgcctcca aaggactaaa tcagatgaat aatggtaatg gagccaataa    7320
aaaggtagaa ctttctagaa tgtcttcaac taaatcaagt ggaagtgaat ctgatagatc     7380
agaaagacct gtattagtac gccagtcaac tttcatcaaa gaagctccaa gcccaacctt    7440
aagaagaaaa ttggaggaat ctgcttcatt tgaatctctt tctccatcat ctagaccagc    7500
ttctccccact aggtcccagg cacaaactcc agttttaagt ccttcccttc ctgatatgtc   7560
tctatccaca cattcgtctg ttcaggctgg tggatggcga aaactcccac ctaatctcag   7620
tcccactata gagtataatg atggaagacc agcaaagcgc catgatattg cacggtctca   7680
ttctgaaagt ccttctagac ttccaatcaa taggtcagga acctggaaac gtgagcacag   7740
caaacattca tcatcccttc ctcgagtaag cacttggaga agaactggaa gttcatcttc   7800
aattctttct gcttcatcag aatccagtga aaagcaaaa agtgaggatg aaaaacatgt   7860
gaactctatt tcaggaacca aacaaagtaa agaaaaccaa gtatccgcaa aaggaacatg   7920
gagaaaaata aaagaaaatg aattttctcc cacaaatagt acttctcaga ccgtttcctc    7980
aggtgctaca aatggtgctg aatcaaagac tctaatttat caaatggcac ctgctgtttc   8040
```

```
taaaacagag gatgtttggg tgagaattga ggactgtccc attaacaatc ctagatctgg    8100
aagatctccc acaggtaata ctcccccggt gattgacagt gtttcagaaa aggcaaatcc    8160
aaacattaaa gattcaaaag ataatcaggc aaaacaaaat gtgggtaatg gcagtgttcc    8220
catgcgtacc gtgggtttgg aaaatcgcct gaactccttt attcaggtgg atgcccctga    8280
ccaaaaagga actgagataa aaccaggaca aaataatcct gtccctgtat cagagactaa    8340
tgaaagttct atagtggaac gtaccccatt cagttctagc agctcaagca aacacagttc    8400
acctagtggg actgttgctg ccagagtgac tcctttaat tacaacccaa gccctaggaa     8460
aagcagcgca gatagcactt cagctcggcc atctcagatc ccaactccag tgaataacaa    8520
cacaaagaag cgagattcca aaactgacag cacagaatcc agtggaaccc aaagtcctaa    8580
gcgccattct gggtcttacc ttgtgacatc tgtttaaaag agaggaagaa tgaaactaag    8640
aaaattctat gttaattaca actgctatat agacattttg tttcaaatga aactttaaaa    8700
gactgaaaaa ttttgtaaat aggtttgatt cttgttagag ggttttttgtt ctggaagcca   8760
tatttgatag tatactttgt cttcactggt cttattttgg gaggcactct tgatggttag    8820
gaaaaaaata gtaaagccaa gtatgtttgt acagtatgtt ttacatgtat ttaaagtagc    8880
atcccatccc aacttccttt aattattgct tgtcttaaaa taatgaacac tacagataga    8940
aaatatgata tattgctgtt atcaatcatt tctagattat aaactgacta aacttacatc    9000
agggaaaaat tggtatttat gcaaaaaaaa atgttttgt ccttgtgagt ccatctaaca     9060
tcataattaa tcatgtggct gtgaaattca cagtaatatg gttcccgatg aacaagttta    9120
cccagcctgc tttgctttac tgcatgaatg aaactgatgg ttcaatttca gaagtaatga    9180
ttaacagtta tgtggtcaca tgatgtgcat agagatagct acagtgtaat aatttacact    9240
attttgtgct ccaaacaaaa caaaaatctg tgtaactgta aaacattgaa tgaaactatt    9300
ttacctgaac tagattttat ctgaaagtag gtagaatttt tgctatgctg taatttgttg    9360
tatattctgg tatttgaggt gagatggctg ctctttttat t aatgagacat gaattgtgtc   9420
tcaacagaaa ctaaatgaac atttcagaat aaattattgc tgtatgtaaa ctgttactga    9480
aattggtatt tgtttgaagg gtcttgtttc acatttgtat taataattgt ttaaaatgcc    9540
tcttttaaaa gcttatataa attttttct tcagcttcta tgcattaaga gtaaaattcc      9600
tcttactgta ataaaacaa ttgaagaaga ctgttgccac ttaaccattc catgcgttgg     9660
cacttatcta ttcctgaaat ttcttttatg tgattagctc atcttgattt ttaatatttt    9720
tccacttaaa cttttttttc ttactccact ggagctcagt aaaagtaaat tcatgtaata    9780
gcaatgcaag cagcctagca cagactaagc attgagcata ataggcccac ataatttcct    9840
ctttcttaat attatagaat tctgtacttg aaattgattc ttagacattg cagtctcttc    9900
gaggctttac agtgtaaact gtcttgcccc ttcatcttct tgttgcaact gggtctgaca    9960
tgaacacttt ttatcaccct gtatgttagg gcaagatctc agcagtgaag tataatcagc   10020
actttgccat gctcagaaaa ttcaaatcac atggaacttt agaggtagat ttaatacgat   10080
taagatattc agaagtatat tttagaatcc ctgcctgtta aggaaacttt atttgtggta   10140
ggtacagttc tggggtacat gttaagtgtc cccttataca gtggagggaa gtcttccttc   10200
ctgaaggaaa ataaactgac acttattaac taagataatt tacttaatat atcttccctg   10260
atttgtttta aaagatcaga gggtgactga tgatacatgc atacatattt gttgaataaa   10320
tgaaaattta ttttttagtga taagattcat acactctgta tttggggagg gaaaaccttt   10380
```
ttaagcatgg tggggcactc agataggagt gaatacacct acctggtgcc ttgaaaatca    10440
catcaagtag ttaattatct accccttacc tgtgtttata acttccaggt aatgagaatg    10500
atttttttta aagctaaaat gccagtaaat aaaagtgcta tgacttgagc taagatattt    10560
gactccaatg cctgtactgt gtctactgca ccactttgta aacacttcaa tttactatct    10620
ttgaaatgat tgacctttaa attttttgcca aatgttatct gaattgtct atgaatacca    10680 tctacttctg ttgttttccc aggcttccat aaacaatgga gatacatgca aaaaaaaaa    10740

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
tgggagttgc atgaagagtg                                                    20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
tacgcagttc tcatcgacca                                                    20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
ctcctcccca gtctacatcg                                                    20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
aaactgatcc ccgcattttt                                                    20

<210> SEQ ID NO 7
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7

-continued cttcctgatc ggcgtgag                                                  18

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
cctgcttctg gtggtaatcc                                                20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gagctggtgg tttcaccttc                                                20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
ggtcgaagtc ataggaccca                                                20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
gcttctggca aggaagacac                                                20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ccagccttct ccagattcaa                                                20

<210> SEQ ID NO 13
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 13
ttactgtcca cacagcacgc                                              20

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
acttcctgaa cactggccc                                               19

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
gaggcatttt ggagcagagt                                              20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
tcagggttgg ttttgatggt                                              20
```